(12) United States Patent
Banks et al.

(10) Patent No.: US 7,022,684 B2
(45) Date of Patent: Apr. 4, 2006

(54) TREATMENT OF RUMEN ACIDOSIS WITH α-AMYLASE INHIBITORS

(75) Inventors: Bernard Joseph Banks, County of Kent (GB); Mark Andrew Haxell, County of Kent (GB); Graham Lunn, County of Kent (GB); Michael Stephen Pacey, County of Kent (GB); Lee Richard Roberts, County of Kent (GB)

(73) Assignee: Pfizer Inc., New York, NY (US)

( * ) Notice: Subject to any disclaimer, the term of this patent is extended or adjusted under 35 U.S.C. 154(b) by 185 days.

(21) Appl. No.: 10/059,667

(22) Filed: Jan. 29, 2002

(65) Prior Publication Data

US 2003/0060424 A1 Mar. 27, 2003

Related U.S. Application Data

(63) Continuation of application No. 09/864,515, filed on May 24, 2001, now abandoned.

(60) Provisional application No. 60/225,156, filed on Aug. 14, 2000, provisional application No. 60/218,494, filed on Jul. 14, 2000, and provisional application No. 60/218,326, filed on Jul. 14, 2000.

(30) Foreign Application Priority Data

| May 24, 2000 | (GB) | ............................................. 0012760 |
| May 24, 2000 | (GB) | ............................................. 0012793 |
| Jul. 17, 2000 | (GB) | ............................................. 0017495 |

(51) Int. Cl.
*A01N 43/04* (2006.01)
*A61K 31/715* (2006.01)

(52) U.S. Cl. ........................ 514/54; 536/17.2; 536/18.7; 536/123.1

(58) Field of Classification Search ................ 536/17.2, 536/18.7, 123.1; 514/54

See application file for complete search history.

(56) References Cited

U.S. PATENT DOCUMENTS

| 4,062,950 A | 12/1977 | Frommer et al. ........... 424/181 |
| 4,175,123 A | 11/1979 | Junge et al. ............... 424/180 |
| 4,273,765 A | * 6/1981 | Suhara et al. .............. 424/180 |
| 4,618,602 A | 10/1986 | Vertesy et al. ............... 514/54 |
| 4,885,361 A | 12/1989 | Wessel ........................ 536/118 |

FOREIGN PATENT DOCUMENTS

| CH | 648326 | 3/1985 |
| DE | 19821038 | 11/1999 |
| EP | 0049981 | 7/1984 |

(Continued)

OTHER PUBLICATIONS

Malcolm Woodbine; Antimicrobials and Agriculture; The Proceedings of the 4th International Symposium on Antibiotics in Agriculture: Benefits and Malefits; (1984) 331–347.

(Continued)

*Primary Examiner*—James O. Wilson
*Assistant Examiner*—Patrick Lewis
(74) *Attorney, Agent, or Firm*—Peter C. Richardson; Martha G. Munchhof; Lorraine B. Ling

(57) ABSTRACT

The invention described herein relates to: the use of an effective inhibitor of a bacterial α-amylase and/or α-glucosidase in the manufacture of a composition for the treatment of rumen acidosis; a method of treatment of rumen acidosis which comprises administration of an effective amount of an effective inhibitor of a bacterial α-amylase and/or α-glucosidase to a ruminant; a formulation suitable for the treatment of rumen acidosis in an animal which comprises an effective inhibitor of a bacterial α-amylase and/or α-glucosidase in admixture with a suitable excipient, diluent or carrier selected with regard to the intended route of administration and standard pharmaceutical/veterinary/farming practice; screening methods useful in the identification of a suitable inhibitor of a bacterial α-amylase and/or α-glucosidase for the treatment of acidosis in a ruminant; a process for improving ruminant milk quality and/or quantity which comprises treatment of a ruminant with an effective amount of an inhibitor of bacterial α-amylase and/or α-glucosidase; a compound of the formula I:

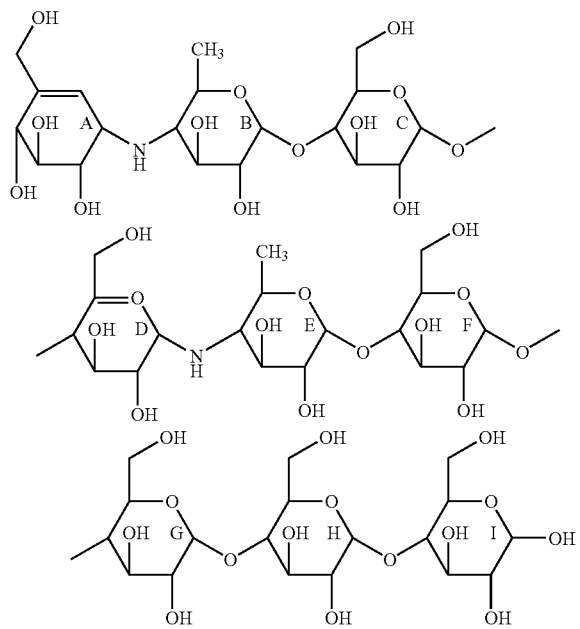

or veterinarily acceptable salt, solvate (including hydrate) or prodrug thereof; and processes to make an effective inhibitor of a bacterial α-amylase and/or α-glucosidase useful for the treatment of acidosis in a ruminant.

2 Claims, No Drawings

FOREIGN PATENT DOCUMENTS

| | | |
|---|---|---|
| EP | 0194794 | 9/1986 |
| EP | 0089812 | 10/1986 |
| EP | 0240175 | 10/1991 |
| EP | 0520557 | 12/1992 |
| EP | 0599646 | 9/2002 |
| ES | 556500 | 6/1986 |
| GB | 1482543 | 9/1974 |
| JP | 2000-44589 | 2/2000 |
| JP | 2001-59657 | 3/2001 |
| WO | WO 9617525 | 6/1996 |
| WO | WO9620945 | 7/1996 |

OTHER PUBLICATIONS

Robinson, et al.; Influence of Carbohydrate Source and Buffer on Rumen Fermentation Characteristic, Milk Yield, and Milk Composition in Early–Lactation Holstein Cows; Journal of Dairy Science (1999) 82:2486–2496.

Kung et al.; Preventing In Vitro Lactate Accumulation in Ruminal Fermentations by Inoculation with *Megasphaera elsdenii;* Journal of Animal Science; (1995) 72:250–256.

Scott A. Martin; Manipulation of Ruminal Fermentation with Organic Acids: A Review; Journal of Animal Science (1995) 76:3123–3132.

Martin, et al.; Effects of DL–Malate on Ruminal Metabolism and Performance of Cattle Fed a High–Concentrate Diet; Journal of Animal Science (1999) 77:1008–1015.

Teather, et al.; Manipulating the Rumen Microflora with Bacteriocins to Improve Ruminant Production; Canadian Journal of Animal Science (1998) 78 (supplement) pp. 57–69.

The Use of Drugs in Food Animals: Benefits and Risks; CABI publishing (1999).

Thorniley, et al.; A single drench of virginiamycin to increase safety of feeding grain to sheep; Australian Journal of Agricultural Research; (1998) 49:899–906.

Wiryawan, et al.; Probiotic control of lactate accumulation in acutely grain–fed sheep; Australian Journal of Agricultural Research; (1995) 46:1555–1568.

Kay, et al.; The Relationship between the Acidity of the Rumen Contents and Rumenitis, in Calves fed on Barley; Research in Veterinary Science; (1969) 10:181–187.

McManus, et al.; Microlesions on Rumen Papillae of Sheep Fed Diets of Wheat Grain; Research in Veterinary Science; (1977) 22:135–137.

Lameness Cost UK Dairy Herds—NMR; Animal Pharm. No. 417 (1999) p. 6.

Burrin, et al.; Response to Monensin in Cattle During Subacute Acidosis; Journal of Animal Science (1986) 63:888–893.

Coe, et al.; Effect of Virginiamycin on Ruminal Fermentation in Cattle During Adaptation to a High Concentrate Diet and During an Induced Acidosis; Journal of Animal Science (1999) 77:2259–2268.

Dirksen; Acidosis Physiology of Digestion and Metabolism in the Ruminant; Proceedings of the Third International Symposium Cambridge, England (1969) ED. A.T. Phillipson, Oriel Press.

Nagaraja, et al.; Nutrition and Disease; Veterinary Clinics of North America: Food Animal Practice (1998) 41(2) 257–277.

Nagaraja, et al.; Effect of Ionophore Antibiotics on Experimentally Induced Lactic Acidosis in Cattle; Am. J. of Veterinary Research (1985) 46(12) 2444–2452.

Nocek; Bovine Acidosis; Implications on Laminitis; J. of Dairy Science (1997) 80:1005–1028.

Nordlund, et al.; Herd–based Rumenocentesis: A Clinical Approach to the Diagnosis of Subacute Rumen Acidosis; Compendium on Continuing Education for the Practicing Veterinarian; (1995) p. 48–56.

Owens, et al.; Acidosis in Cattle: A Review, J. of Animal Science (1998) 76:275–286.

"New α–Amylase Inhibitor, Trestatins, III Structure Determination of New Trestatin Components Ro 09–0766, Ro 09–0767, and Ro 09–0768", *Journal of Antibiotics,* pp. 182–186 (1984).

Barbaud, et al., "Synthesis of the First Pseudosugar–C–disaccharide. A Potential Antigen for Eliciting Glycoside–bond Forming Antibodies with Catalytic Groups", *Tetrahedron* 51(33), pp. 9063–9078 (1995).

Berge, et al., "Pharmaceutical Salts", *Journal of Pharmaceutical Sciences* 66(1), pp. 1–19 (1977).

Blanc–Muesser, et al., "Syntheses Stereoselectives de 1–Thioglycosides", *Carbohydrate Res* 67, pp. 305–328 (1978).

Bornaghi, et al., "Transfer Reactions Catalyzed by cyclodextrin Glycosyltransferase Using 4–Thiomaltosyl and C–maltosyl Fluorides as Artificial Donors", *Carbohydrate Res.* 305, pp. 561–568 (1997).

Chatterjee, et al., "Glucosidation of Betulinic Acid by Cunninghamella Species", *J. Nat. Prod.* 62, pp. 761–763 (1998).

Coe, et al., "Effect of Virginamycin on Ruminal Fermentation in Cattle During Adaptation to a High Concentrate Diet and During an Induced Acidosis", *J. Anim. Sci* 77, pp. 2259–2268 (1999).

Crout, et al., "Glycosidases and Blycosyl Transferases in Glycoside and Oligosaccharide Synthesis", *Curr Opinion in Chem Biol.* 2, pp. 969–111 (1998).

Evers, et al., "Further Syntheses Employing Phsophorylase", *Bioorg. & Medic. Chem* 5(5), pp. 857–863 (1997).

Fukuhara, et al., "Isolation and Structure–activity Relationship of Some Amylostatins (F–1b Fraction) Produced by *Streptomyces diastaticus* subsp. *amylostaticus* No. 940", *Agric. Biol. Chem,* 46(7), pp. 1941–1945 (1982).

Hormi, et al., "Experimental Studies of Lewis Acid Catalyzed Additions of Long Chained Alchohols to Activated 1,4–Benzoquinone", *Tetrahedron* 54, pp. 1943–1952 (1998).

Garcia–Granados, et al., "Biotransformation of ENT–6α–Acetoxy– and ENT–6–Ketomanoyl Oxides with *Rhizopus nigricans* and *Curvularia lunata* Cultures", *Phytochemistry* 45(2), pp. 283–291 (1997).

Kim et al., "Comparative Study of the Inhibition of α–Glucosidase, α–Amylase, and Cyclomaltodextrin Glucanosyltransferase by Acarbose, Isoacarbose, and Acarviosine–Glucose", *Archives of Biochemistry and Biophysics* 371(2), pp. 277–283 (1999).

Kim et al, "Studies on Screening and Isolation of α–Amylase Inhibitors of Soil Microorganismls (II)", *Kor. J. Mycol,* 13(4), pp. 203–212 (1985).

Machius, et al., "Carbohydrate and Protein–based Inhibitors of Porcine Pancreatic α–Amylase: Structure Analysis and Comparison of Their Binding Characteristics", *J. Mol. Biol,* 260, pp. 409–421 (1996).

McAuliffe, et al., "β–Acarbose: A Potential Inhibitor of β–D–Glucosidases and β–D–Glucan Hydrolases", *Tetrahedron Letters* 37(14), pp. 2479–2482 (1996).

Oda, et al., "Double Coupling of Acetyl Coenzyme A Production and Microbial Esterification with Alcohol Acetyltransferase in an Interface Bioreactor", *Journ. Of Ferm. And Bioeng,* 83 (5), pp. 423–428 (1997).

Ogawa, et al., "Total Synthesis of Acarbose and Adiposin–2", *J. Chem. Soc., Commun,* Pp. 605–606 (1988).

Ohyama, et al., "Purification and Some Properties of Amylase Inhibitor (S–AI)", *Agric. Biol. Chem,* 41 (11), pp. 2221–2228 (1977).

Ott, et al., "A Method for Constructing the C44–C51 Side Chain of Altohyrtin C", *Org. Letters* 1(9), pp. 1475–1478 (1999).

Park, et al., "Transglycosylation Reactions of *Bacillus stearothermophilus* maltogenic amylase with acarbose and various acceptor", *Carbohydrate Res.* 313, pp. 235–246 (1998).

Rauter, et al., "Deoxygenation of C–e and Stereospecific Branched–Chain Construction at C–3 of a Methyl Hexopranuloside. Synthetic Approach to the Amipurimycin Sugar Moiety", *J. Org. Chem,* 61, pp. 3594–3596 (1996).

Richard, et al., "Effect of Acarbose on Glucose and Insulin Response to Sucrose Load in Reactive Hypoglycemia", *Diabete & Metabolisme* 14, pp. 114–118 (1988).

Saleh, et al., "Preparation of (±)–1–Allyl–4–deoxy Mannose Derivatives", *Synlett* 5, pp. 617–619 (1999).

Shiozaki, et al., "Synthesis of (S)–and ®–3[(Benyloxycarbonyl)Oxy]–2,2–Difluorotetradecanoic Acid", *Tetrahedron: Asymmetry* 3(3), pp. 451–458 (1992).

Scigelova, et al., "Glycosidases—a Great Synthetic Tool", *Journ. Of Molecular Catalysis B: Enzymatic* 6, pp. 483–494 (1999).

Sariaslani, et al., "Novel Biotransformations of 7–Ethoxycoumarin by *Streptomyces griseus*", *Appl. And Envir. Microbiol,* 48(2), pp. 468–474 (1983).

Takada, et al., "Chemo–Enzymatic Synthesis of Galactosylmaltooligosaccharidonolactone as a Substrate Analogue Inhibitor for Mammalian α–Amylase", *J. Biochem* 123, pp. 508–515 (1998).

Truscheit, et al., "Chemistry and Biochemistry of Microbial α–Glucosidase Inhibitors", *Angew. Chem. Int. Ed.* 20, pp. 744–761 (1981).

Uchida, et al., "Synthesis of New N–Containing Maltooligosaccharides, α–Amylase Inhibitors, and Their Biological Activities", *Chem. Pharm. Bull* 47(2), pp. 187–193 (1999).

Yokose, et al., "New α–Amylase Inhibitor, Trestatins II, Structure Determination of Trestatins A, B, and C", *The Journal of Antibiotics,* pp. 1166–1175 (1983).

"Validamycin H, A New Pseudo–Tetrasaccharide Antibiotic", *The Journal of Antibiotics* XLIII(8), pp. 1039–1041 (1990).

"Validamycin G and Validoxylamine G, New Members of the Validamycins", *The Journal of Antibiotics* XXXIX(10), pp. 1491–1495 (1986).

Microbial Blycosidation of Validamycins, *The Journal of Antibiotics* XXXI(9), pp. 936–938 (1978).

Asano, et al., "All Eight Possible Mono–β–D–Glucosides of Validoxylamine A", *The Journal of Antibiotics* 44(12), pp. 1406–1416 (1991).

Asano, et al., "Trehalase Inhibitors. Validoxylamine A and Related Compounds as Insecticides", *The Journal of Antibiotics* XLIII(6), pp. 722–726 (1990).

Bland–Muesser, et al., "Stereoselective Thioglycoside Syntheses. Part 4. A New Approach to 1,4–Linked 1–Thiodisaccharides and a Synthesis of Thiomaltose", *J.C.S. Perkin I,* pp. 15–18 (1982).

Boberg, et al., "Isolation and Structural Elucidation of biotransformation Products form Acarbose", *Arzneim–Frosch/Drug Res* 40 (I) (5), pp. 555–563 (1990).

Casset, et al., "Molecular Modelling of the Interaction Between the Catalytic Site of Pic Pancreatic α–Amylase and Amylose Fragments", *Eur. J. Biochem,* 232, pp. 284–293 (1995).

Czerkawski, et al., "Design and Development of Long–term Rumen Simulation Technique (Rusitec)", *Br. J. Nutr,* 38, pp. 371–384 (1977).

Despeyroux, et al., "Stereoselectivity in Nucleophilic Additions to the Carbonyl Group of Methyl 1,4,5–tris (trimethylsilyl)–3–Dehydroquinate", *Bull. Soc. Chim. Fr.* 134, pp. 777–784 (1997).

Furumoto, et al., "Enzymatic Synthesis of Glucoside Derivatives of Validamine and Vallenamine", *Chem. Pharm. Bull* 30(7), pp. 1871–1875 (1992).

Hasegawa, et al., "Chemical Modification of Validamycin A", *Agric. Biol. Chem* 44(1), pp. 143–147 (1980).

Horii, et al., "Studies on Validamycins, New Antibiotics. VIII Isolation and Characterization of Validamycins C, D, E, and F", *The Journal of Antibiotics* XXV(1), pp. 48–53 (1972).

Horii, et al., "Synthesis and α–Glucosidase Inhibitory Activity of N–Substituted Valioalamine Derivatives as Potential Oral Antidiabetic Agents", *J. med. Chem.* 29, pp. 1038–1046 (1986).

Itoh, et al., "Oligostatins, New Antibiotics with Amylase Inhibitory Activity", *The Journal of Antibiotics* XXXIV(11), pp. 1424–1428 (1981).

Jin, et al., "Biosynthetic Studies on Validamycins", *The Journal of Antibiotics* XL(3), pp. 329–339 (1987).

Junge, et al., "Derivatives of Acarbose and their Inhibitory Effects on α–Glucosidases", *Chem. Res. Lab. And Inst of Biochem.,* pp. 123–137.

Kameda, et al., "The Unsaturated Cyclitol Part of the New Antibiotics, the Validamycins", *J.C.S. Chem. Comm.,* pp. 746–747 (1972).

Kameda, et al., "Valiolamine, A New α–Glucosidase Inhibiting Aminocyclitol Produced by *Streptomyces hygroscopicus*", *The Journal of Antibiotics* XXXVII(11), pp. 1301–1307 (1984).

Kim, et al., "Sunthesis of Glucosyl–sugar Alcohols Using Blycosyltransferases and Structural Identification of Glucosyl–maltitol", *Journ. Of Microbiol. And Biotech.* 7(5), pp. 310–317 (1997).

Kittelmann, et al., "Microbial Hydroxylation and Simultaneous Formation of the 4"–O–Methylglucoside of the Tyrosine–Kinase Inhibitor CGP 62706", *Chimia* 53, pp. 594–596 (1999).

Kren, et al., "Glycosylation Employing Bio–systems: From Enzymes to Whole Cells", *Chem. Soc. Rev.* 26, pp. 463–473 (1997).

Lee, et al., "Synthesis of [7–$^3$H]valienamine, [7–$^3$H]valiolamine and [7–$^3$H]valiolone from validamycin A", *Journ. Of Labelled Compounds and Radiopharmaceuticals,* 42, pp. 361–372 (1999).

McAuliffe, et al., "β–Acarbose. VI The Synthesis of a Hydroxylated Derivative of a Diastereoisomer of Acarbose", *Aus. J. Chem.* 50, pp. 225–228 (1997).

McAuliffe, et al., "The Synthesis of a Diasteroisomer of Methyl Acarviosin", *Aust. J. Chem* 51, pp. 91–95 (1998).

McAuliffe, et al., "β–Acarbose. V The Synthesis of a Hydroxylated Derivative of a Diasteroisomer of Methyl Acarviosin", *Aust. J. Chem.* 50, pp. 219–224 (1997).

McDougall, et al., "Studies on Ruminant Saliva", *Biochem. Journal* 43(1), pp. 99–109 (1947).

Mueller, et al., "Radiosynthesis of [$^{14}$C]Acarbose", *Arzneim–Forsch/Drug. Res* 39(II) (10), pp. 1251–1253 (1989).

Mueller, et al., "Acarbose (BAY g5421) and Homologous α–Glucosidase Inhibitors from Actinoplanceae", *Inst. Of Biochem. And Chem. Res. Lab.*, pp. 109–122.

Nicotra, et al., "Stereocontrolled Synthesis of (±)–Vallenamine", *Gazz. Chim. Ital.* 119, 577–579 (1989).

Ogawa, et al., "Chemical Modification of the Sugar Moiety of Methyl Acarviosin; Synthesis and Inhibitory Activity of Eight Analogues Containing a 1,6–anhydro Bridge", *Carbohydrate Research* 250, pp. 177–184 (1993).

Ogawa, et al., "Synthesis of Pseudo–Dissacharide Derivative Having D–Manno Configuration, and Acarviosin Analogue", *Chem. Letters*, pp. 1977–1980 (1986).

Ogawa, et al., "Synthesis of DL–Validoxylamine A", *Chem. Letters*, pp. 749–752 (1982).

Ogawa, et al., "Synthesis of DL–Validoxylmaine B", *Chem. Letters*, pp. 279–282 (1982).

Ogawa, et al., "Synthesis of Potent α–Glucosidase Inhibitors: Methyl Acarviosin Analogue Composed of 1,6–Anhydro–β–D–Glucopyranose Residue", *J. Chem. Soc., Chem. Commun.*, pp. 1387–1388 (1990).

Ogawa, et al., "Synthesis of Some Valienamine Epoxides: On the Structure of the Alpha–Amylase Inhibitor NS–504", *Carbohydrate Res.* 175, pp. 294–301 (1988).

Ogawa, et al., "Synthesis of Carbocyclic Analogues of the Mannosyl Trisaccharide: Ether– and Imino–linked Methyl 3,6–bis(5a–carba–α–D–mannopyranosyl)–3,6–dideoxy–α–D–mannopyranosides", *Carbohydrate Res.* 274, pp. 183–196 (1995).

Ogawa, et al., "Synthesis of Glucosylceramide Analogues: Imino–Linked 5a–Carbaglycosylceramides, Potent and Specific Glucocerebrosidase Inhibitors", *J. Chem. Soc. Chem. Commun.*, pp. 1317–1318 (1994).

Ogawa, et al., "Synthesis and Biological Evaluation of four Stereoisomers of PDMP–analogue, N–(2–Decylamino–3–Hydroxy–3–Phenylprop–1–Yl)–β–Valienamine, and Related Compounds", *Bioorg & Medic. Chem. Letters* 7(14), pp. 1915–1920 (1997).

Ogawa, et al., "A Total Synthesis of 6 –Epivalidamycin A and its Diastereomer" *Chem. Letters*, pp. 1085–1088 (1983).

Ogawa, et al., "Synthetic Studies on Antibiotic Validamycins. Part 11. Synthesis of Validamycin A", *J. Chem. Soc. Perkin Trans I*, pp. 2369–2374 (1985).

Ogawa, et al., "Synthetic Studies on Antibiotic Validamycins. Part 12. Total Synthesis of (+)–Validamycin B and (+)–Validoxylamine B", *J. Chem. Soc. Perkin Trans I*, pp. 2675–2680 (1988).

Pacey, et al., "Preparation of 13–epi–Selamectin by Biotransformation Using a Blocked Mutant of *Streptomyces avermitilis*", *The Journal of Antibiotics* 53(3), pp. 301–305 (2000).

Petuch, et al., "Microbial Transformation of Immunosuppressive Compounds III. Glucosylation of Immunomycin (FR 900520) an dFK 506 by *Bacillus subtilis* ATCC 55060", *Journal of Industrial Microbiology* 13, pp. 131–135 (1994).

Shibata, et al., "Chemical Modification of the Sugar Part of Methyl Acarviosin: Synthesis and Inhibitory Activities of Nine Analogues", *Carbohydrate Res.* 228, pp. 377–398 (1992).

Shibata, et al., "Sunthesis and Biological Activities of Methyl Oligobiosaminide and Some Deoxy Isomers Thereof", *Carbohydrate Res.* 199, pp. 37–54 (1990).

Sigurskjold, et al., "Thermodynamics of Binding of Heterobidentate Ligands Consisting of Spacer–Connected Acarbose and β–cyclodextrin to the Catalytic and Starch–Binding Domains of Glucoamylase from *Aspergillus niger* Shows that the Catalytic and Starch Binding Sites Are in Close Proximity in Space", *Biochem* 37, 10446–10452 (1998).

Stick, et al., "β–Acarbose. VIII The Synthesis of some N–Linked Carba–Oligosaccharides", *Aust. J. Chem.* 52, pp. 895–904 (1999).

Suzuki, et al, "Enzymatic Formation of $4^G$–α–D–Glucopyranosyl–rutin", *Agric. Biol. Chem.* 55(1), pp. 181–187 (1991).

Toyokuni, et al., "Sunthetic Studies on the Validamycins. IV. Synthesis of DL–Vallenamine and Related Branched–chain Unsaturated Aminocyclitols", *Bull. Chem. Soc Jpn.* 56, pp. 1161–1170 (1983).

Tsunoda, et al., "Synthesis of Glycosylceramied Analogs Composed of Imino–Linked Unsaturated 5a–Carbaglycosyl Residues: Potent and Specific Gluco–and Galactocerebrosidase Inhibitors", *Liebigs Ann.*, pp. 279–284 (1995).

Uchida, et al., "Synthesis of Trehazolin Analogues Containing Modified Sugar Moieties", *J. Chem. Soc. Perkins Trans I*, pp. 1707–1717 (1995).

Yokose, et al., "α–Amylase Inhibitor, Trestatins I, Isoaltion, Characterization and Biological Activities of Trestatins A, B, And C", *The Journal of Antibiotics* XXXVI(9), pp. 1157–1165 (1983).

* cited by examiner

TREATMENT OF RUMEN ACIDOSIS WITH α-AMYLASE INHIBITORS

This application is a continuation of U.S. patent application Ser. No. 09/864,515, filed on May 24, 2001, now abandoned, which claims priority of U.K. Patent Application No. 0012793.6, filed on May 24, 2000, U.K. Patent Application No. 0012760.5, filed on May 24, 2000, U.K. Patent Application No. 0017495.3, filed on Jul. 17, 2000, and the benefit of U.S. patent application Ser. No. 60/218,494, filed on Jul. 14, 2000, U.S. patent application Ser. No. 60/218,326, filed on Jul. 14, 2000, and U.S. patent application Ser. No. 60/225,156, filed on Aug. 14, 2000.

The invention described herein relates to the treatment of rumen acidosis, especially chronic acidosis in ruminants, and related conditions.

Rumen acidosis is a well-documented metabolic disease of ruminants caused by over-consumption of readily fermentable carbohydrates, and problems associated with the condition have been known for many years: see Nordlund et al. 1995, Nagaraja et al. 1998, Owens et al. 1998 and Dirksen 1969. Acidosis can be divided into two forms: acute and chronic. We define acute acidosis as a rumen pH between pH 4.0 and 5.0 with elevated ruminal lactate, and chronic acidosis as a rumen pH between 5.0 and 5.5 with normal levels of lactate of up to 5 mM. The literature also refers to subacute acidosis, which has rumen pH values below 5.0 but in some cases is associated with high lactate levels and in others is not. We categorise the former case as mild acute acidosis, and the latter as chronic acidosis.

The main cause of acidosis is the consumption of a diet with a high content of readily fermentable carbohydrate and/or which is low in roughage. Chronic acidosis can occur when animals eat large quantities of readily fermentable diets and may occur at any stage in production, or indeed throughout the time that they are on the high concentrate diets. Acute acidosis can occur when a large increase in the amount of concentrate in the diet takes place, for example after calving or on transfer to the feedlot. However it can also occur following a disruption in normal feed intake patterns such as accidental presentation of excess feed or a fasting period followed by overeating. Reduced rumen pH can also be caused by a decrease in the proportion of crude fibre in the diet. The aetiology of acidosis is therefore based on the absolute intake of excessive quantities of carbohydrate and/or an unfavourable proportion of basic foodstuffs in the ration. The type of grain (high moisture corn is more acidosis-inducing than dry-rolled corn or sorghum) and the type of processing (steam flaked grain is particularly digestible) along with type and amount of roughage is important. Grains such as barley, wheat and high-moisture corn that have fast rates of ruminal starch digestion generally cause the most problems. For example barley, wheat flour, oats and steam flaked corn all have ruminal starch availability greater than 85%. Guidelines for diets for dairy cattle producing more than 35–40 kg of milk suggest neutral detergent fibre of 25–30% of the diet, with 75% of that from forage, non-structural carbohydrate levels of 35–40% and starch of 30–40% (Nocek 1997).

Acute acidosis is characterised by a precipitous decrease in ruminal pH with a high concentration of ruminal lactic acid (50–100 mM). The ruminal microbial population undergoes a significant shift, with an increase in gram-positive lactic-acid producing bacteria, specifically *Streptococcus bovis* and *Lactobacillus* species. The falling pH leads to the death of gram-negative bacteria and the reduction or complete disappearance of ciliated protozoa. The shift in the fermentation pattern to lactate production is associated with decreased volatile fatty acid (VFA) production. Systemic changes include decreased blood pH and bicarbonate and increased blood D and L-lactate. Acute acidosis can cause significant impairment of physiological functions such as ruminal stasis and dehydration, eventually leading to coma and death. Even if the animal survives, it may never completely recover.

Chronic acidosis has much more subtle clinical signs. The animals remain alert and consume feed, but may look 'off-colour'. The fall in rumen pH to below 5.5 is due to a general increase in fermentation within the rumen leading to greater production of VFAs. The increase of VFAs in the rumen is very highly correlated with increases in the blood, but blood pH does not change significantly. Total ciliated ruminal protozoa decline due to the falling pH, with species differences in rate, but do not disappear entirely. Total viable bacterial counts increase over time, including increased amylolytic bacteria. However the overwhelming rise in *S. bovis* and *Lactobacillus* species seen in acute acidosis does not occur. While the rate of lactate production rises transiently after feeding the lactate is utilised immediately in production of VFAs, and does not accumulate in the rumen. Specifically the symptoms of chronic acidosis are a fall in ruminal pH to 5.0–5.5 without significant lactic acid accumulation.

Summary of symptoms of acute and chronic acidosis

|  | Normal | Chronic acidosis | Acute acidosis |
| --- | --- | --- | --- |
| Rumen pH | >6.0 | 5.5–5.0 | <5.0 |
| VFAs | ~100 mM | up to 200 mM | reduced |
| lactate concentration | up to 5 mM | up to 5 mM | >50 mM |
| glucose | negligible | negligible | >10 mM |
| Protozoa |  | much reduced | dead |
| Bacteria |  | increased | increased *S. bovis* and *Lactobacillus* sp. |

Rumen acidosis is associated with many secondary conditions that can have a significant impact on livestock animal performance, i.e. reduction in the feed conversion to meat and/or milk. Milk quality can also suffer in association with acidosis. Irreversible damage to the ruminal epithelium occurs at a rumen pH below 5.5, causing hyperkeratosis, papillary clumping and rumenitis of the ruminal epithelium. The animals have reduced appetite and performance due to impaired nutrient absorption, resulting in reduced weight gain in beef cattle and decreased milk yield and quality in dairy cattle. Other effects are laminitis, intermittent diarrhoea, poor appetite and cyclic feed intake, a high herd cull rate for poorly defined health problems, poor body condition and abscesses without obvious causes. Chronic laminitis is one of the most consistent clinical signs, with ridges in the dorsal hoof wall, sole ulceration, white line lesions, sole haemorrhages and misshapen hooves. On average, farmers report that 25% of animals in UK dairy herds are lame, and the true incidence of chronic laminitis is likely to be higher as it does not always produce detectable lameness. Liver abscesses are known to be linked with acidosis, and in most feedlots the incidence of liver abscesses averages from 12% to 32% of slaughtered cattle, and is a major cause of liver condemnation. Liver abscesses are not necessarily diagnosed while the animal is alive, but have a deleterious effect on their performance and general health. Animals may also have depressed immune function, a high incidence of respiratory diseases and reduced fertility rates. Most dairy herds with a chronic acidosis problem have an annual herd turnover rate of greater than 45%, or an annual cull rate greater than 31%. The reasons for culling are usually poorly defined. (Nocek 1997, Nordlund 1995, Nagaraja 1998, Stock and Britten 1998, AnimalPharm 1999, Kay 1969, McManus 1977).

Another problem which can be seen with high-yielding dairy cows fed with a high carbohydrate and/or low roughage diet is the acidosis-related "low milk fat syndrome". As the pH in the rumen falls, the pattern of fermentation shifts towards producing more propionate and less acetate and butyrate. As approximately half of milk fat is produced from acetate and butyrate, this results in a drop in the milk fat content. (A T Chamberlain & J M Wilkinson, Feeding the Dairy Cow, Chalcombe Publications, UK, 1996).

Rumen acidosis and related problems are estimated to cost the livestock industry more than $1 billion per annum due to lost performance.

Recommended treatments for acute acidosis include administration of a mixture of sodium bicarbonate, formaldehyde, magnesium oxide and charcoal to kill rapidly dividing bacteria. (NebGuide G91-1047-A). Buffers are widely used (Horn 1979, Kennelly 1999), but do not seem efficacious enough to satisfy the livestock industry. Palatability of most buffers is low, and requires careful management to avoid reduced feed intake. Ionophore antibiotics such as monensin, lasalocid and salinomycin are generally effective against gram-positive bacteria, including the major ruminal lactate-producing bacteria, *S. bovis* and *Lactobacillus* species (Burrin and Britton 1986, Coe 1999, Nagaraja 1985). They are therefore effective at preventing acute acidosis on transfer to high concentrate diets when cattle first reach the feedlot or following calving. They also act to reduce total VFA production in cattle with chronic acidosis, and therefore stabilise rumen pH. However ionophores also decrease food intake. Other antibiotic classes have also been shown to prevent or ameliorate acute acidosis, including virginiamycin in sheep (Thorniley et al 1998), and the sulphur-containing peptide antibiotic thiopeptin, which is particularly effective against *S. bovis* (Armstrong 1984). However, sustained use of antibiotic feed additives is no longer seen as an appropriate management tool (for review see: The use of drugs in food animals: benefits and risks, 1999). Probiotic control has been demonstrated with a number of species, including *Selenomonas ruminantium* subsp. *lactolytica* strain JDB201 (Wiryawan et al 1995), the lactate utlilizer *Megasphaera elsedenii* (Das, Kung and Hession 1995), and in more general terms patent WO 96/17525. The latter also claims enzymes that increase degradation of starch or fibre. Other proposed, but not commercialised, treatments include use of bacteriocins (Teather and Forster 1998), and the economically unviable manipulation of ruminal fermentation with organic acids (Martin, 1988, Martin et al. 1999).

Armstrong, D. G. Antibiotics as feed additives for ruminant livestock in 'Antimicrobials and Agriculture The proceedings of the 4$^{th}$ International symposium on antibiotics in agriculture: benefits and malefits', 1984 ed. Woodbine M. Butterworths ISBN 0 408 11155 0

Das, N. K. *Ruminant feed additive* Patent application US 76-748210 761207

Kennelly, J. J., Robinson, B. and Khorasani, G. R. *Influence of carbohydrate source and buffer on rumen fermentation characteristics, milk yield, and milk composition in early-lactation Holstein cows* Journal of Dairy Science 1999 82: 2486–2496

Kung, L. and Hession, A. O. *Preventing in vitro lactate accumulation in ruminal fermentations by inoculation with Megasphaera elsedenii* Journal of Animal Science 1995 73: 250–256

Martin, S. A. *Manipulation of ruminal fermentation with organic acids: a review* Journal of Animal Science 1998 76: 3123–3132

Martin, S. A., Streeter, M. N., Nisbet, D. J., Hill, G. M. and Williams, S. E. *Effects of DL-Malate on ruminal metabolism and performance of cattle fed a high-concentrate diet* Journal of Animal Science 1999 77: 1008–1015

Teather, R. M. and Forster, R. J. *Manipulating the rumen microflora with bacteriocins to improve ruminant production* Canadian Journal of Animal Science 1998 78 (Supplement): 57–69.

The use of drugs in food animals: benefits and risks CABI publishing 1999 ISBN 0 85199 371 0

Thorniley, G. R., Rowe, J. B., Cowcher, P. C., Boyce, M. D. *A single drench of virginiamycin to increase safety of feeding grain to sheep* Australian Journal of Agricultural Research 1998 49 (5): 899–906

Wiryawan, K. G. and Brooker, J. D. *Probiotic control of lactate accumulation in acutely grain-fed sheep* Australian Journal of Agricultural Research 1995 46 (8):1555–68

Kay, M., Fell, B. F. and Boyne, R. The relationship between the acidity of the rumen contents and rumenitis in calves fed on barley Research in Veterinary Science 1969 10 181–187

McManus, W. R., Lee, G. J. and Robinson, V. N. E. Microlesions on rumen papillae of sheep fed diets of wheat grain Research in Veterinary Science 1977 22: 135–137

Further References

1. Lameness costs UK dairy herds, says NMR AnimalPharm 417 Mar. 26$^{th}$ 1999 p6
2. Burring, D. G. and Britton, R. A. Response to monensin in cattle during subacute acidosis Journal of Animal Science 1986 63:888–893
3. Coe, M. L., Nagaraja, T. G., Sun, Y. D., Wallace, N. Towne, E. G., Kemp, K. E. and Hutcheson, J. P. Effect of Virginiamycin on ruminal fermentation in cattle during adaptation to a high concentrate diet and during an induced acidosis Journal of Animal Science 1999 77:2259–2268
4. Dirksen, G. Acidosis in Physiology of Digestion and Metabolism in the Ruminant: Proceedings of the Third International Symposium, Cambridge, England: August 1969 Ed. A. T. Phillipson, Oriel Press IBSN 0 85362 053 9
5. Nagaraja, T. G. Galyean, M. L. and Cole, N. A. Nutrition and Disease Veterinary Clinics of North America: Food Animal Practice 1998 14 (2) 257–277
6. Nagaraja, T. G., Avery, T. B., Galitzer, S. J. and Harmon, D. L. Effect of ionophore antibiotics on experimentially induced lactic acidosis in cattle American Journal of Veterinary Research 1985 46 (12) 2444–2452
7. Nocek, J. E. Bovine acidosis: Implications on laminitis Journal of Dairy Science 1997 80:1005–1028
8. Nordlund, K. V. Garrett, E. F. Oetzel, G. R Herd-based rumenocentesis: a clinical approach to the diagnosis of subacute rumen acidosis. Compendium on Continuing Education for the Practicing Veterinarian. 1995. 17: 8, Supplement, S48–S56
9. Owens, F. N. Secrist, D. S. Hill, W. J. and Gill D. R. Acidosis in cattle: a review Journal of Animal Science 1998 76:275–286
10. University of Nebraska, Lincoln NebGuide G91-1047-A http:/www.inar.unl.edu/pubs/AnimalDisease/g1047. htm There is a general need for a safe effective treatment for rumen acidosis;

especially chronic and/or acute rumen acidosis;
especially in ruminants such as cattle and sheep;
especially in lactating ruminants such as cattle and sheep;
which can preferably be administered easily, such as with food or drink;
which preferably is non-antimicrobial;
preferably which is palatable to the animal;
preferably which is active only in the rumen and has no systemic effects;

which preferably does not present any residues in meat and/or milk, and which preferably does not require a withholding period;

which is preferably non-toxic to animal and feed handlers (manufacturer and farmer);

and/or which preferably can stabilise the rumen fermentation, thus preventing excessive reductions in pH and maintaining VFA proportions such that milk fat production is not adversely affected.

We have discovered that certain inhibitors of bacterial α-amylase and/or α-glucosidase can be used to reduce ruminal pH in an effective way which should be useful in the treatment of both chronic and acute acidosis and related conditions.

By "inhibitor" herein is meant individual agents and mixtures of agents which have inhibitory activity, including fermentation broth products mentioned below.

Preferably the inhibitor of bacterial α-amylase and/or α-glucosidase has an $IC_{50}$ of $10^{-3}$M or less, more preferably $10^{-4}$M or less, yet more preferably $10^{-5}$M or less, in the rumen amylase and glucosidase screens described herein.

Preferably the amylase and/or α-glucosidase inhibitor has low antimicrobial activity, more preferably with a MIC value of more than 50 μg/ml in the tests described herein, yet more preferably more than 100 μg/ml.

A preferred group of α-amylase and/or α-glucosidase inhibitors include the substances disclosed below and simple analogues thereof, including in the Examples below, which are found to be effective in the screens mentioned below (NB All references mentioned herein are hereby incorporated in their entirety):

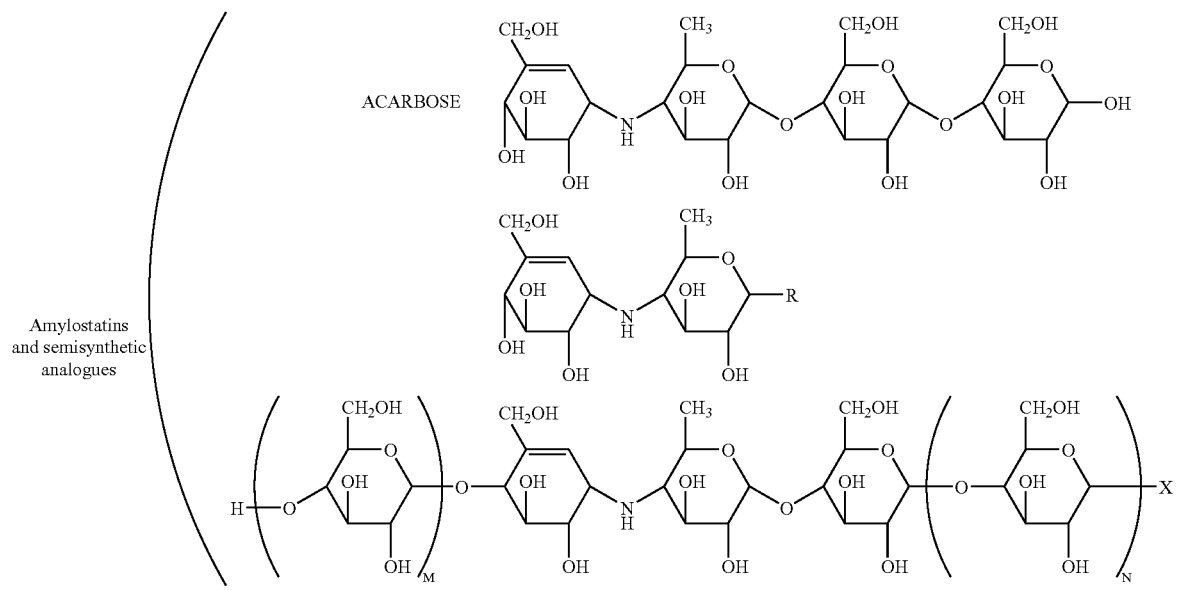

One aspect of the invention is the use of an effective inhibitor of bacterial α-amylase and/or α-glucosidase in the manufacture of a composition for the treatment of acidosis. Of particular interest are inhibitors of amylases/glucosidases present in ruminal bacteria, such as those mentioned hereinafter.

A further aspect of the invention is a method of treatment of acidosis which comprises administration of an effective amount of an inhibitor of bacterial α-amylase and/or α-glucosidase to an animal.

A further aspect of the invention is a formulation suitable for the treatment of acidosis in an animal which comprises an inhibitor of bacterial α-amylase and/or α-glucosidase.

Further aspects of the invention are as defined in the claims.

defined as "acarbose and higher homologues."*

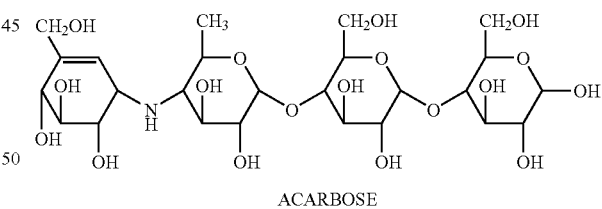

Compound disclosed specifically in DE-2347782. The following are homologues of acarbose:

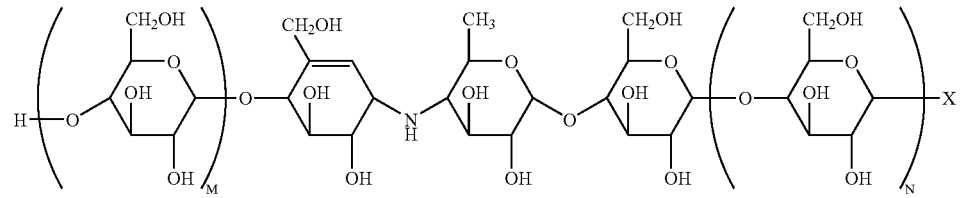

These specific compounds are disclosed in GB-1,482,543, wherein:

| X | M | N | GB-1,482,543 ref |
|---|---|---|---|
| OH | 0 | 0 | Component II |
| OH | 0 | 1 | Component III |
| OH | 0 | 2 | Component IV |
| OH | 0 | 3 | Component V |
| OH | 0 | 4 | Component VI |
| OH | 0 | 5 | Component VII |
| OH | 0 | 6 | Component VIII |

These specific compounds are disclosed in *Agric. Biol. Chem.*, 46 (7), 1941–1945, 1982, wherein:

| X | M | N | Agr. Biol. Chem ref |
|---|---|---|---|
| OH | 0 | 0 | Component 1 |
| OH | 0 | 1 | Component 2 |
| OH | 0 | 2 | Component 3 |
| OH | 1 | 0 | Component 4 |
| OH | 1 | 1 | Component 5 |
| OH | 1 | 2 | Component 6 |

The following semi-synthetic acarbose analogues, generically and specifically disclosed in U.S. Pat. No. 4,175,123

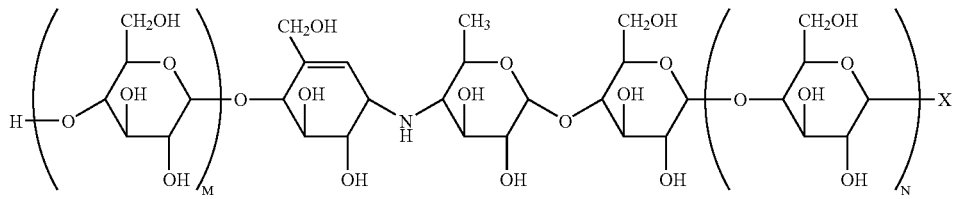

wherein M=0 to 8, and the sum of M+N is 0 to 7; X is OR, SH, SR, $NH_2$, NHR, or $NRR^1$, where R is alkyl, alkenyl, cycloalkyl, aralkyl, aryl or heterocyclyl wherein:

alkyl is preferably straight-chain or branched alkyl with 1 to 30, especially 1 to 18, carbon atoms (e.g. methyl, ethyl, n-propyl, 1-propyl, n-butyl, t-butyl, n-hexyl, n-octyl, octyl-2, dodecyl, lauryl, cetyl and stearyl), wherein the alkyl radicals R can carry one or more, preferably 1 to 5, identical or different substituents (e.g., hydroxyl, or alkoxy, with preferably 1 to 4 carbon atoms, methoxy and ethoxy; amino or monoalkylamino and dialkylamino, with preferably 1 to 4 carbon atoms per alkyl radical, monomethylamino, monoethylamino, dimethylamino, and diethylamino; mercapto or alkylthio, with preferably 1 to 4 carbon atoms, methylthio and ethylthio; halogen (preferably fluorine, chlorine and bromine); alkylcarbonyl, with preferably 1 to 4 carbon atoms in the alkyl radical; and carboxyl, nitro, cyano, the aldehyde group and the sulphonic acid group;

alkenyl is preferably straight-chain or branched alkenyl with 2 to 6 carbon atoms, with optional substituents (e.g. hydroxyl, alkoxy with 1 to 4 carbon atoms, mercapto, alkylthio with 1 to 4 carbon atoms, halogen (preferably fluorine, chlorine and bromine) or nitro);

cycloalkyl, preferably a carbocyclic radical with 3 to 7 ring carbon atoms (preferably 5 to 7 ring carbon atoms), which can be substituted, (e.g. the groups and atoms mentioned above in the case of open-chain hydrocarbon radicals R);

aryl is preferably a monocyclic or bicyclic aromatic radical with 6 to 10 carbon atoms in the aryl part (e.g. phenyl, biphenyl, naphthyl, etc., in particular phenyl, which can be substituted), optionally substituted aryl or aralkyl radicals, preferably 1 to 3 identical or different substituents (e.g. alkyl with 1 to 10 carbon atoms, optionally substituted, (e.g. chlorine, nitro or cyano); optionally substituted alkenyl radicals with 1 to 10 carbon atoms; hydroxyl or alkoxy with preferably 1 to 4 carbon atoms; amino or monoalkylamino and dialkylamino with preferably 1 to 4 carbon atoms per alkyl radical: mercapto or alkylthio with preferably 1 to 4 carbon atoms; and carboxyl or carbalkoxy with preferably 1 to 4 carbon atoms; the sulphonic acid group, alkylsulphonyl with preferably 1 to 4 carbon atoms and arylsulphonyl, preferably phenylsulphonyl; aminosulphonyl or alkylaminosulphonyl and dialkylaminosulphonyl with 1 to 4 carbon atoms per alkyl group, preferably methylaminosulphonyl and dimethylaminosulphonyi; nitro, cyano or the aldehyde group; alkylcarbonylamino with preferably 1 to 4 carbon atoms; and alkylcarbonyl with 1 to 4 carbon atoms, benzoyl, benzylcarbonyl and phenethylcarbonyl, the last-mentioned alkyl; phenyl, benzyl and phenethyl radicals may be optionally substituted (e.g. chlorine, nitro or hydroxyl, as well as radicals derived from sugars);

aralkyl preferably has 6 to 10, especially 6, carbon atoms in the aryl part said aryl part being preferably monocyclic or bicyclic carbocyclic aryl, such as phenyl, biphenyl or naphthyl, and preferably 1 to 4, especially 1 or 2, carbon atoms in the alkyl part, as for example in benzyl or phenylethyl. Possible substituents for the aryl part of the aralkyl radical are preferably those substituents mentioned for the aryl radicals R above;

Heterocyclyl preferably has a hetero-paraffinic, heteroaromatic or hetero-olefinic 5-membered or 6-membered ring, with preferably 1 to 3 identical or different hetero-atoms (e.g. oxygen, sulphur or nitrogen), optionally substituted (e.g. hydroxyl, amino, $C_1$–$C_4$-alkyl groups, benzene nuclei or further, preferably 6-membered, heterocyclic rings of the type mentioned can be fused to them, wherein the bonding of the heterocyclic radical R is effected via a carbon atom of the heterocyclic system or of the fused benzene nucleus (preferred heterocyclic radicals are derived, e.g., from furan, pyran, pyrrolidine, piperidine, pyrazole, imidazole, pyrimidine, pyridazine, pyrazine, triazine, pyrrole, pyridine, benzimidazole, quinoline, isoquinoline or purine, including those heterocycles which are bonded via a —$CH_2$— bridge outside the ring, for example the furfuryl radical));

wherein $R_1$ of $NRR^1$, is alkyl, cycloalkyl, aralkyl, or aryl in which $R_1$ preferably represents a straight-chain or branched alkyl radical with 1–6 carbon atoms or a cycloalkyl, aralkyl or aryl radical as defined above for R (e.g. cyclopentyl, cyclohexyl, benzyl or phenyl radical), it being possible for the radicals mentioned to be preferably substituted by alkoxy with 1 to 4 carbon atoms, amino, $C_1$–$C_4$ monoalkylamino and $C_1$–$C_4$-dialkylamino, nitro, cyano, hydroxyl, mercapto, $C_1$–$C_4$-thioalkyl or the carboxyl or sulphonic acid group, in the case where $R_1$ denotes phenyl, also by $C_1$-$C_4$-alkyl;

wherein R and $R_1$ and the nitrogen atom to which they are bonded, may optionally form a heterocyclic ring, optionally saturated or unsaturated, the ring optionally containing 1 to 3 further (preferably 1) oxygen atoms, sulphur atoms or nitrogen atoms and, as hetero groups, a $SO_2$ group or a N-alkyl group, the alkyl (e.g. methyl, ethyl, n- and i-propyl and n-, l- and t-butyl) in the N-alkyl group preferably containing 1–4, in particular 1 or 2, carbon atoms;

wherein the heterocyclic ring contains 5–7, preferably 5 or 6, ring members. The 6-membered heterocyclic ring preferably contains the hetero-atom or the hetero-group in the para-position relative to the nitrogen atom (e.g. pyrrolidine, piperidine, hexamethleneimine, morpholine and N-methylpiperazine).

J. Antibiotics 36 p1157–1165 (1983) discloses the fermentation and isolation of a family of amylase inhibitors, trestatin-A, B and C. J. Antibiotics 36 p1166–1175 (1983) discloses the structures of trestatin-A, B and C Chem. Pharm. Bull 47(2), 187–193 (1999) describes the synthesis of the following N-containing maltooligosaccharides with α-amylase activity.

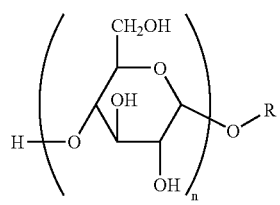

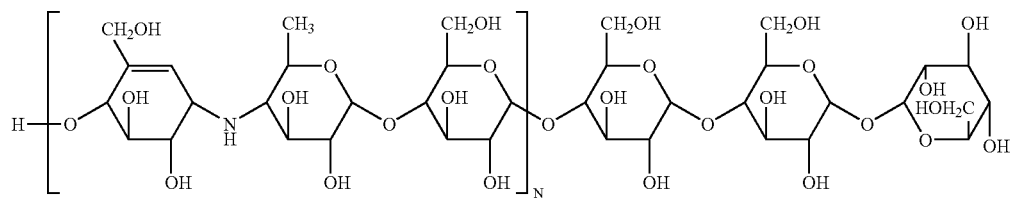

Trestatin A, N = 2
Treatatin B, N = 1
Trestatin C, N = 3

J. Antibiotics 37 p182–186 (1984) describes the isolation, characterisation and structure elucidation of higher homologues of the trestatins. The structures disclosed are:

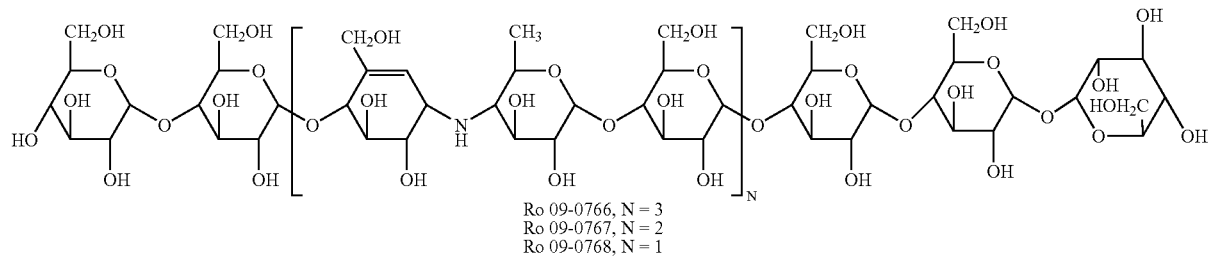

Ro 09-0766, N = 3
Ro 09-0767, N = 2
Ro 09-0768, N = 1

The amylase inhibitor, V-1532, is prepared and characterised as described in J. Mol. Biol. 260, 409–421, (1996).

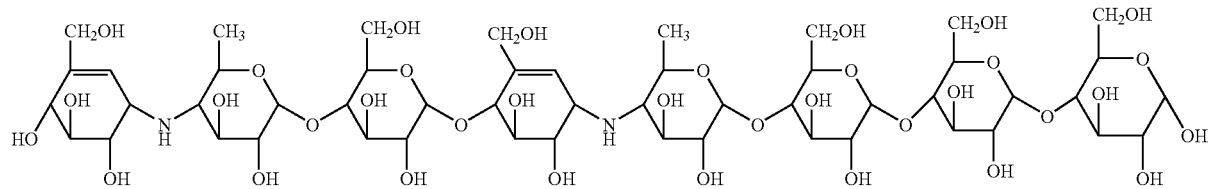

V-1532

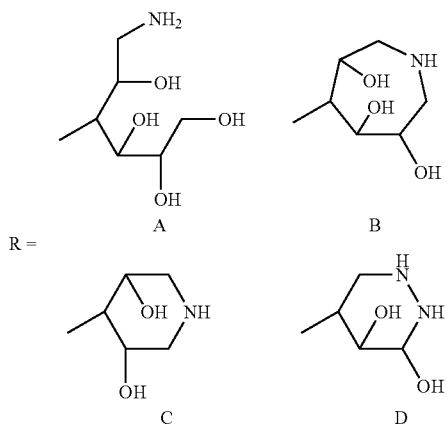

| R | n | Chem. Pharm Bull Ref. Number |
|---|---|---|
| A | 0 | Compound 6 |
| A | 1 | Compound 7 |
| A | 2 | Compound 8 |
| A | 3 | Compound 9 |
| A | 4 | Compound 10 |
| B | 0 | Compound 11 |
| B | 1 | Compound 12 |
| B | 2 | Compound 13 |
| B | 3 | Compound 14 |
| B | 4 | Compound 15 |
| C | 0 | Compound 16 |
| C | 1 | Compound 17 |
| C | 2 | Compound 18 |
| C | 3 | Compound 19 |
| C | 4 | Compound 20 |
| D | 1 | Compound 22 |
| D | 2 | Compound 23 |
| D | 3 | Compound 24 |

Agric. Biol. Chem, 41(11) 2221–2228 (1977) describes the fermentation, recovery and isolation of the microbial natural product amylase inhibitor, SA-1. Although the structure of SA-1 is unknown, the compound has been shown to be homogeneous by tlc and is characterised by analytical data.

Kor. J. Mycol. Vol 13, No. 4, 203–212, (1985) describes the fermentation and purification of a microbial natural product □-amylase inhibitor from culture filtrates of *Streptomyces* strain DMC-72. The compound is characterised by analytical data.

EP-194794 (WO-8605094 PCT equivalent) reports the structures of a number of N-substituted valiolamine derivatives, referring to EP-56194 for their synthesis. The compounds have the structure:

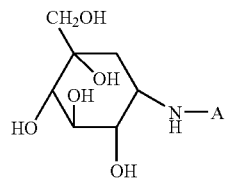

in which A is an acyclic hydrocarbon group of 1 to 10 carbon atoms which may have one or more members selected from the group consisting of hydroxy, phenoxy, thienyl, furyl, pyridyl, cyclohexyl, and a substituted or unsubstituted phenyl; a five- to six-membered cyclic hydrocarbon group which may have one or more members selected from the group consisting of hydroxy, hydroxymethyl, methyl and amino, or a saccharide residue.

ES-8800955 describes valiolamine and validamine analogues with the structures:

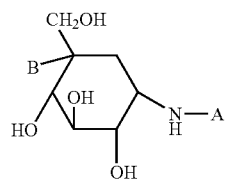

in which A is a hydrocarbon group of 1 to 10 carbon atoms, optionally substituted with hydroxy, phenoxy, thienyl, furyl, pyridyl, cyclohexyl; or a phenyl group optionally substituted; or a cyclic hydrocarbon of 3–7 carbon atoms, optionally substituted with hydroxyl, and B is hydrogen or hydroxyl.

EP-301 400 (US equivalent—U.S. Pat. No. 4,885,361) describes the sulphation of the trestatins to give sulphated oligosaccharides with structures:

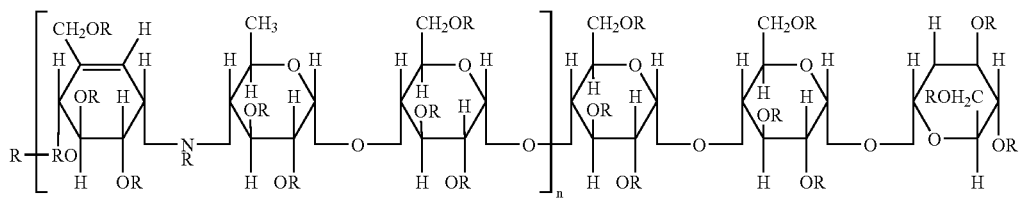

wherein n is a whole number from 1–3; R is hydrogen or a residue —SO$_3$M and M is a cation; and in which the degree of sulphation is at least 1.

EP-173950 describes the fermentation, recovery and isolation of the pseudooligosaccharide α-glycosidase inhibitor from *Streptomyces* sp. FH-1717 (DSM-3006). This compound has the structure shown:

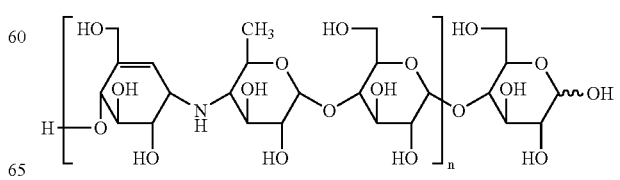

EP-49981 discloses the synthesis of some N-substituted valienamine derivatives:

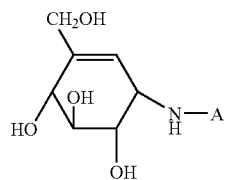

in which A is a chain hydrocarbon group having 1 to 10 carbon atoms optionally substituted by hydroxyl, phenoxy, thienyl, furyl, pyridyl, cyclohexyl or phenyl optionally substituted by hydroxyl, lower alkoxy, lower alkyl, halogen or carboxyl; or a cyclic hydrocarbon group having 3 to 7 carbon atoms optionally substituted by hydroxyl.

Angewandte Chemie Int. Ed. 20, 744–761 (1981) reviews the chemistry of microbial derived α-glucosidase inhibitors. The oligosaccharides are described elsewhere in this specification. The properties of the low molecular weight inhibitors, nojirimycin and 1-deoxynojirimycin, are reported.

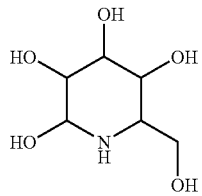
nojirimycin

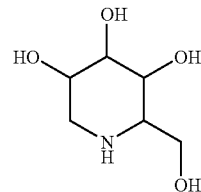
1-deoxynojirimycin

The fermentation, recovery, resin and HPLC purification, and nmr assignment of an oligosaccharide amylase inhibitor from *Streptomyces conglobatus*, ATCC-31005 is described in Example 7 of the Experimental section of this specification.

The fermentation, recovery, resin and HPLC purification, and nmr assignment of a novel oligosaccharide amylase inhibitor from *Streptomyces conglobatus*, ATCC-31005 is described in Example 8 of the Experimental section of this specification.

Tetrahedron Letters, 37, 14, 2479–2482 (1996) describes the synthesis of β-acarbose from 1-epivalienamine.

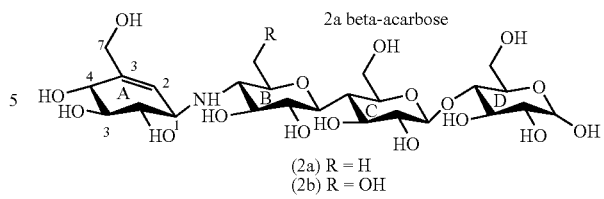

(2a) R = H
(2b) R = OH

Both isoacarbose and acarviosine-glucose can be produced by the enzymic transformation of acarbose, as reported in Archives Biochem. Biophys, 371, 2, 277–283 (1999).

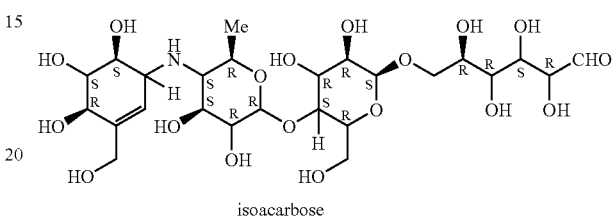
isoacarbose

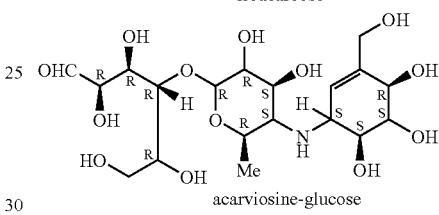
acarviosine-glucose

The synthesis of adiposin-2 is reported in JCS Chem. Comm., 9, 605–606 (1988)

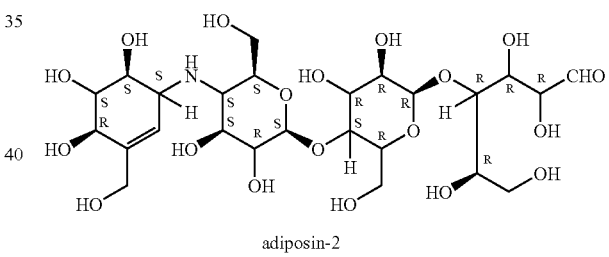
adiposin-2

---

Derivatives of the above compounds transformed as follows:

1. All above compounds with a valieneamine moiety can be transformed into the saturated analogue, produced by a reduction process described for example in EP-67356

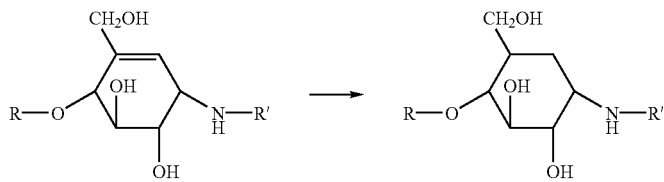

2. The chain extended, viz.: see EP-240175-A

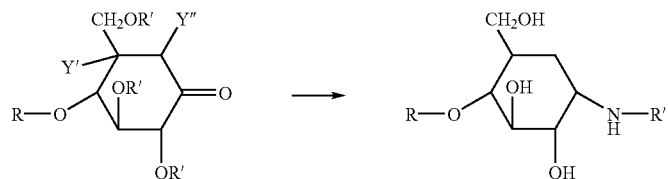

where Y' = OH, Y" = H;
or Y' = Y" = H;
or Y' + Y" = a bond

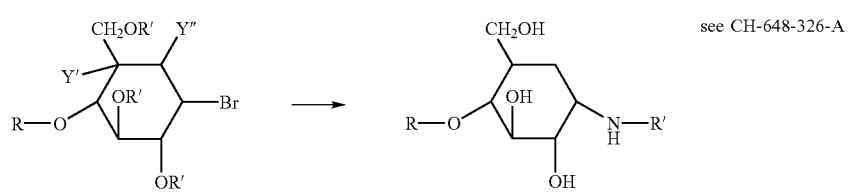

see CH-648-326-A where Y' = OH, Y" = H;
or Y' = Y" = H;
or Y' + Y" = a bond

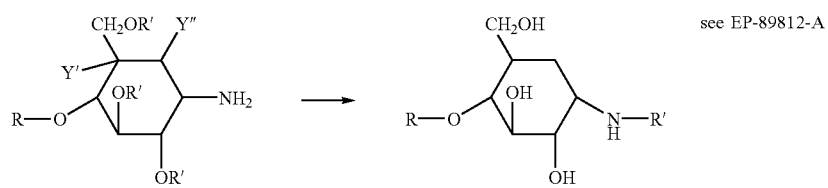

see EP-89812-A where Y' = OH, Y" = H;
or Y' = Y" = H;
or Y' + Y" = a bond

Other derivatives incorporating the the valineamine core moiety, and of all compounds mentioned above, specifically acarbose, higher homologues thereof, trestatins, and V-1532, and the valeineamine compounds given by their registry numbers below* can be made by methods described herein.

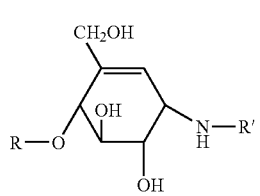

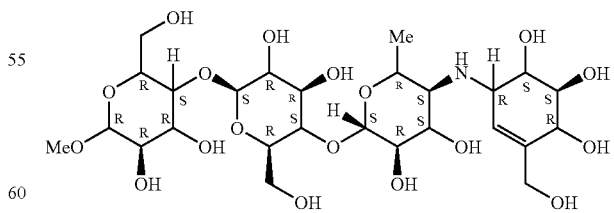

RN 257941-10-9 certain compounds with the moiety shown above appear in Chemical Abstracts* with the Registry Numbers (RN) shown below.

Stick, Robert V.; Tilbrook, D. Matthew G.; Williams, Spencer J. Australian Journal of Chemistry (1999), 52(9), 895–904. p896.

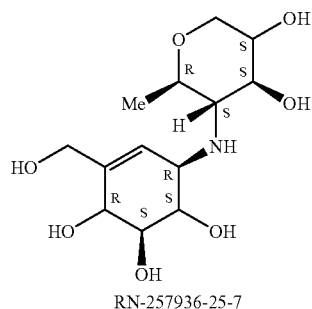

RN-257936-25-7

Stick, Robert V.; Tilbrook, D. Matthew G.; Williams, Spencer J. Australian Journal of Chemistry (1999), 52(9), 895–904 p896.

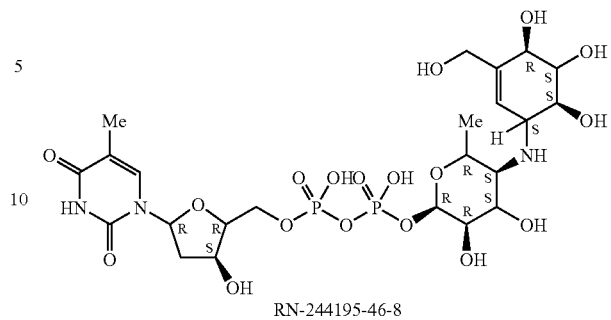

RN-244195-46-8

Mahmud, Taifo; Tornus, Ingo; Egelkrout, Erin; Wolf, Eckardt; Uy, Charmaine; Floss, Heinz G.; Lee, Sungsook. Journal of the American Chemical Society (1999), 121(30), 6973–6983.

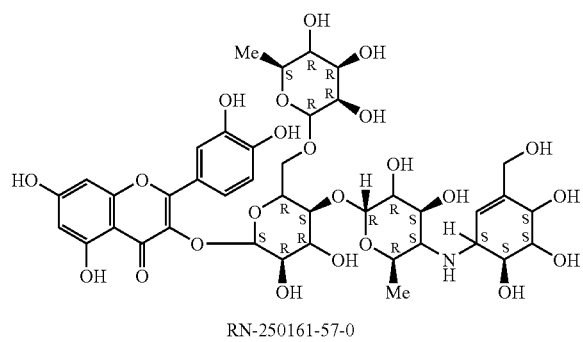

RN-250161-57-0

Crueger, Anneliese; Doerschug, Michael; Heiker, Fred-Robert; Von Hugo, Hasso; Rauenbusch, Erich. DE-19821038-A1 p2.

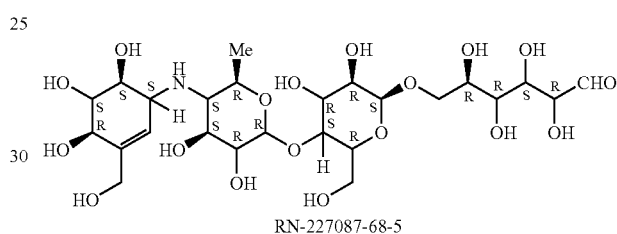

RN-227087-68-5

Park, Kwan Hwa; Kim, Myo Jeong; Lee, Hee Seob; Han, Nam Soo; Kim, Doman; Robyt, John F. Carbohydrate Research (1998), 313(3–4), 235–246.

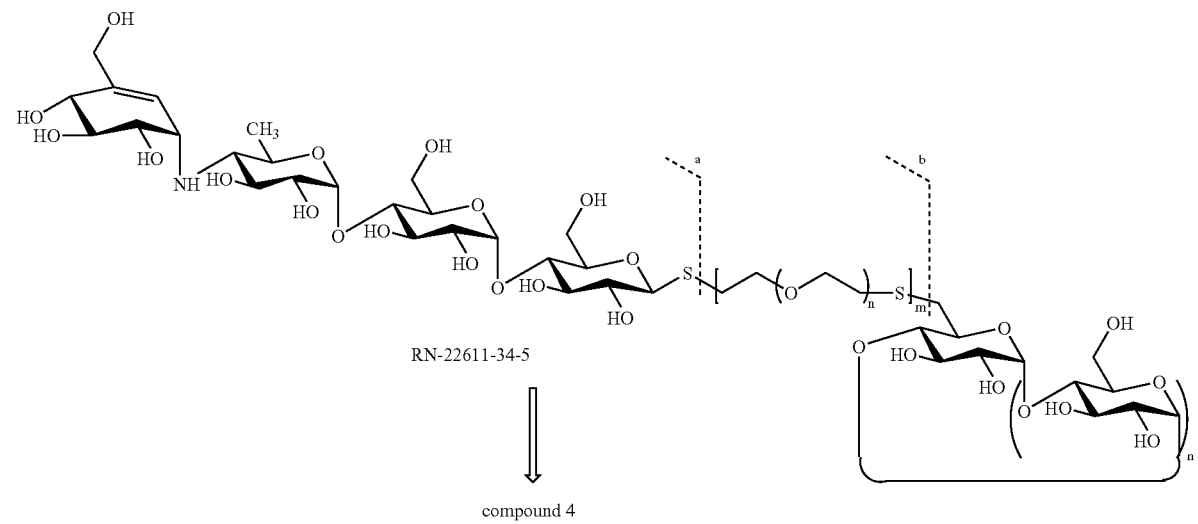

RN-22611-34-5 compound 4

1 m = 0
2 m = 1, n = 2
3 m = 2, n = 3
4 m = 4, n = 3

Payre, Nathalie; Cottaz, Sylvain; Boisset, Claire; Borsali, Redouane; Svensson, Birte; Henrissat, Bernard; Driguez, Hugues. Angewandte Chemie, International Edition (1999), 38(7), 974–977. p975.

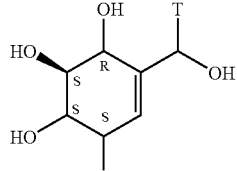

RN-223608-57-9

Lee, Sungsook; Tornus, Ingo; Dong, Haijun; Groger, Stefan. Journal of Labelled Compounds & Radiopharmaceuticals (1999), 42(4), 361–372 p363.

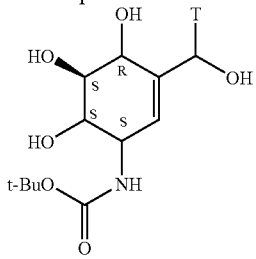

RN-223608-52-4

Lee, Sungsook; Tornus, Ingo; Dong, Haijun; Groger, Stefan. Journal of Labelled Compounds & Radiopharmaceuticals (1999), 42(4), 361–372 p363.

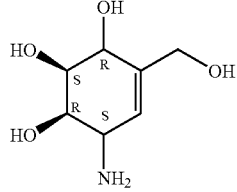

RN-22137-17-1

Shing, Tony K. M.; Li, Tin Y.; Kok, Stanton H.-L. Department of Chemistry, The Chinese University of Hong Kong, Shatin, Peop. Rep. China. Journal of Organic Chemistry (1999), 64(6), 1941–1946. compound 2 p1942.

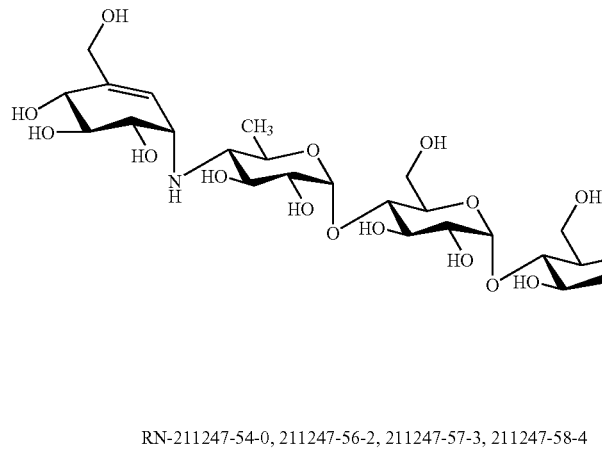

RN-211247-54-0, 211247-56-2, 211247-57-3, 211247-58-4

L0 = 211247-54-0
L14 = 211247-56-2
L36 = 211247-57-3
L73 = 211247-58-4

Sigurskjold, Bent W.; Christensen, Trine; Payre, Nathalie; Cottaz, Sylvain; Driguez, Hugues; Svensson, Birte. Biochemistry (1998), 37(29), 10446–10452. structure referenced on page 10448.

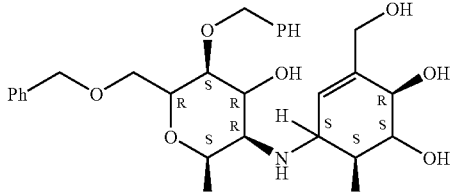

RN-211239-26-8

Ogawa, Seiichiro; Ashiura, Makoto; Uchida, Chikara. Carbohydrate Research (1998), 307(1,2), 83–95. compound 37 p88.

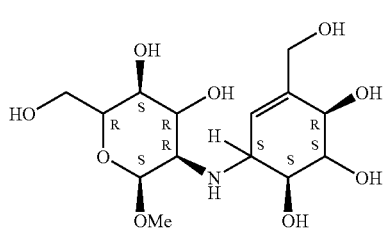

RN-211237-50-2

Ogawa, Seiichiro; Ashiura, Makoto; Uchida, Chikara. Carbohydrate Research (1998), 307(1,2), 83–95. compound 5 p88.

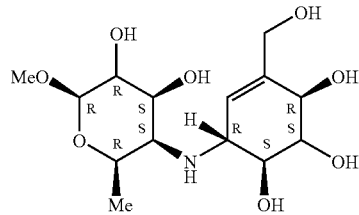

RN-207681-89-8

McAuliffe, Joseph C.; Stick, Robert V.; Matthew, D.; Tilbrook, G.; Watts, Andrew G. Department of Chemistry, The University of Western Australia, Nedlands, Australia.-

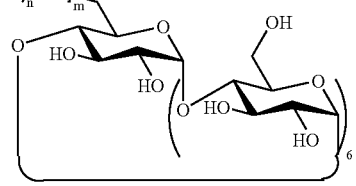

| m | n |
|---|---|
| L0  | 0 |
| L14 2 | 1 |
| L36 3 | 2 |
| L73 3 | 3 |

Australian Journal of Chemistry (1998), 51(2), 91–95. compound 3 p91.

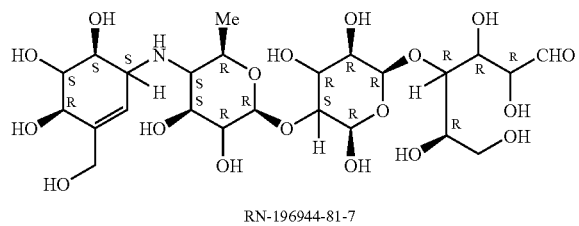

RN-196944-81-7

Crueger, Anneliese; Dellweg, Hans-Georg; Lenz, Juergen Georg; Schroeder, Werner; Pape, Hermann; Goeke, Klaus; Schaper, Beate; Hemker, Michael; Piepersberg, Wolfgang; Distler, Juergen; Stratmann, Ansgar. EP-796915-A2 p13.

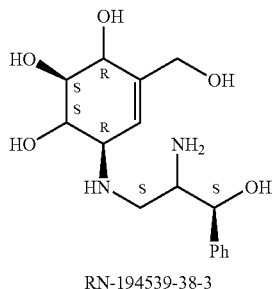

RN-194539-38-3

Ogawa, Seiichiro; Mito, Tamami; Taiji, Eiichi; Jimbo, Masayuki; Yamagishi, Kiwamu; Inokuchi, Jin-Ichi. Bioorganic & Medicinal Chemistry Letters (1997), 7(14), 1915–1920. compound 16b p1917.

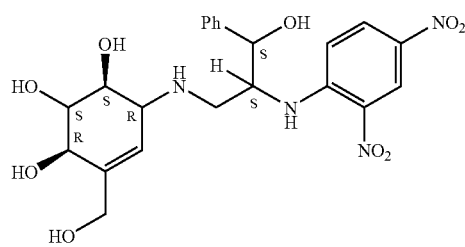

RN-194539-37-2

Ogawa, Seiichiro; Mito, Tamami; Taiji, Eiichi; Jimbo, Masayuki; Yamagishi, Kiwamu; Inokuchi, Jin-Ichi. Bioorganic & Medicinal Chemistry Letters (1997), 7(14). 1915–1920. compound 15b p1917.

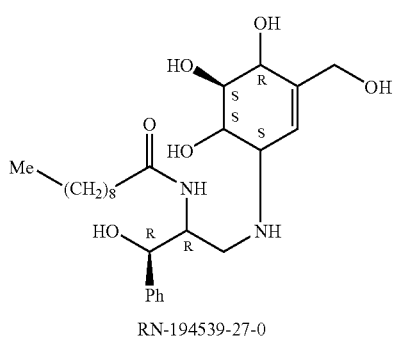

RN-194539-27-0

Ogawa, Seiichiro; Mito, Tamami; Taiji, Eiichi; Jimbo, Masayuki; Yamagishi, Kiwamu; Inokuchi, Jin-Ichi. Bioorganic & Medicinal Chemistry Letters (1997), 7(14), 1915–1920. compound 6a p1916.

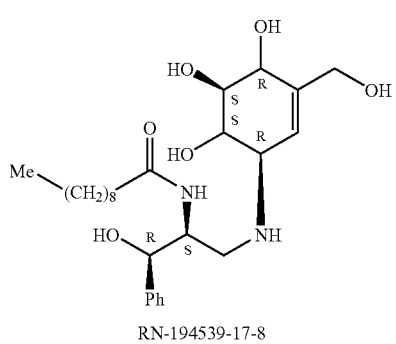

RN-194539-17-8

Ogawa, Seiichiro; Mito, Tamami; Taiji, Eiichi; Jimbo, Masayuki; Yamagishi, Kiwamu; Inokuchi, Jin-Ichi. Bioorganic & Medicinal Chemistry Letters (1997), 7(14), compound 4d p1916.

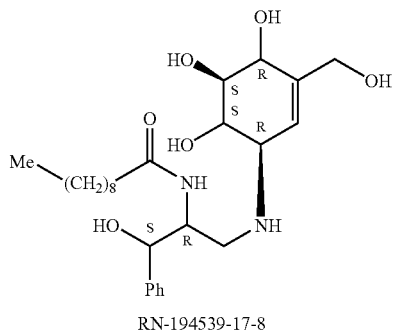

RN-194539-17-8

Ogawa, Seiichiro; Mito, Tamami; Taiji, Eiichi; Jimbo, Masayuki; Yamagishi, Kiwamu; Inokuchi, Jin-Ichi. Bioorganic & Medicinal Chemistry Letters (1997), 7(14), compound 4c p1916.

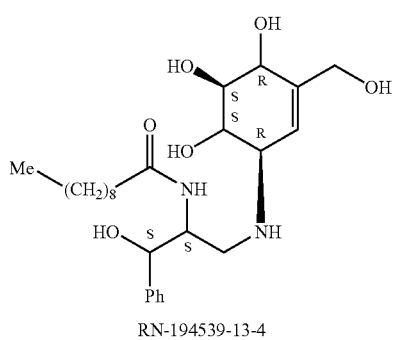

RN-194539-13-4

Ogawa, Seiichiro; Mito, Tamami; Taiji, Eiichi; Jimbo, Masayuki; Yamagishi, Kiwamu; Inokuchi, Jin-Ichi. Bioorganic & Medicinal Chemistry Letters (1997), 7(14), compound 4b p1916.

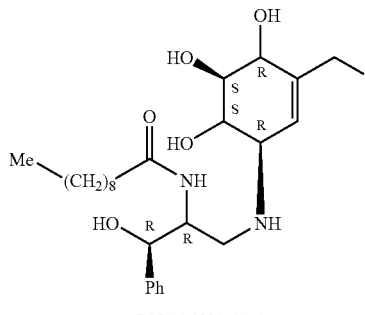

RN-194539-11-2

Ogawa, Seiichiro; Mito, Tamami; Taiji, Eiichi; Jimbo, Masayuki; Yamagishi, Kiwamu; Inokuchi, Jin-Ichi. Bioorganic & Medicinal Chemistry Letters (1997), 7(14), compound 4a p1916.

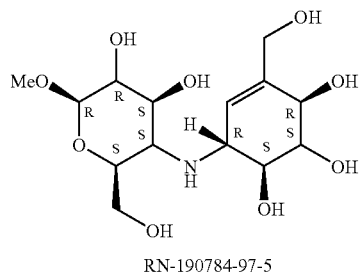

RN-190784-97-5

McAuliffe, Joseph C.; Stick, Robert V. Australian Journal of Chemistry (1997), 50(3), 219–224 compound 27 p220.

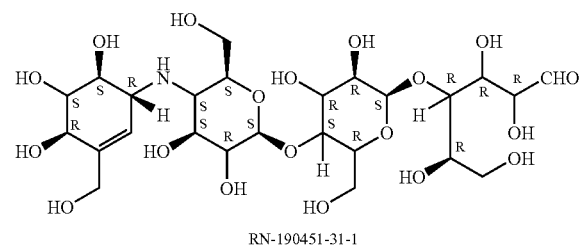

RN-190451-31-1

McAuliffe, Joseph C.; Stick, Robert V. Australian Journal of Chemistry (1997), 50(3), 225–228 compound 2 p226.

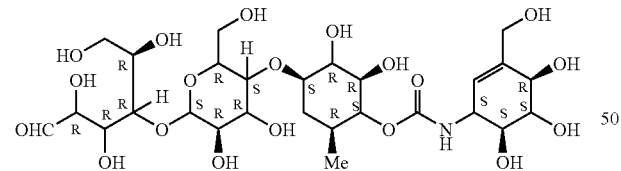

RN-190385-50-3

McAuliffe, Joseph C.; Stick, Robert V. Australian Journal of Chemistry (1997), 50(3), 203–207.

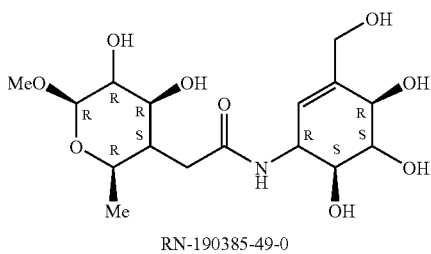

RN-190385-49-0

McAuliffe, Joseph C.; Stick, Robert V. Australian Journal of Chemistry (1997), 50(3), 203–207.

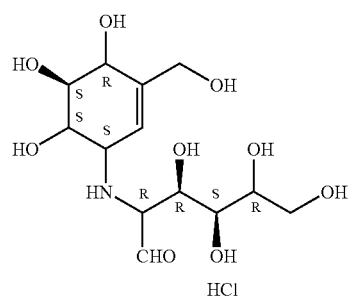

RN-186420-21-3

O. Srivastava and R. Sweda; U.S. Pat. No. 5,929,037 example 45 column 30.

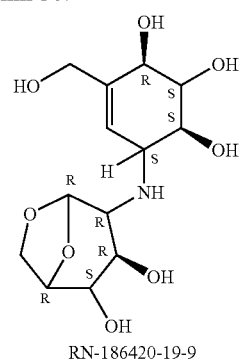

RN-186420-19-9

O. Srivastava and R. Sweda; U.S. Pat. No. 5,929,037 example 44 column 29.

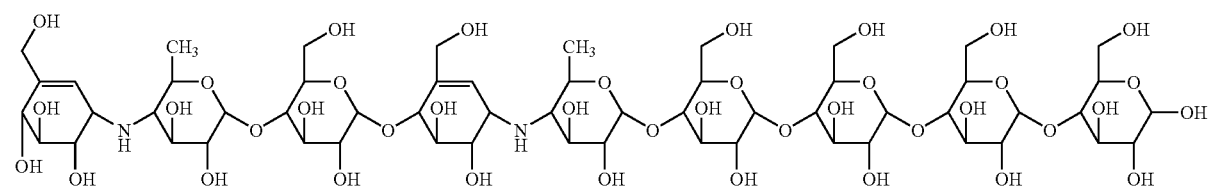

RN 179382-46-8

Banks et. al. EP-1157696-A2 p24.

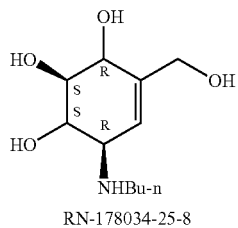

RN-178034-25-8

Ogawa, Seiichiro; Ashiura, Makoto; Uchida, Chikara; Watanabe, Shinsuke; Yamazaki, Chihiro; Yamagishi, Kimamu; Inokuchi. Jin-ichi. Bioorganic & Medicinal Chemistry Letters (1996), 6(8), 929–932 compound 3a p929.

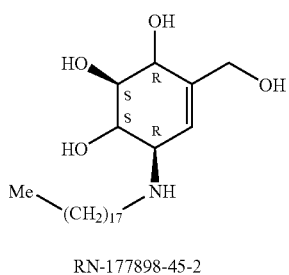

RN-177898-45-2

Ogawa, Seiichiro; Ashiura, Makoto; Uchida, Chikara; Watanabe, Shinsuke; Yamazaki, Chihiro; Yamagishi, Kimamu; Inokuchi, Jin-ichi. Bioorganic & Medicinal Chemistry Letters (1996), 6(8), 929–932 compound 3f p929.

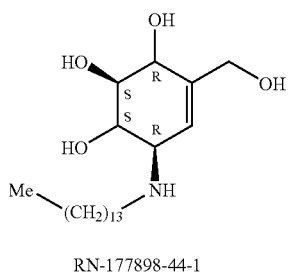

RN-177898-44-1

Ogawa, Seiichiro; Ashiura, Makoto; Uchida, Chikara; Watanabe, Shinsuke; Yamazaki, Chihiro; Yamagishi, Kimamu; Inokuchi, Jin-ichi. Bioorganic & Medicinal Chemistry Letters (1996), 6(8), 929–932 compound 3e p929.

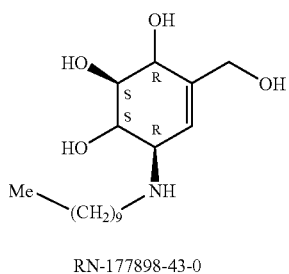

RN-177898-43-0

Ogawa, Seiichiro; Ashiura, Makoto; Uchida, Chikara; Watanabe, Shinsuke; Yamazaki, Chihiro; Yamagishi, Kimamu; Inokuchi, Jin-ichi. Bioorganic & Medicinal Chemistry Letters (1996), 6(8), 929–932 compound 3d p929.

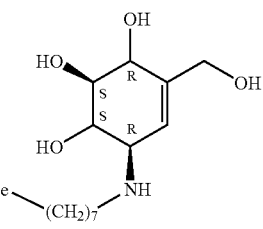

RN-177898-42-9

Ogawa, Seiichiro; Ashiura, Makoto; Uchida, Chikara; Watanabe, Shinsuke; Yamazaki, Chihiro; Yamagishi, Kimamu; Inokuchi, Jin-ichi. Bioorganic & Medicinal Chemistry Letters (1996), 6(8), 929–932 compound 3c p929.

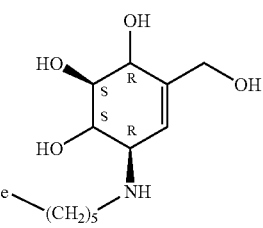

RN-177898-41-8

Ogawa, Seiichiro; Ashiura, Makoto; Uchida, Chikara; Watanabe, Shinsuke; Yamazaki, Chihiro; Yamagishi, Kimamu; Inokuchi, Jin-ichi. Bioorganic & Medicinal Chemistry Letters (1996), 6(8), 929–932 compound 3b p929.

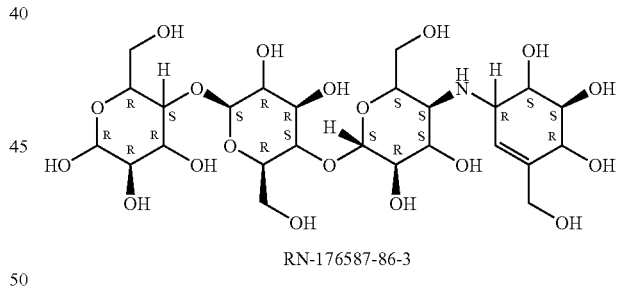

RN-176587-86-3

McAuliffe, Joseph C.; Stick, Robert V.; Stone, Bruce A. Tetrahedron Letters (1996), 37(14), 2479–82 compound □epimer of 2b p2479.

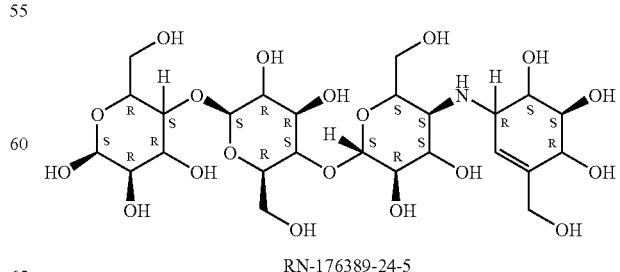

RN-176389-24-5

McAuliffe, Joseph C.; Stick, Robert V.; Stone, Bruce A. Tetrahedron Letters (1996), 37(14), 2479–82 compound α-epimer of 2b p2479.

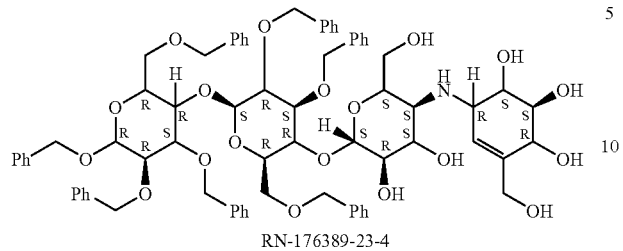

RN-176389-23-4

McAuliffe, Joseph C.; Stick, Robert V.; Stone, Bruce A. Tetrahedron Letters (1996), 37(14), 2479–82 compound 16 p2480.

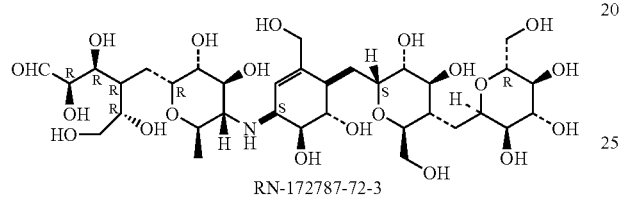

RN-172787-72-3

Cassset, Florence; Imberty, Anne; Haser, Richard; Payan, Francoise; Perez, Serge. European Journal of Biochemistry (1995), 232(1), 284–93. compound a p286.

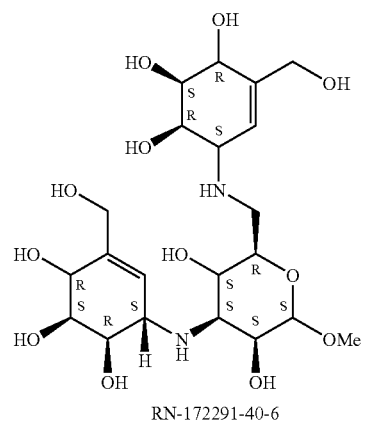

RN-172291-40-6

Ogawa, Seiichiro; Sasaki, Shin-ichi; Tsunoda, Hidetoshi. Carbohydrate Research (1995), 274 183–96 compound 4 p185.

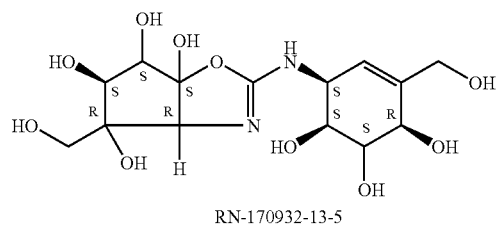

RN-170932-13-5

Uchida, Chikara; Kitahashi, Hideo; Watanabe, Shinsuke; Ogawa, Seiichiro. Journal of the Chemical Society, Perkin Transactions 1: Organic and Bio-Organic Chemistry (1995), (13), 1707–17 compound 10 p1708.

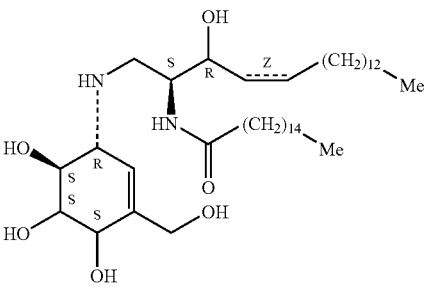

RN-162428-10-6

Tsunoda, Hidetoshi; Inokuchi, Jinichi; Yamagishi, Kiwamu; Ogawa, Seiichiro. Liebigs Annalen (1995), (2), 279–84 279.

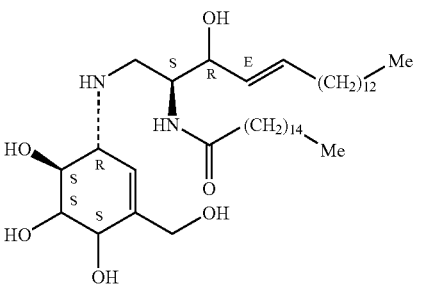

RN-162428-09-3

Tsunoda, Hidetoshi; Inokuchi, Jinichi; Yamagishi, Kiwamu; Ogawa, Seiichiro. Liebigs Annalen (1995), (2), 279–84 p279.

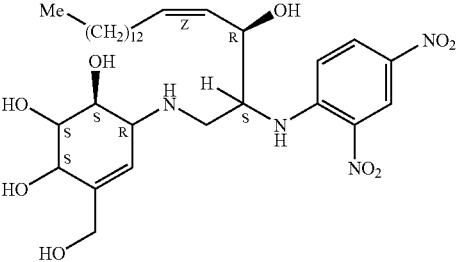

RN-162428-08-2

Tsunoda, Hidetoshi; Inokuchi, Jinichi; Yamagishi, Kiwamu; Ogawa, Seiichiro. Liebigs Annalen (1995), (2), 279–84 p279.

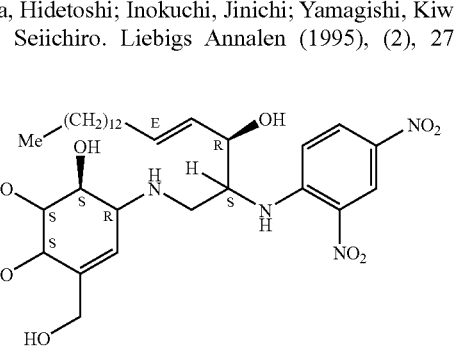

RN-162428-07-1

Tsunoda, Hidetoshi; Inokuchi, Jinichi; Yamagishi, Kiwamu; Ogawa, Seiichiro. Liebigs Annalen (1995), (2), 279–84 p279.

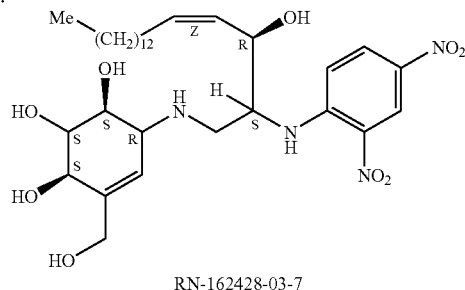

RN-162428-03-7

Tsunoda, Hidetoshi; Inokuchi, Jinichi; Yamagishi, Kiwamu; Ogawa, Seiichiro. Liebigs Annalen (1995), (2), 279–84 p280.

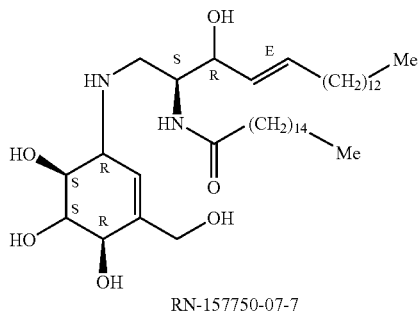

RN-157750-07-7

Ogawa, Seiichiro; Tsunoda, Hidetoshi; Inokuchi, Jinichi. Journal of the Chemical Society, Chemical Communications (1994), (11), 1317–18 compound E-2 p1317.

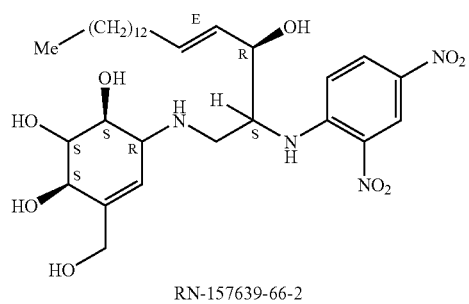

RN-157639-66-2

Ogawa, Seiichiro; Tsunoda, Hidetoshi; Inokuchi, Jinichi. Journal of the Chemical Society, Chemical Communications (1994), (11), 1317–18 compound 11 p1317.

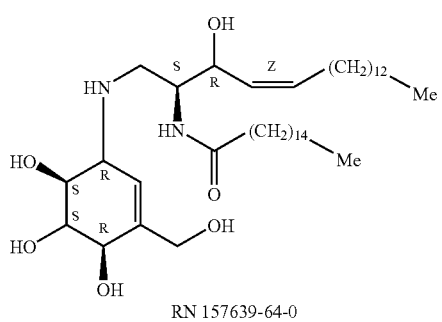

RN 157639-64-0

Ogawa, Seiichiro; Tsunoda, Hidetoshi; Inokuchi, Jinichi. Journal of the Chemical Society, Chemical Communications (1994), (11), 1317–18. compound Z-2 p1317.

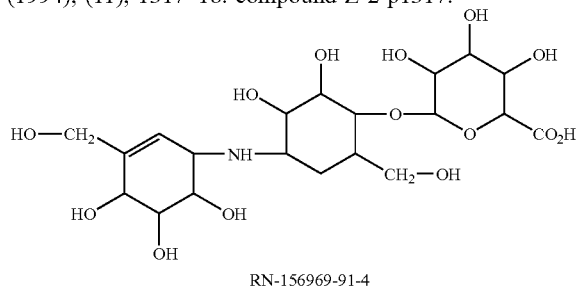

RN-156969-91-4

Ishiguro, Toshihiro; Oka, Masahide; Yamaguchi, Takamasa; Nogami, Ikuo. EP-599646-A2 p11 Table 4 row 6.

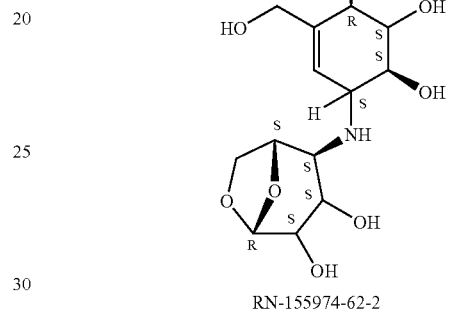

RN-155974-62-2

Ogawa, Seiichiro; Aso, Daisuke. Carbohydrate Research (1993), 250(1), 177–84. compound 4 p178.

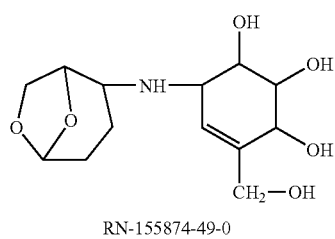

RN-155874-49-0

Ogawa, Seiichiro; Aso, Daisuke. Carbohydrate Research (1993), 250(1), 177–84. compound 11 p178.

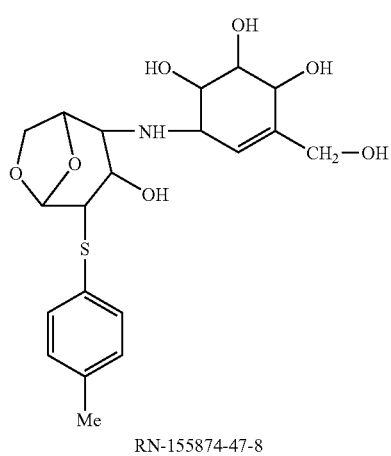

RN-155874-47-8

Ogawa, Seiichiro; Aso, Daisuke. Carbohydrate Research (1993), 250(1), 177–84. compound 9 p178.

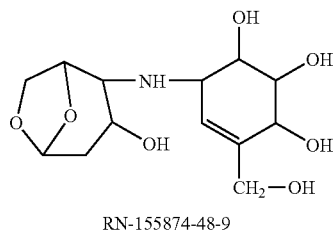

RN-155874-48-9

Ogawa, Seiichiro; Aso, Daisuke. Carbohydrate Research (1993), 250(1), 177–84. compound 10 p178.

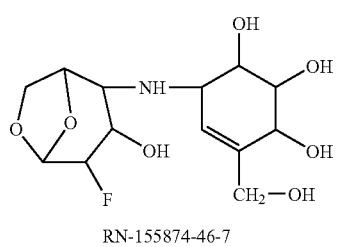

RN-155874-46-7

Ogawa, Seiichiro; Aso, Daisuke. Carbohydrate Research (1993), 250(1), 177–84. compound 8 p178.

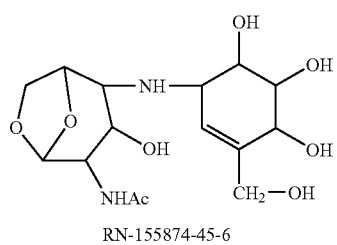

RN-155874-45-6

Ogawa, Seiichiro; Aso, Daisuke. Carbohydrate Research (1993), 250(1), 177–84. compound 7 p178.

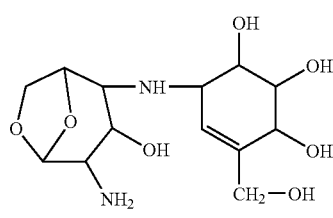

RN-155874-44-5

Ogawa, Seiichiro; Aso, Daisuke. Carbohydrate Research (1993). 250(1), 177–84. compound 6 p178.

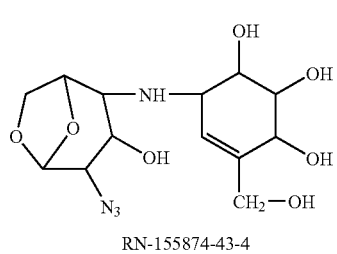

RN-155874-43-4

Ogawa, Seiichiro; Aso, Daisuke. Carbohydrate Research (1993), 250(1), 177–84. compound 5 p178.

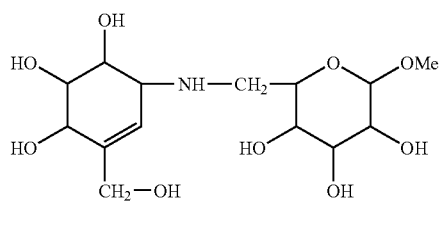

RN 152042-99-4

Cottaz, Sylvain; Brimacombe, John S.; Ferguson, Michael A. J. Carbohydrate Research (1993), 247 341–5.

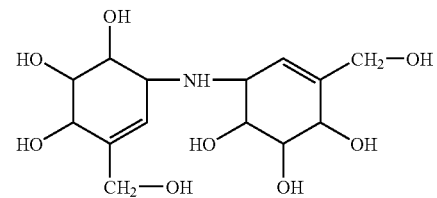

RN-148291-19-4

Ogawa, Seiichiro; Sato, Koji; Miyamoto, Yasunobu. Journal of the Chemical Society, Perkin Transactions 1: Organic and Bio-Organic Chem. (1972–1999) (1993), (6), 691–6.

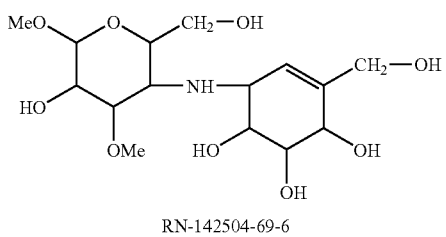

RN-142504-69-6

Shibata, Yasushi; Kosuge, Yasuhiro; Mizukoshi, Toshimi; Ogawa, Seiichiro. Carbohydrate Research (1992), 228(2), 377–98. compound 9 p378.

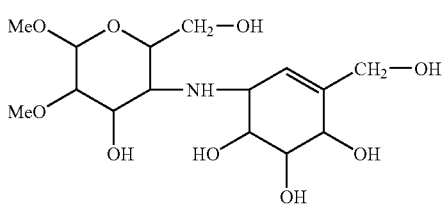

RN-142504-68-5

Shibata, Yasushi; Kosuge, Yasuhiro; Mizukoshi, Toshimi; Ogawa, Seiichiro. Carbohydrate Research (1992), 228(2), 377–98. compound 8 p378.

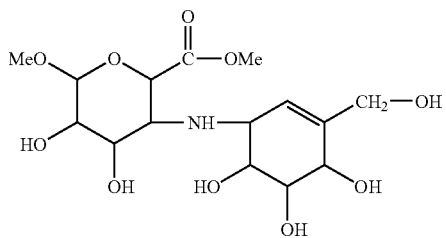

RN-142504-67-4

Shibata, Yasushi; Kosuge, Yasuhiro; Mizukoshi, Toshimi; Ogawa, Seiichiro. Carbohydrate Research (1992), 228(2), 377–98. compound 7 p378.

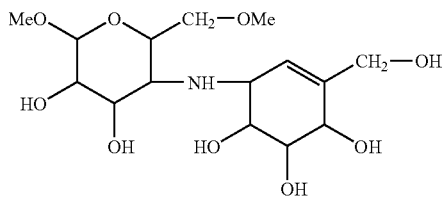

RN-142504-66-3

Shibata, Yasushi; Kosuge, Yasuhiro; Mizukoshi, Toshimi; Ogawa, Seiichiro. Carbohydrate Research (1992), 228(2), 377–98. compound 6 p378.

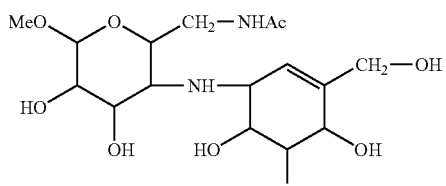

RN-142504-65-2

Shibata, Yasushi; Kosuge, Yasuhiro; Mizukoshi, Toshimi; Ogawa, Seiichiro. Carbohydrate Research (1992), 228(2), 377–98. compound 5 p378.

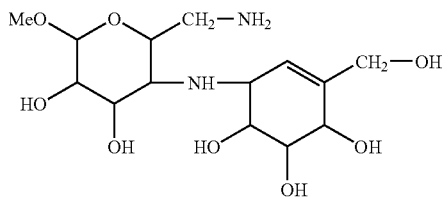

RN-142504-64-1

Shibata, Yasushi; Kosuge, Yasuhiro; Mizukoshi, Toshimi; Ogawa, Seiichiro. Carbohydrate Research (1992), 228(2), 377–98. compound 4 p378.

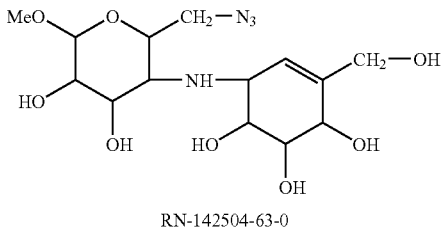

RN-142504-63-0

Shibata, Yasushi; Kosuge, Yasuhiro; Mizukoshi, Toshimi; Ogawa, Seiichiro. Carbohydrate Research (1992), 228(2), 377–98. compound 3 p378.

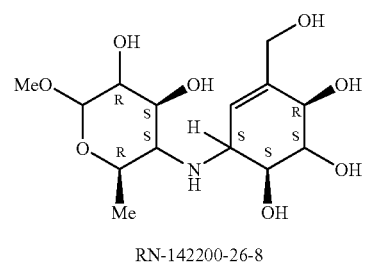

RN-142200-26-8

Svensson, Birte; Sierks, Michael R. Dep. Chem., Carlsberg Lab., Valby, Den. Carbohydrate Research (1992), 227 p29–44.

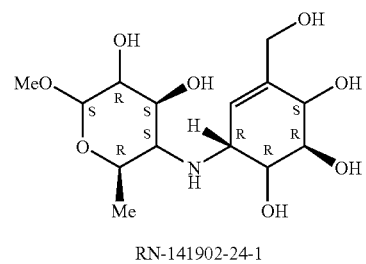

RN-141902-24-1

Shibata Y; Kosuge Y; Mizukoshi T; Ogawa S Carbohydrate Research (1992 Apr. 27), 228(2). 377–98 compound 1 p378.

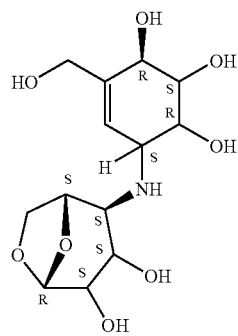

RN-141316-52-1

Ogawa, Seiichiro; Nakamura, Yoshikazu. Fac. Sci. Technol., Keio Univ., Yokohama, Japan. Carbohydrate Research (1992), 226(1), 79–89 compound 5a p79.

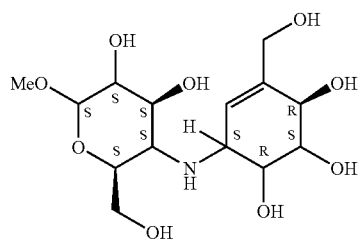

RN-141316-51-0

Ogawa, Seiichiro; Nakamura, Yoshikazu. Fac. Sci. Technol., Keio Univ., Yokohama, Japan. Carbohydrate Research (1992), 226(1), 79–89 compound 4a p79.

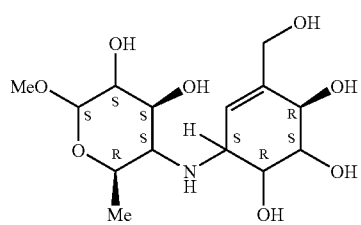

RN-141316-50-9

Ogawa, Seiichiro; Nakamura, Yoshikazu. Fac. Sci. Technol., Keio Univ., Yokohama, Japan. Carbohydrate Research (1992), 226(1), 79–89 compound 3a p79.

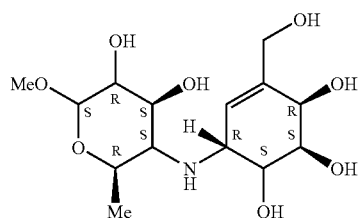

RN-140148-00-1

Ogawa, Seiichiro; Uchida, Chikara; Shibata, Yasushi. Carbohydrate Research (1992), 223 279–86.

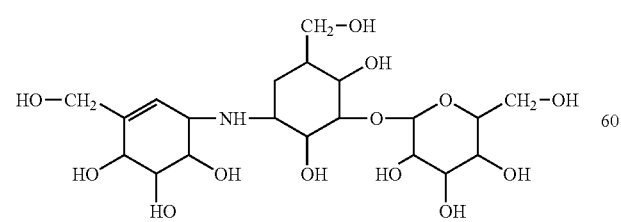

RN-139628-10-7

Asano, Naoki; Kameda, Yukihiko; Matsui, Katsuhiko. Journal of Antibiotics (1991), 44(12), 1406–16 p1407.

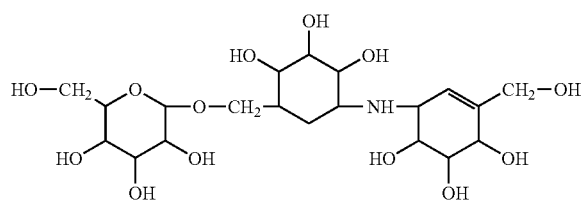

RN-139628-09-4

Asano, Naoki; Kameda, Yukihiko; Matsui, Katsuhiko. Journal of Antibiotics (1991), 44(12). 1406–16 p1407.

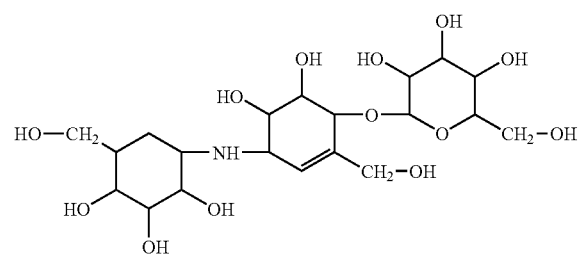

RN-139261-95-3

Asano, Naoki; Kameda, Yukihiko; Matsui, Katsuhiko. Journal of Antibiotics (1991), 44(12), 1406–16 p1407.

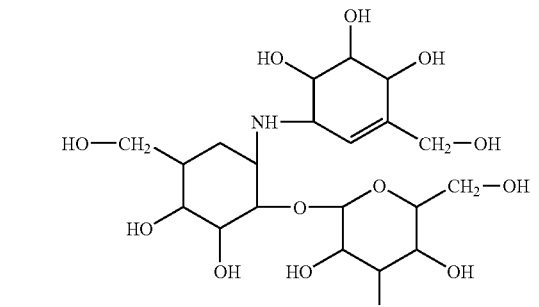

RN-139261-94-2

Asano, Naoki; Kameda, Yukihiko; Matsui, Katsuhiko. Journal of Antibiotics (1991), 44(12), 1406–16 p1407.

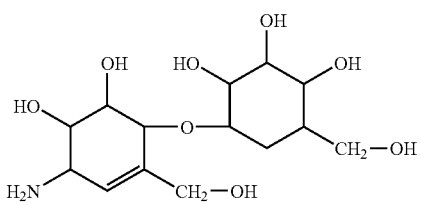

RN-134308-81-9

Asano, Naoki; Kameda, Yukihiko; Matsui, Katsuhiko. Journal of Antibiotics (1991), 44(12), 1406–16 p1409.

RN 134221-44-6

Furumoto, Tadashi; Yoshioka, Tadashi; Kamata, Kanae; Kameda, Yukihiko; Matsui, Katsuhiko. Journal of Antibiotics (1991), 44(3), 371–3.

RN-134221-43-5

Furumoto, Tadashi; Kameda, Yukihiko; Matsui, Katsuhiko. Chemical & Pharmaceutical Bulletin (1992), 40(7), 1871–5 p1872.

RN-132016-21-8

Ogawa, Seiichiro; Shibata, Yasushi; Kosuge, Yasuhiro; Yasuda, Kuninobu; Mizukoshi, Toshimi; Uchida, Chikara. Journal of the Chemical Society, Chemical Communications (1990), (20), 1387–8 p1388.

RN-132016-20-7

Ogawa, Seiichiro; Shibata, Yasushi; Kosuge, Yasuhiro; Yasuda, Kuninobu; Mizukoshi, Toshimi; Uchida, Chikara. Journal of the Chemical Society, Chemical Communications (1990), (20), 1387–8 p1388.

RN-131922-36-6

Ogawa, Seiichiro; Shibata, Yasushi; Kosuge, Yasuhiro; Yasuda, Kuninobu; Mizukoshi, Toshimi; Uchida, Chikara. Journal of the Chemical Society, Chemical Communications (1990), (20), 1387–8 p1388.

RN-131922-32-2

Ogawa, Seiichiro; Shibata, Yasushi; Kosuge, Yasuhiro; Yasuda, Kuninobu; Mizukoshi, Toshimi; Uchida, Chikara. Journal of the Chemical Society, Chemical Communications (1990), (20), 1387–8 p1388.

RN-130812-69-0

Asano, Naoki; Kameda, Yukihiko; Matsui, Katsuhiko; Horii, Satoshi; Fukase, Hiroshi. Journal of Antibiotics (1990), 43(8), 1039–41 p1040.

RN-130069-26-0

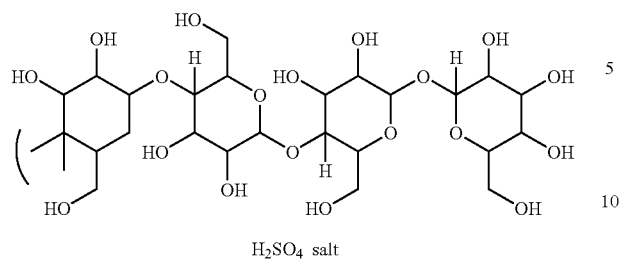

H₂SO₄ salt

Wessel, Hans Peter; Hosang, Markus; Tschopp, Thomas B.; Weimann, Bernd Juergen. Carbohydrate Research (1990), 204 131–9.

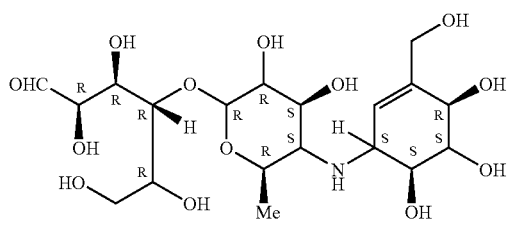

RN-129446-91-9

Boberg, M.; Kurz, J.; Ploschke, H. J.; Schmitt, P.; Scholl, H.; Shueller, M.; Wuensche, C. Arzneimittel-Forschung (1990), 40(5), 555–63 compound 4 p559.

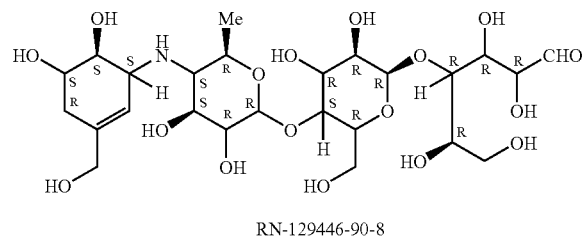

RN-129446-90-8

Boberg, M.; Kurz, J.; Ploschke, H. J.; Schmitt, P.; Scholl, H.; Shueller, M.; Wuensche, C. Arzneimittel-Forschung (1990), 40(5), 555–63 p559.

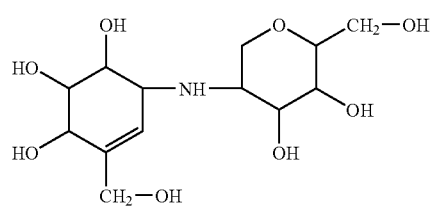

RN 128826-89-1

Vertesy et. al. U.S. Pat. No. 5,091,524.

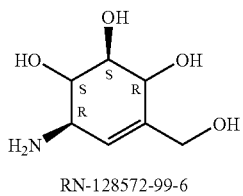

RN-128572-99-6

Nicotra, Francesco; Panza, Luigi; Ronchetti, Fiamma; Russo, Giovanni. Gazzetta Chimica Italiana (1989), 119 (11), 577–9 compound 2 p577.

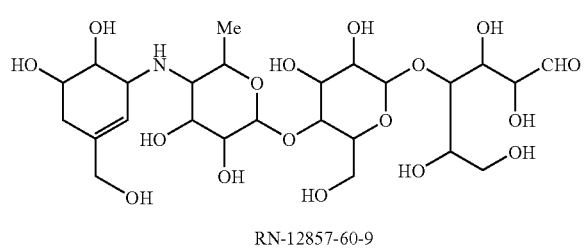

RN-12857-60-9

Maul, W.; Mueller, L.; Pfitzner, J.; Rauenbusch, E.; Schutt, H. Arzneimittel-Forschung (1989), 39(10), 1251–3 p1251.

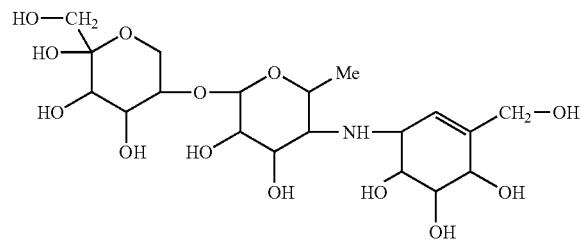

RN-124534-96-9

Takahashi, Yoshinori; Sakaguchi, Fumiaki; Morimoto, Keiko; Hashimoto, Komei; Funaba, Tsukasa; Hayauchi, Yutaka. Iyakuhin Kenkyu (1989), 20(4), 769–83.

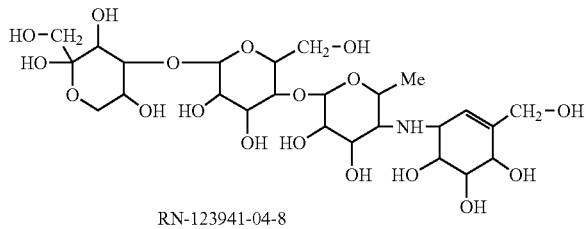

RN-123941-04-8

Takahashi, Yoshinori; Sakaguchi, Fumiaki; Morimoto, Keiko; Hashimoto, Komei; Funaba, Tsukasa; Hayauchi, Yutaka. Iyakuhin Kenkyu (1989), 20(4), 769–83.

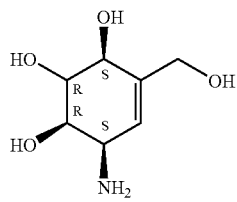
RN-112067-63-7

Jin, Wen Zao; Rinehart, Kenneth L., Jr.; Toyokuni, Tatsushi. Journal of Antibiotics (1987), 40(3), 329–39 compound 4 p336.

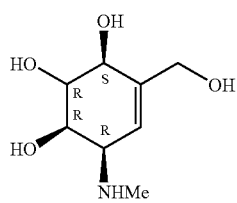
RN-112014-09-2

Jin, Wen Zao; Rinehart, Kenneth L.; Jr.; Toyokuni, Tatsushi. Journal of Antibiotics (1987), 40(3), 329–39 compound 6 p337.

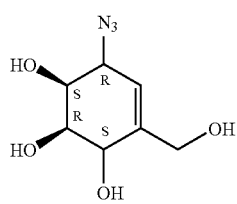
RN-109718-71-0

Ogawa, Seiichiro; Sugizaki, Hiroyasu. Chemistry Letters (1986), (11), 1977–80 compound 5b p1978.

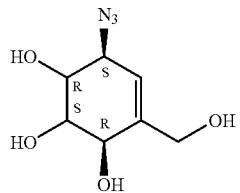
RN-109718-70-9

Ogawa, Seiichiro; Sugizaki, Hiroyasu. Chemistry Letters (1986), (11), 1977–80 p1978.

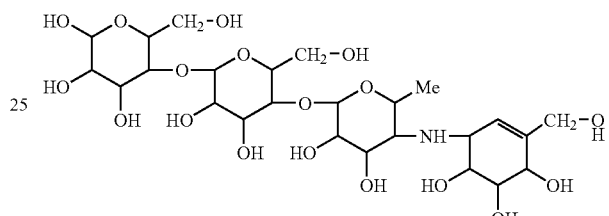
RN-106864-10-2

Pfeffer, M.; Siebert, G. Zeitschrift fuer Ernaehrungswissenschaft (1986), 25(3), 189–95.

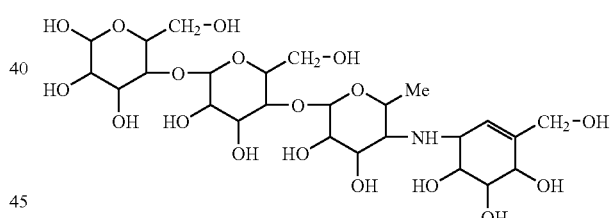
RN-106864-09-9

Pfeffer, M.; Siebert, G. Zeitschrift fuer Ernaehrungswissenschaft (1986), 25(3), 189–95.

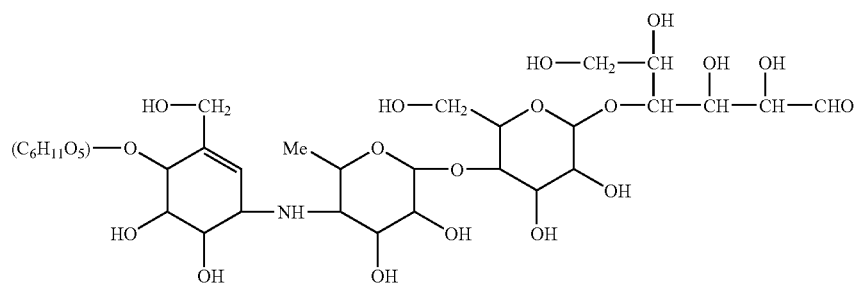
RN-106861-26-1

Pfeffer, M.; Siebert, G. Zeitschrift fuer Ernaehrungswissenschaft (1986), 25(3), 189–95.

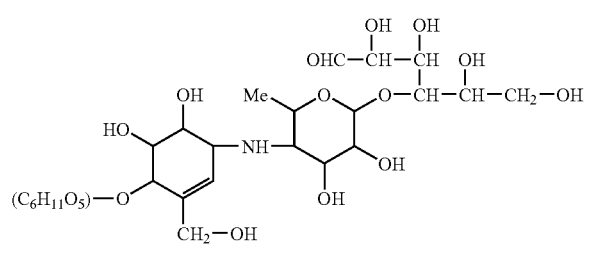

RN-106818-23-9

Pfeffer, M.; Siebert, G. Zeitschrift fuer Ernaehrungswissenschaft (1986), 25(3), 189–95.

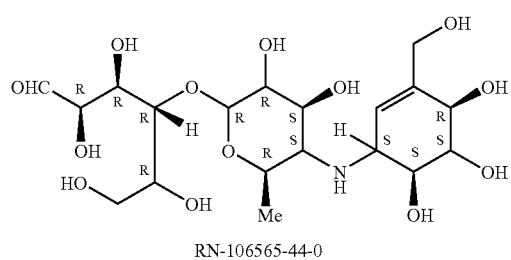

RN-106565-44-0

Pfeffer, M.; Siebert, G. Zeitschrift fuer Ernaehrungswissenschaft (1986), 25(3), 189–95.

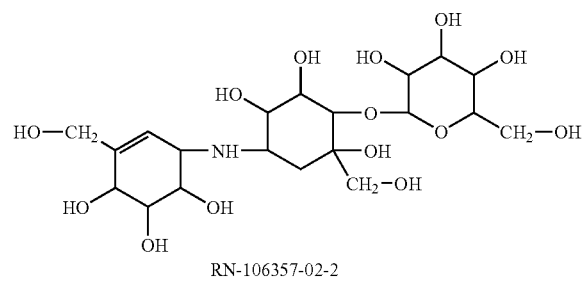

RN-106357-02-2

Fukase, Hiroshi; Horii, Satoshi. Journal of Organic Chemistry (1992), 57(13), 3651–8.

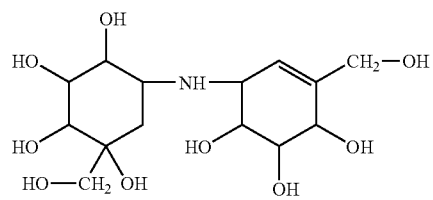

RN-106357-01-1

Fukase, Hiroshi; Horii, Satoshi. Journal of Organic Chemistry (1992), 57(13), 3651–8.

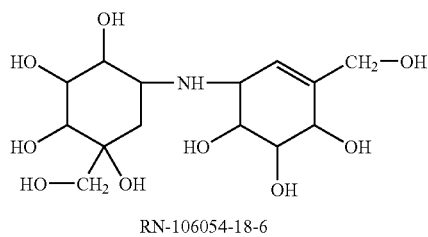

RN-106054-18-6

Kameda, Yukihiko; Asano, Naoki; Yamaguchi, Takuji; Matsui, Katsuhiko; Horii, Satoshi; Fukase, Hiroshi. Journal of Antibiotics (1986), 39(10), 1491–4 p1491.

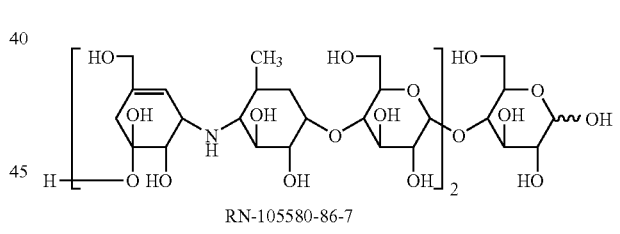

RN-106054-17-5

Kameda, Yukihiko; Asano, Naoki; Yamaguchi, Takuji; Matsui, Katsuhiko; Horii, Satoshi; Fukase, Hiroshi. Journal of Antibiotics (1986), 39(10), 1491–4 p1491.

RN-105580-86-7

Vertesy, Laszlo; Bender, Rudolf; Fehlhaber, Hans Wolfram. EP-173950-A2 p1.

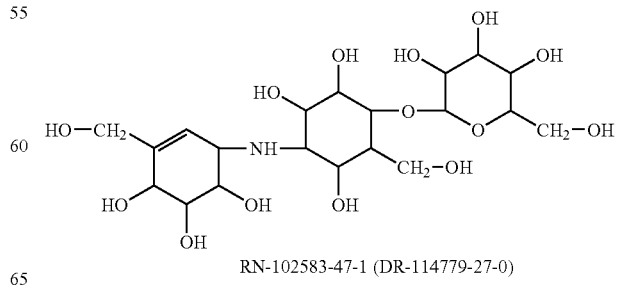

RN-102583-47-1 (DR-114779-27-0)

Ogawa, Seiichiro; Miyamoto, Yasunobu; Nose, Taisuke. Journal of the Chemical Society, Perkin Transactions 1: Organic and Bio-Organic Chemistry (1972–1999) (1988), (9), 2675–80 compound 1a p2675.

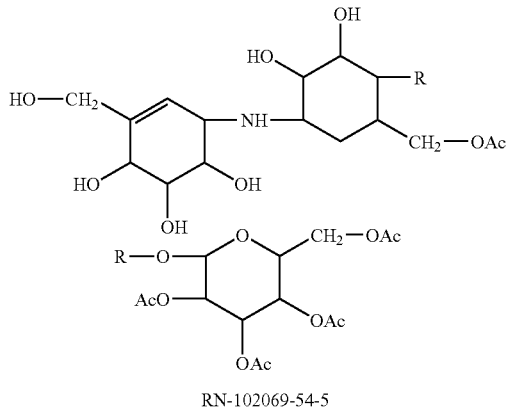

RN-102069-54-5

Ogawa, Seiichiro; Nose, Taisuke; Ogawa, Takao; Toyokuni, Tatsushi; Iwasawa, Yoshikazu; Suami, Tetsuo. Journal of the Chemical Society, Perkin Transactions 1: Organic and Bio-Organic Chemistry (1972–1999) (1985), (11), 2369–74.

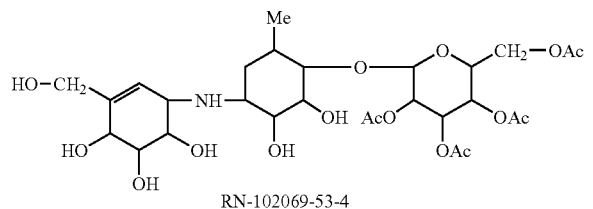

RN-102069-53-4

Ogawa, Seiichiro; Nose, Taisuke; Ogawa, Takao; Toyokuni, Tatsushi; Iwasawa, Yoshikazu; Suami, Tetsuo. Journal of the Chemical Society, Perkin Transactions 1: Organic and Bio-Organic Chemistry (1972–1999) (1985), (11), 2369–74.

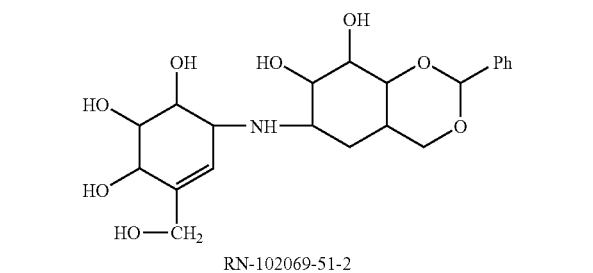

RN-102069-51-2

Ogawa, Seiichiro; Nose, Taisuke; Ogawa, Takao; Toyokuni, Tatsushi; Iwasawa, Yoshikazu; Suami, Tetsuo. Journal of the Chemical Society, Perkin Transactions 1: Organic and Bio-Organic Chemistry (1972–1999) (1985), (11), 2369–74.

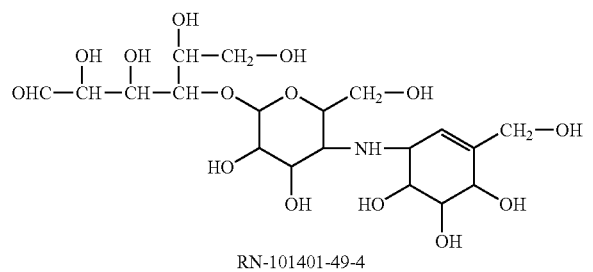

RN-101401-49-4

Ogawa, Seiichiro; Iwasawa, Yoshikazu; Toyokuni, Tatsushi; Suami, Tetsuo. Carbohydrate Research (1985), 141(1), 29–40.

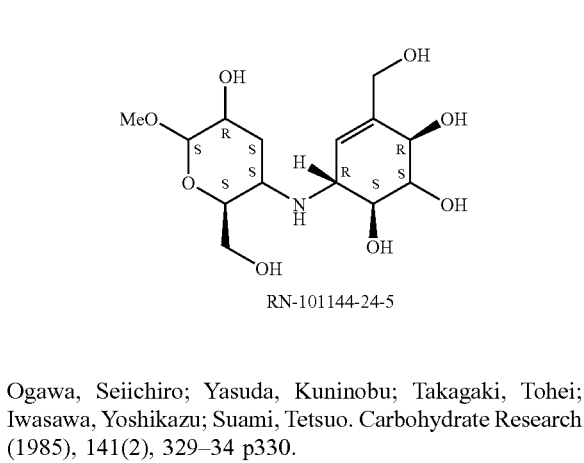

RN-101144-24-5

Ogawa, Seiichiro; Yasuda, Kuninobu; Takagaki, Tohei; Iwasawa, Yoshikazu; Suami, Tetsuo. Carbohydrate Research (1985), 141(2), 329–34 p330.

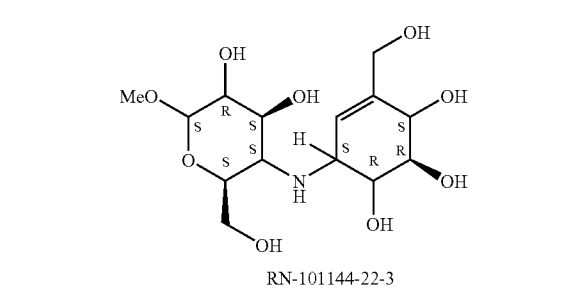

RN-101144-22-3

Ogawa, Seiichiro; Yasuda, Kuninobu; Takagaki, Tohei; Iwasawa, Yoshikazu; Suami, Tetsuo. Carbohydrate Research (1985), 141(2), 329–34.

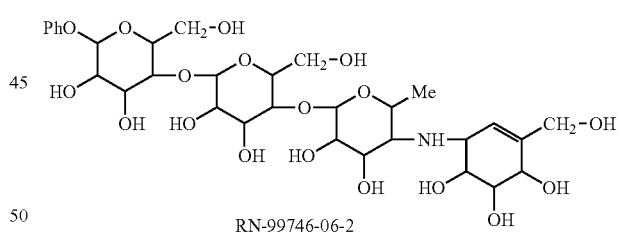

RN-99746-06-2

Schmidt, Richard R.; Laesecke, Klaus. CH-648326-A.

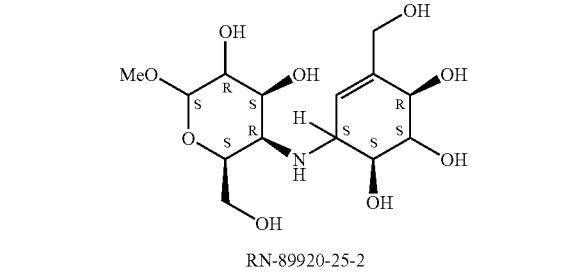

RN-89920-25-2

Horii, Satoshi; Fukase, Hiroshi; Matsuo, Takao; Kameda, Yukihiko; Asano, Naoki; Matsui, Katsuhiko. Journal of Medicinal Chemistry (1986), 29(6), 1038–46 p1040.

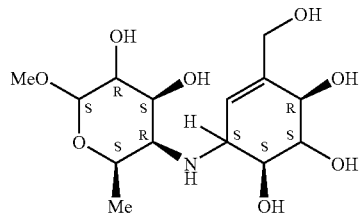

RN-89920-24-1

Horii, Satoshi; Kameda, Yukihiko; Fukase, Hiroshi. EP-89812-A1.

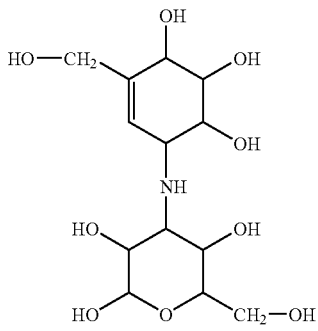

RN-89859-72-3

Horii, Satoshi; Fukase, Hiroshi; Matsuo, Takao; Kameda, Yukihiko; Asano, Naoki; Matsui, Katsuhiko. Journal of Medicinal Chemistry (1986), 29(6), 1038–46 p1040.

Horii, Satoshi; Kameda, Yukihiko; Fukase, Hiroshi. EP-89812-A1.

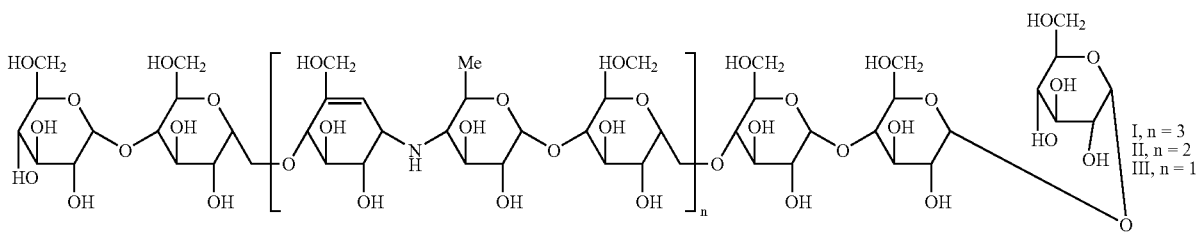

RN-89498-90-8 = compound I
RN-89498-89-5 = compound II
RN-89498-88-4 = compound III

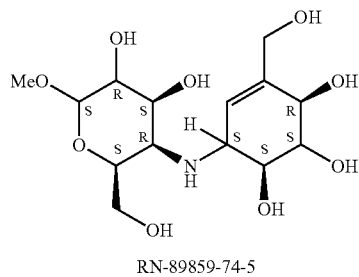

RN-89859-74-5

Yokose, Kazuteru; Ogawa, Mayumi; Ogawa, Kiyoshi. Journal of Antibiotics (1984), 37(2), 182–6.

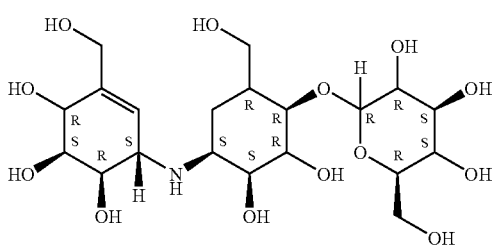

RN-87037-90-9

Ogawa, Seiichiro; Iwasawa, Yoshikazu; Toyokuni, Tatsushi; Suami, Tetsuo. Carbohydrate Research (1985), 141(1), 29–40.

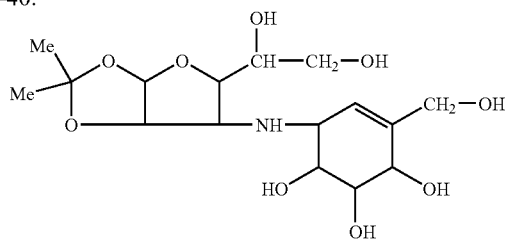

RN-89859-73-4

Ogawa, Seiichiro; Inoue, Makoto; Iwasawa, Yoshikazu; Toyokuni, Tatsushi; Suami, Tetsuo. Chemistry Letters (1983), (7), 1085–8 p1085.

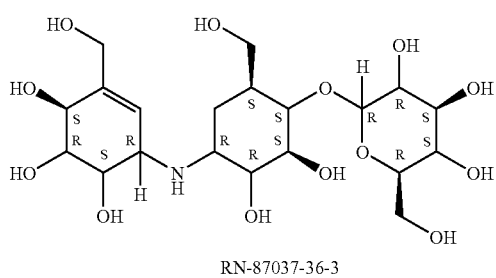

RN-87037-36-3

Ogawa, Seiichiro; Inoue, Makoto; Iwasawa, Yoshikazu; Toyokuni, Tatsushi; Suami, Tetsuo. Chemistry Letters (1983), (7), 1085–8 p1085.

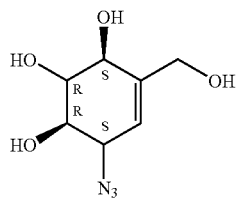

RN-86900-52-9

Toyokuni, Tatsushi; Ogawa, Seiichiro; Suami, Tetsuo. Bulletin of the Chemical Society of Japan (1983), 56(4), 1161–70 p1163.

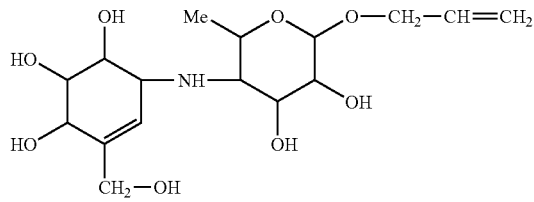

RN-85440-55-7

Heiker, Fred Robert; Mueller, Lutz; Puls, Walter; Bischoff, Hilmar. EP-64635-A1.

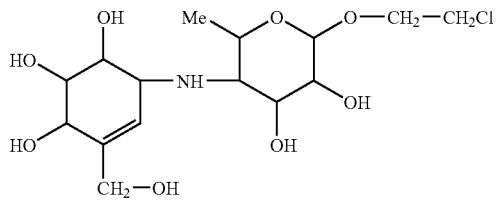

RN-85440-54-6

Heiker, Fred Robert; Mueller, Lutz; Puls, Walter; Bischoff, Hilmar. EP-64635-A1.

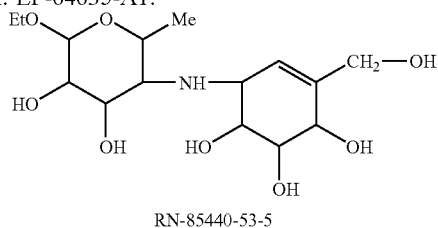

RN-85440-53-5

Heiker, Fred Robert; Mueller, Lutz; Puls, Walter; Bischoff, Hilmar. EP-64635-A1.

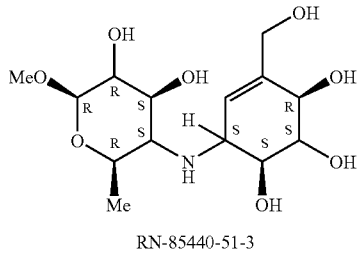

RN-85440-51-3

Junge, Bodo; Heiker, Fred R.; Kurz, Juergen; Mueller, Lutz; Schmidt, Delf D.; Wuensche, Christian. Carbohydrate Research (1984), 128(2), 235–68.

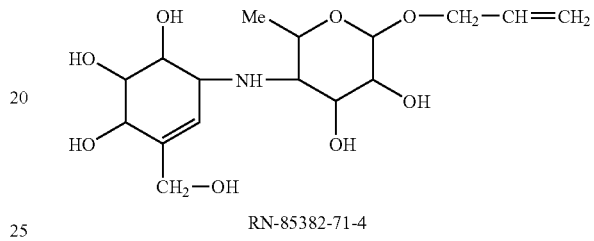

RN-85382-71-4

Heiker, Fred Robert; Mueller, Lutz; Puls, Walter; Bischoff, Hilmar. EP-64635-A1.

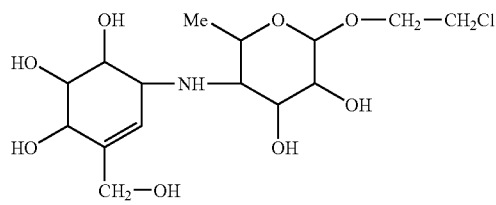

RN-85382-70-3

Heiker, Fred Robert; Mueller, Lutz; Puls, Walter; Bischoff, Hilmar. EP-64635-A1.

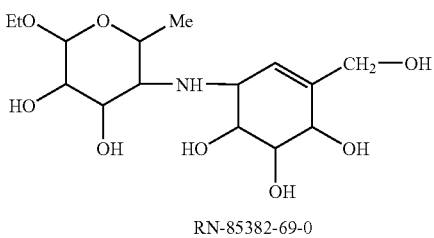

RN-85382-69-0

Heiker, Fred Robert; Mueller, Lutz; Puls, Walter; Bischoff, Hilmar. EP-64635-A1.

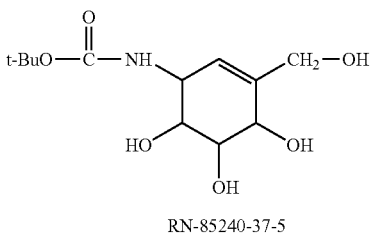

RN-85240-37-5

Horii, Satoshi; Kameda, Yukihiko; Fukase, Hiroshi. EP-89812-A1.

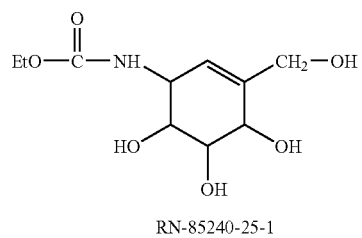

RN-85240-25-1

Horii, Satoshi; Kameda, Yukihiko; Fukase, Hiroshi. EP-89812-A1.

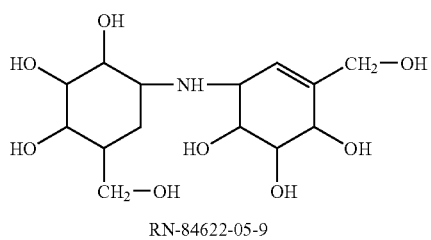

RN-84622-05-9

Ogawa, Seiichiro; Suetsugu, Masaru; Toyakuni, Tatsushi; Suami, Tetsuo. Nippon Kagaku Kaishi (1982), (10), 1721–6.

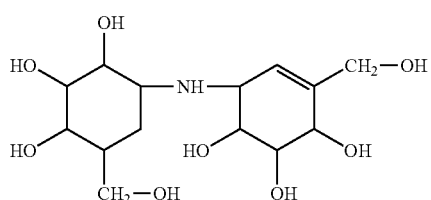

RN-84622-04-8

Ogawa, Seiichiro; Suetsugu, Masaru; Toyakuni, Tatsushi; Suami, Tetsuo. Nippon Kagaku Kaishi (1982), (10), 1721–6.

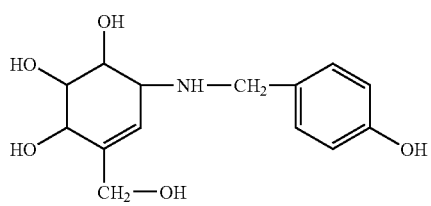

RN-84367-25-9

Kameda, Yukihiko; Asano, Naoki; Yoshikawa, Michiyo; Matsui, Katsuhiko; Horii, Satoshi; Fukase, Hiroshi. Journal of Antibiotics (1982), 35(11), 1624–6.

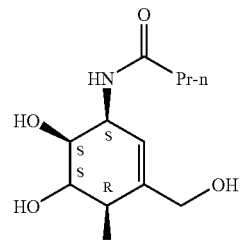

RN-84293-54-9

Kameda, Yukihiko; Asano, Naoki; Yoshikawa, Michiyo; Matsui, Katsuhiko; Horii, Satoshi; Fukase, Hiroshi. Journal of Antibiotics (1982), 35(11), 1624–6.

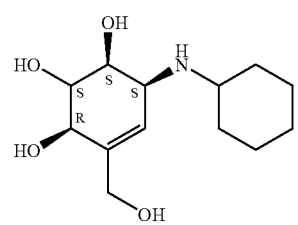

RN-84270-04-2

Kameda, Yukihiko; Asano, Naoki; Yoshikawa, Michiyo; Matsui, Katsuhiko; Horii, Satoshi; Fukase, Hiroshi. Journal of Antibiotics (1982), 35(11), 1624–6.

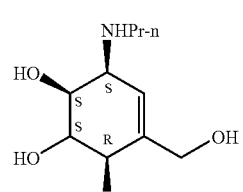

RN-84270-03-1

Kameda, Yukihiko; Asano, Naoki; Yoshikawa, Michiyo; Matsui, Katsuhiko; Horii, Satoshi; Fukase, Hiroshi. Journal of Antibiotics (1982), 35(11), 1624–6.

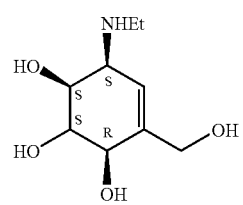

RN-84270-02-0

Kameda, Yukihiko; Asano, Naoki; Yoshikawa, Michiyo; Matsui, Katsuhiko; Horii, Satoshi; Fukase, Hiroshi. Journal of Antibiotics (1982), 35(11), 1624–6.

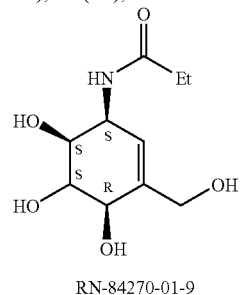

RN-84270-01-9

Kameda, Yukihiko; Asano, Naoki; Yoshikawa, Michiyo; Matsui, Katsuhiko; Horii, Satoshi; Fukase, Hiroshi. Journal of Antibiotics (1982), 35(11), 1624–6.

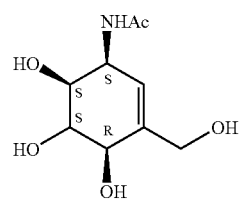

RN-84270-00-8

Kameda, Yukihiko; Asano, Naoki; Yoshikawa, Michiyo; Matsui, Katsuhiko; Horii, Satoshi; Fukase, Hiroshi. Journal of Antibiotics (1982), 35(11), 1624–6.

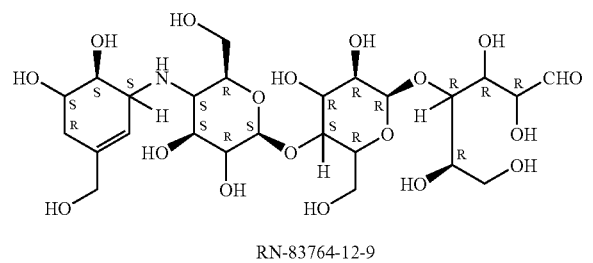

RN-83764-12-9

Kangouri, Kunjo; Namiki, Shinjuro; Nagate, Takatoshi; Hara, Hiroshi; Sugita, Kazuhiko; Omura, Sadafumi. Journal of Antibiotics (1982), 35(9), 1160–6.

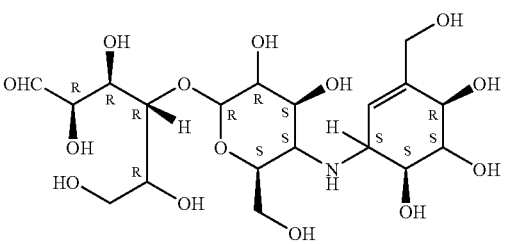

RN-83764-11-8

Kangouri, Kunjo; Namiki, Shinjuro; Nagate, Takatoshi; Hara, Hiroshi; Sugita, Kazuhiko; Omura, Sadafumi. Journal of Antibiotics (1982), 35(9), 1160–6.

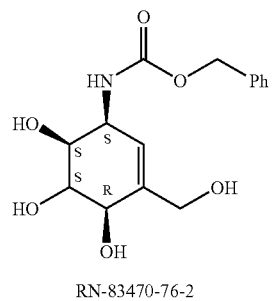

RN-83470-76-2

Horii, Satoshi; Kameda, Yukihiko; Fukase, Hiroshi. EP-56194-A1.

PAGE 1-A

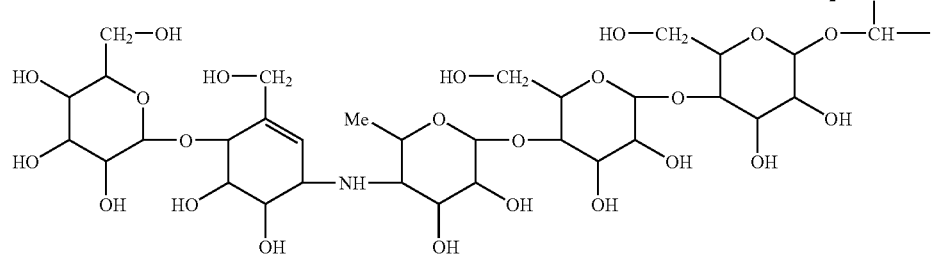

RN-83116-11-4

PAGE

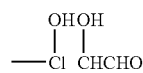

Fukuhara, Kenichi; Murai, Hidetsugu; Murao, Sawao. Agricultural and Biological Chemistry (1982) 46(7), 1941–5.

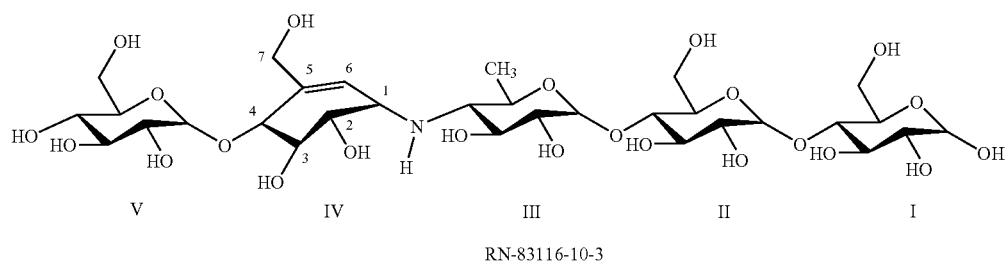

RN-83116-10-3

Yoon, Seung-Heon; Robyt, John F. Carbohydrate Research (2002), 337(6), 509–516.

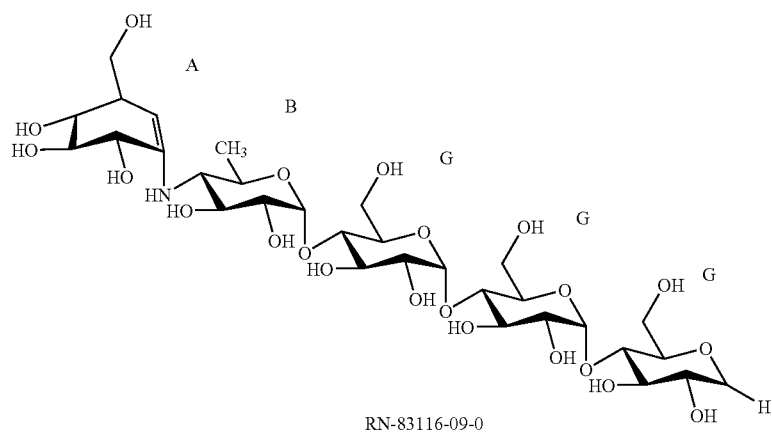

RN-83116-09-0

Nahoum, Virginie; Roux, Genevieve; Anton, Veronique; Rouge, Pierre; Puigserver, Antoine; Bischoff, Hilmar; Henrissat, Bernard; Payan, Francoise. Biochemical Journal (2000), 346(1), 201–208.

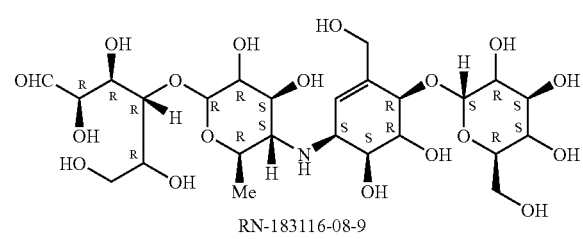

RN-183116-08-9

Kim, Myo-Jeong; Lee, Hee-Seob; Cho, Jin-Sook; Kim, Tae-Jip; Moon, Tae-Wha; Oh, Sang-Taek; Kim, Jung-Wan;

Oh, Byung-Ha; Park, Kwan-Hwa. Biochemistry (2002), 41(29), 9099–9108.

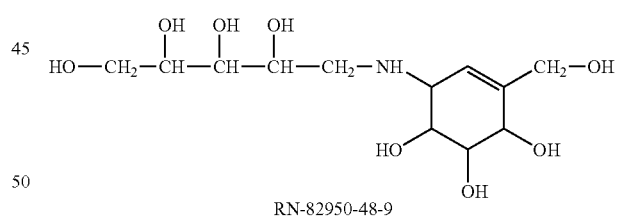

RN-82950-48-9

Horii, Satoshi; Kameda, Yukihiko; Fukase, Hiroshi. EP-49981-A1 p10.

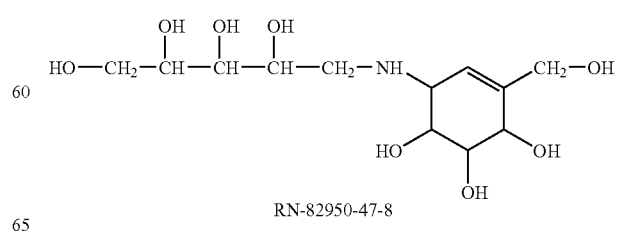

RN-82950-47-8

Horii, Satoshi; Kameda, Yukihiko; Fukase, Hiroshi. EP-49981-A1 p10.

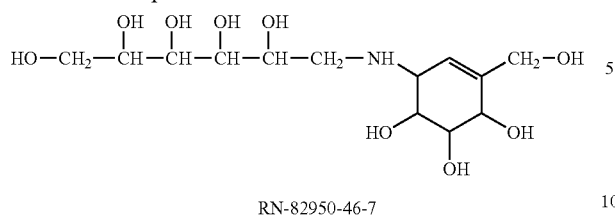

RN-82950-46-7

Horii, Satoshi; Kameda, Yukihiko; Fukase, Hiroshi. EP-49981-A1 p7.

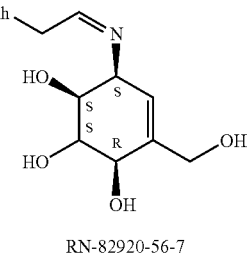

RN-82920-56-7

Horii, Satoshi; Kameda, Yukihiko; Fukase, Hiroshi. EP-49981-A1 p10.

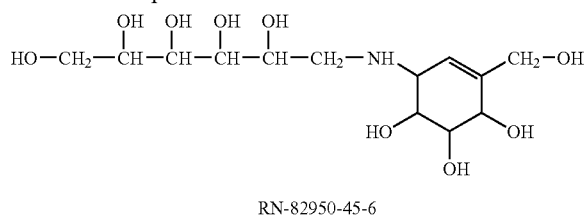

RN-82950-45-6

Horii, Satoshi; Kameda, Yukihiko; Fukase, Hiroshi. EP-49981-A1 p16.

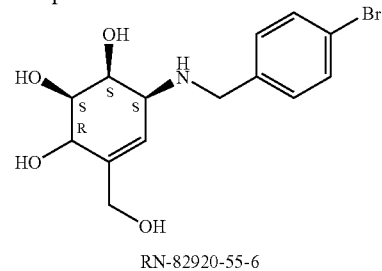

RN-82920-55-6

Horii, Satoshi; Kameda, Yukihiko; Fukase, Hiroshi. EP-49981-A1 p10.

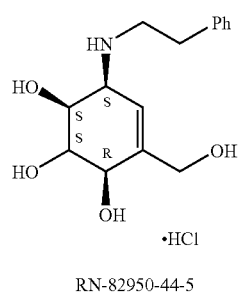

RN-82950-44-5

Horii, Satoshi; Kameda, Yukihiko; Fukase, Hiroshi. EP-49981-A1 p11.

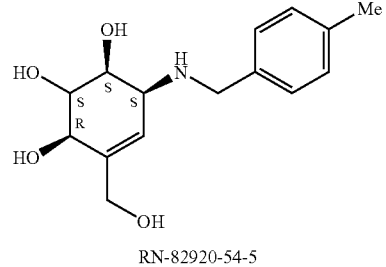

RN-82920-54-5

Horii, Satoshi; Kameda, Yukihiko; Fukase, Hiroshi. EP-49981-A1 p8.

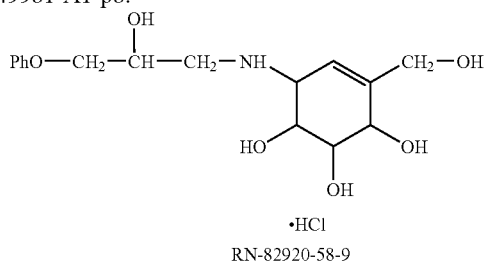

RN-82920-58-9

Horii, Satoshi; Kameda, Yukihiko; Fukase, Hiroshi. EP-49981-A1 p7.

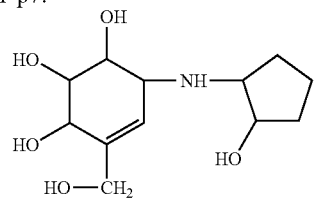

RN-82920-53-4

Horii, Satoshi; Kameda, Yukihiko; Fukase, Hiroshi. EP-49981-A1 p12.

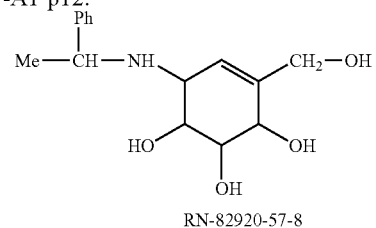

RN-82920-57-8

Horii, Satoshi; Kameda, Yukihiko; Fukase, Hiroshi. EP-49981-A1 p24.

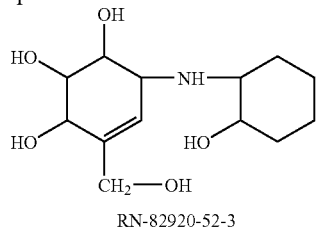

RN-82920-52-3

Horii, Satoshi; Kameda, Yukihiko; Fukase, Hiroshi. EP-49981-A1 p23.

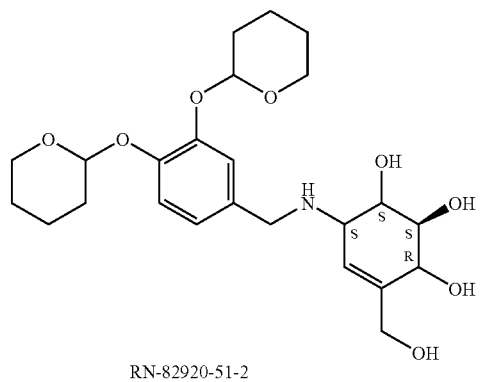

RN-82920-51-2

Horii, Satoshi; Kameda, Yukihiko; Fukase, Hiroshi. EP-49981-A1 p23.

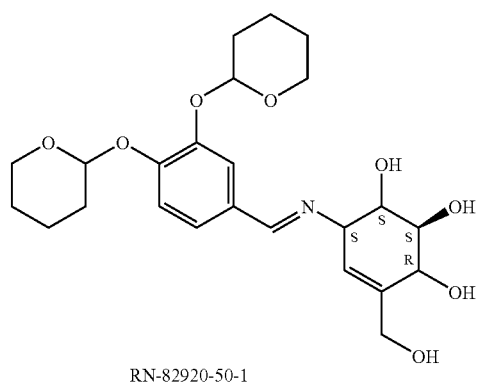

RN-82920-50-1

Horii, Satoshi; Kameda, Yukihiko; Fukase, Hiroshi. EP-49981-A1 p23.

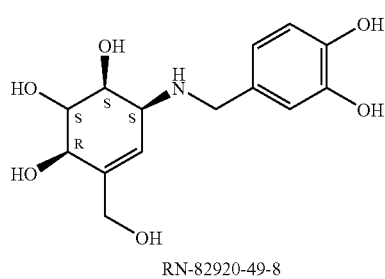

RN-82920-49-8

Horii, Satoshi; Kameda, Yukihiko; Fukase, Hiroshi. EP-49981-A1 p23.

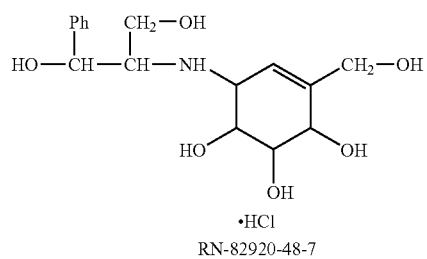

·HCl
RN-82920-48-7

Horii, Satoshi; Kameda, Yukihiko; Fukase, Hiroshi. EP-49981-A1 p12

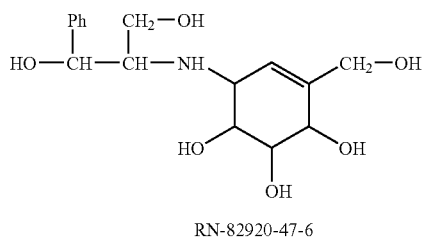

RN-82920-47-6

Horii, Satoshi; Kameda, Yukihiko; Fukase, Hiroshi. EP-49981-A1 p12

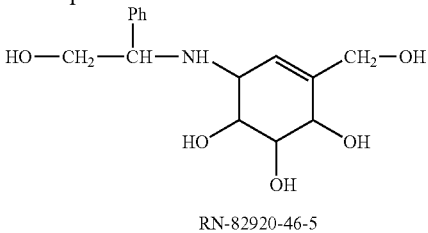

RN-82920-46-5

Horii, Satoshi; Kameda, Yukihiko; Fukase, Hiroshi. EP-49981-A1 p12

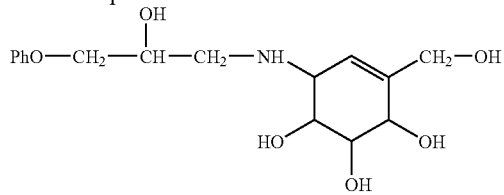

RN-82920-45-4

Horii, Satoshi; Kameda, Yukihiko; Fukase, Hiroshi. EP-49981-A1 p12

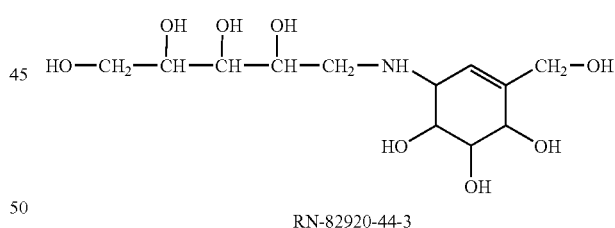

RN-82920-44-3

Horii, Satoshi; Kameda, Yukihiko; Fukase, Hiroshi. EP-49981-A1 p10

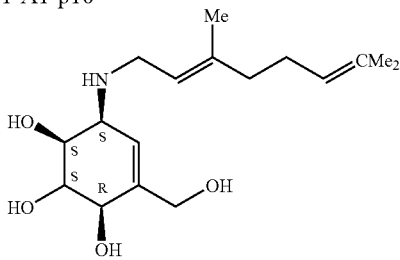

RN-82920-43-2

Horii, Satoshi; Kameda, Yukihiko; Fukase, Hiroshi. EP-49981-A1 p11

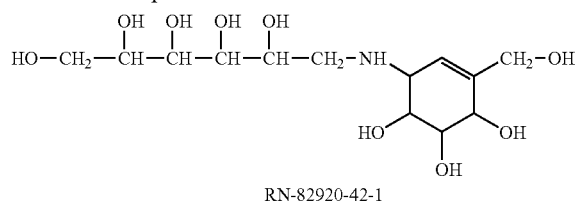

RN-82920-42-1

Horii, Satoshi; Kameda, Yukihiko; Fukase, Hiroshi. EP-49981-A1 p10

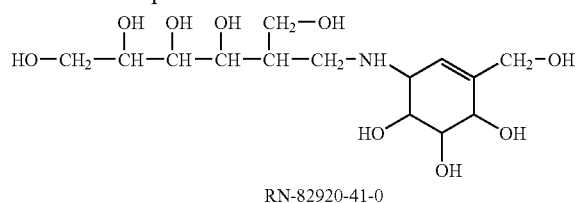

RN-82920-41-0

Horii, Satoshi; Kameda, Yukihiko; Fukase, Hiroshi. EP-49981-A1 p10

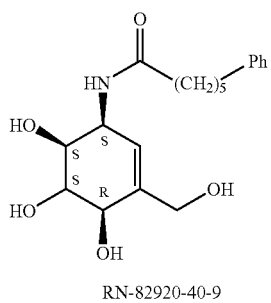

RN-82920-40-9

Horii, Satoshi; Kameda, Yukihiko; Fukase, Hiroshi. EP-49981-A1 p20

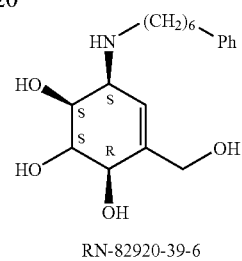

RN-82920-39-6

Horii, Satoshi; Kameda, Yukihiko; Fukase, Hiroshi. EP-49981-A1 p20

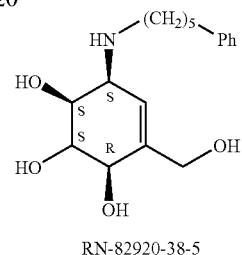

RN-82920-38-5

Horii, Satoshi; Kameda, Yukihiko; Fukase, Hiroshi. EP-49981-A1 p20

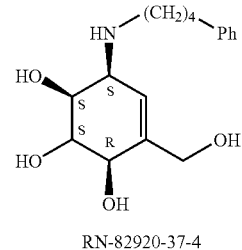

RN-82920-37-4

Horii, Satoshi; Kameda, Yukihiko; Fukase, Hiroshi. EP-49981-A1 p19

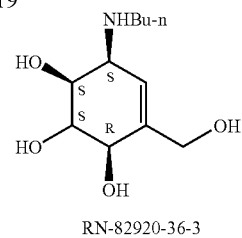

RN-82920-36-3

Horii, Satoshi; Kameda, Yukihiko; Fukase, Hiroshi. EP-49981-A1 p19

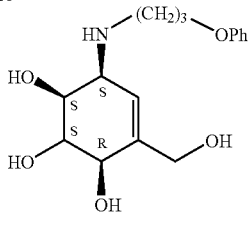

RN-82920-35-2

Horii, Satoshi; Kameda, Yukihiko; Fukase, Hiroshi. EP-49981-A1 p19

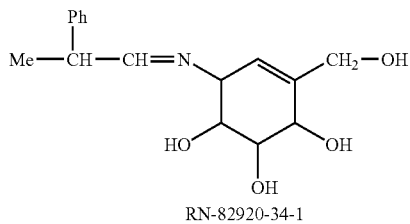

RN-82920-34-1

Horii, Satoshi; Kameda, Yukihiko; Fukase, Hiroshi. EP-49981-A1 p19

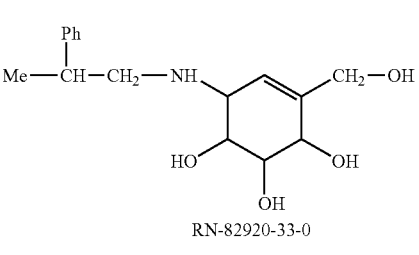

RN-82920-33-0

Horii, Satoshi; Kameda, Yukihiko; Fukase, Hiroshi.
EP-49981-A1 p19

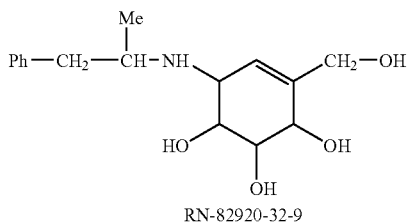

RN-82920-32-9

Horii, Satoshi; Kameda, Yukihiko; Fukase, Hiroshi.
EP-49981-A1 p18

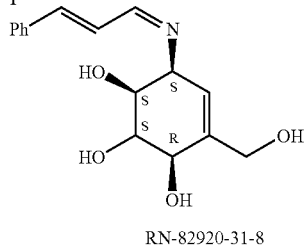

RN-82920-31-8

Horii, Satoshi; Kameda, Yukihiko; Fukase, Hiroshi.
EP-49981-A1 p18

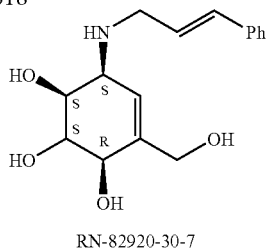

RN-82920-30-7

Horii, Satoshi; Kameda, Yukihiko; Fukase, Hiroshi.
EP-49981-A1 p18

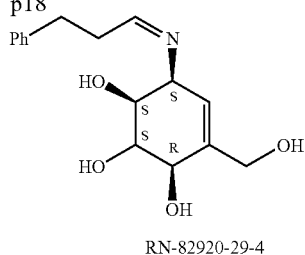

RN-82920-29-4

Horii, Satoshi; Kameda, Yukihiko; Fukase, Hiroshi.
EP-49981-A1 p18

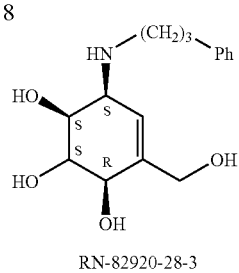

RN-82920-28-3

Horii, Satoshi; Kameda, Yukihiko; Fukase, Hiroshi.
EP-49981-A1 p18

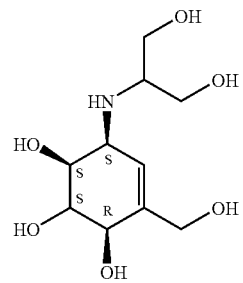

RN-82920-27-2

Horii, Satoshi; Kameda, Yukihiko; Fukase, Hiroshi.
EP-49981-A1 p18

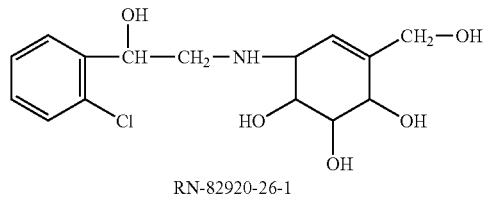

RN-82920-26-1

Horii, Satoshi; Kameda, Yukihiko; Fukase, Hiroshi.
EP-49981-A1 p17

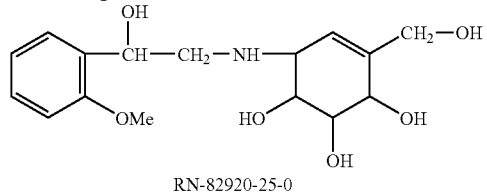

RN-82920-25-0

Horii, Satoshi; Kameda, Yukihiko; Fukase, Hiroshi.
EP-49981-A1 p17

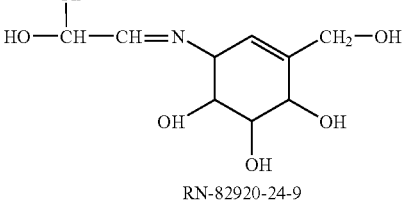

RN-82920-24-9

Horii, Satoshi; Kameda, Yukihiko; Fukase, Hiroshi.
EP-49981-A1 p17

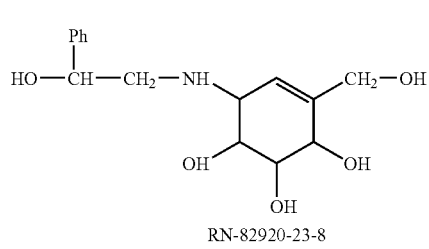

RN-82920-23-8

Horii, Satoshi; Kameda, Yukihiko; Fukase, Hiroshi.
EP-49981-A1 p17

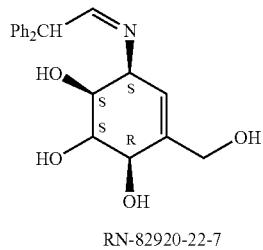

RN-82920-22-7

Horii, Satoshi; Kameda, Yukihiko; Fukase, Hiroshi.
EP-49981-A1 p16

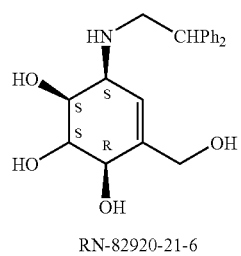

RN-82920-21-6

Horii, Satoshi; Kameda, Yukihiko; Fukase, Hiroshi.
EP-49981-A1 p16

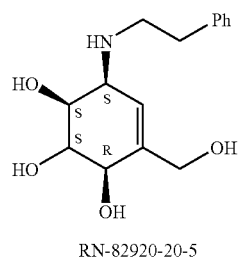

RN-82920-20-5

Horii, Satoshi; Kameda, Yukihiko; Fukase, Hiroshi.
EP-49981-A1 p16

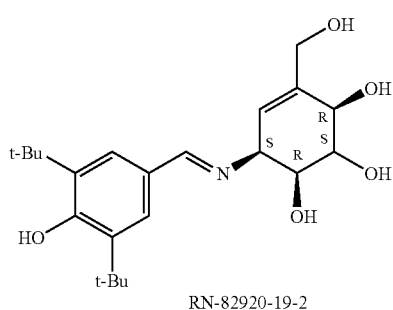

RN-82920-19-2

Horii, Satoshi; Kameda, Yukihiko; Fukase, Hiroshi.
EP-49981-A1 p15

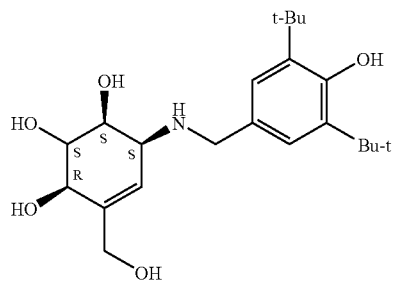

RN-82920-18-1

Horii, Satoshi; Kameda, Yukihiko; Fukase, Hiroshi.
EP-49981-A1 p15

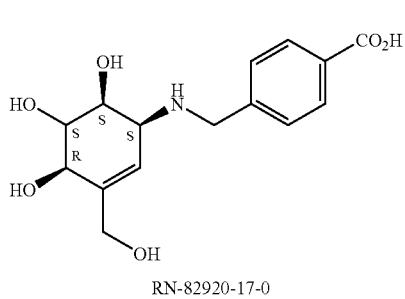

RN-82920-17-0

Horii, Satoshi; Kameda, Yukihiko; Fukase, Hiroshi.
EP-49981-A1 p15

RN-82920-16-9

Horii, Satoshi; Kameda, Yukihiko; Fukase, Hiroshi.
EP-49981-A1 p14

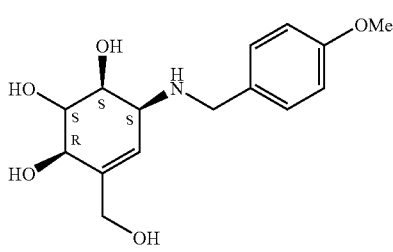

RN-82920-15-8

Horii, Satoshi; Kameda, Yukihiko; Fukase, Hiroshi. EP-49981-A1 p14

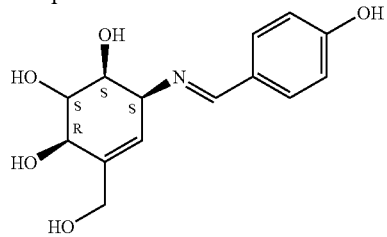

RN-82920-14-7

Horii, Satoshi; Kameda, Yukihiko; Fukase, Hiroshi. EP-49981-A1 p14

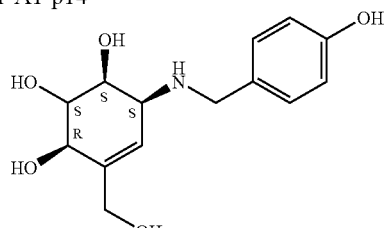

RN-82920-13-6

Horii, Satoshi; Kameda, Yukihiko; Fukase, Hiroshi. EP-49981-A1 p14

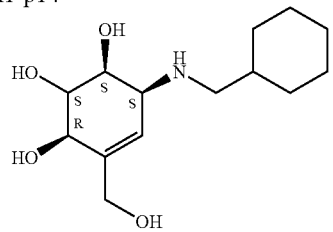

RN-82920-12-5

Horii, Satoshi; Kameda, Yukihiko; Fukase, Hiroshi. EP-49981-A1 p14

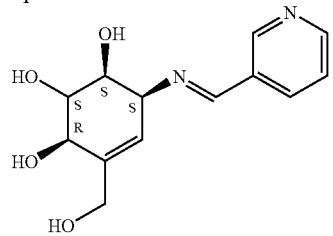

RN-82920-11-4

Horii, Satoshi; Kameda, Yukihiko; Fukase, Hiroshi. EP-49981-A1 p13

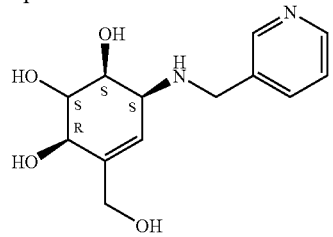

RN-82920-10-3

Horii, Satoshi; Kameda, Yukihiko; Fukase, Hiroshi. EP-49981-A1 p13

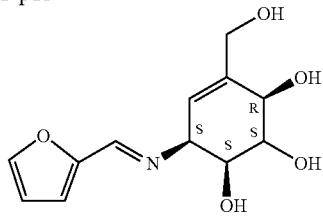

RN-82920-09-0

Horii, Satoshi; Kameda, Yukihiko; Fukase, Hiroshi. EP-49981-A1 p13

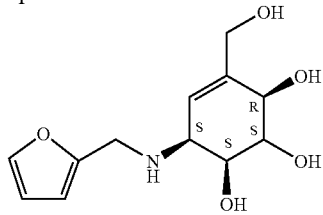

RN-82920-08-9

Horii, Satoshi; Kameda, Yukihiko; Fukase, Hiroshi. EP-49981-A1 p13

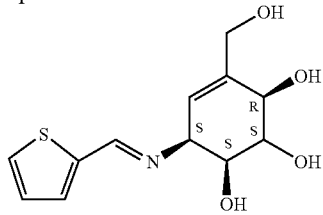

RN-82920-07-8

Horii, Satoshi; Kameda, Yukihiko; Fukase, Hiroshi. EP-49981-A1 p13

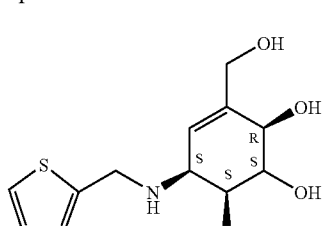

RN-82920-06-7

Horii, Satoshi; Kameda, Yukihiko; Fukase, Hiroshi. EP-49981-A1 p13

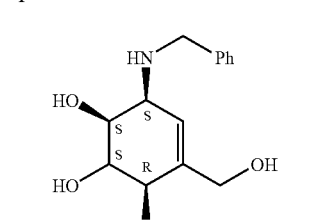

RN-82920-05-6

Horii, Satoshi; Kameda, Yukihiko; Fukase, Hiroshi. EP-49981-A1 p13

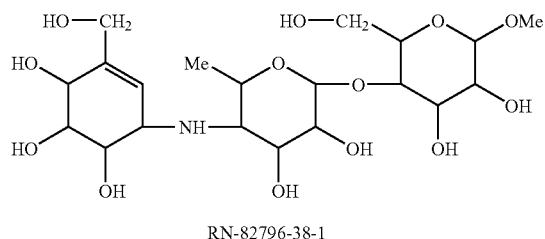

RN-82796-38-1

Meiji Seika Kaisha, Ltd., Japan JP-57024397-A2 p1

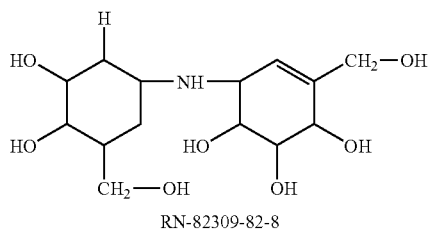

RN-82309-82-8

Ogawa, Seiichiro; Ogawa, Takao; Chida, Noritaka; Toyokuni, Tatsushi; Suami, Tetsuo. Chemistry Letters (1982), (5), 749–52 p751

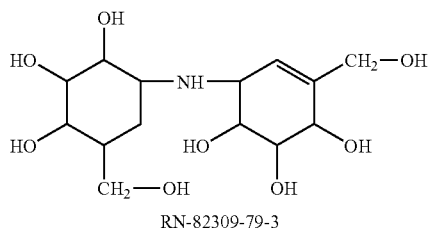

RN-82309-79-3

Ogawa, Seiichiro; Ogawa, Takao; Chida, Noritaka; Toyokuni, Tatsushi; Suami, Tetsuo. Chemistry Letters (1982), (5), 749–52 p751

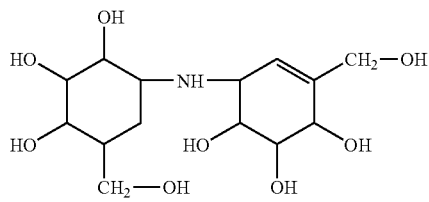

RN-82309-75-9

Ogawa, Seiichiro; Ogawa, Takao; Chida, Noritaka; Toyokuni, Tatsushi; Suami, Tetsuo. Chemistry Letters (1982), (5), 749–52 p751

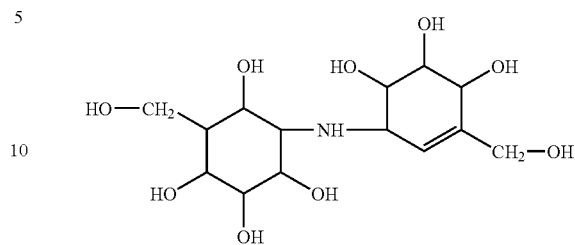

RN-81739-22-2

Ogawa, Seiichiro; Toyokuni, Tatsushi; Iwasawa, Yoshikazu; Abe, Yasuo; Suami, Tetsuo. Chemistry Letters (1982), (3), 279–82 p279

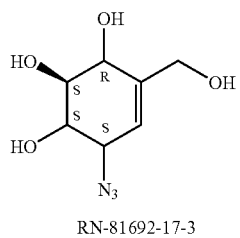

RN-81692-17-3

Ogawa, Seiichiro; Toyokuni, Tatsushi; Iwasawa, Yoshikazu; Abe, Yasuo; Suami, Tetsuo. Chemistry Letters (1982), (3), 279–82 p280

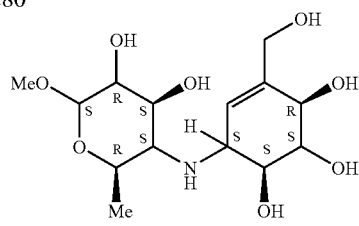

RN-80943-41-4

Meiji Seika Kaisha, Ltd., Japan JP-57024397-A2 p1

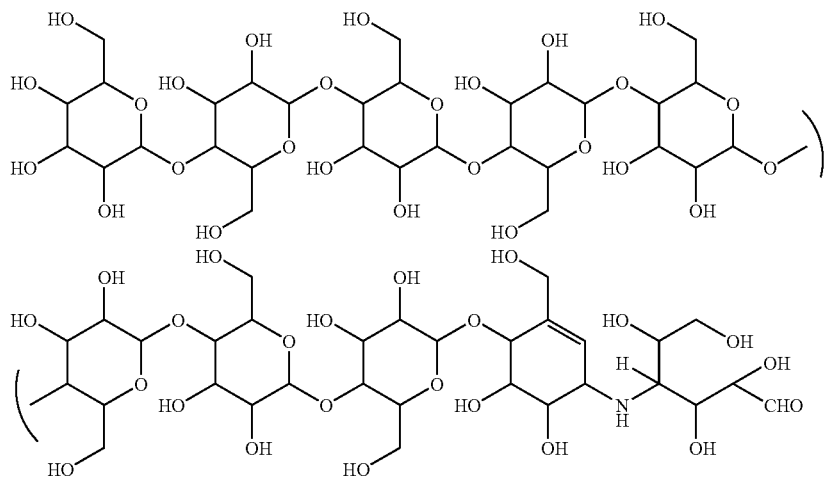

RN-80531-33-5

Taisho Pharmaceutical Co., Ltd., Japan. JP-56125398-A2 p1
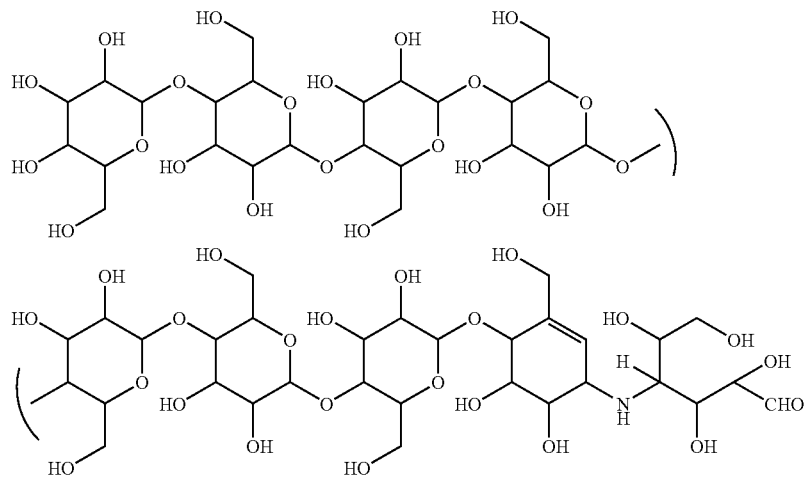
RN-80531-32-4
Taisho Pharmaceutical Co., Ltd., Japan. JP-56125398-A2 p1
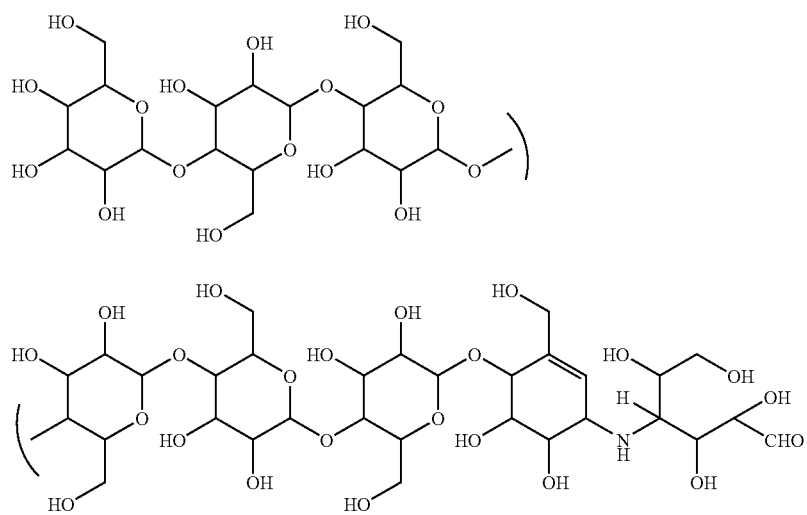
RN-80531-31-3
Taisho Pharmaceutical Co., Ltd., Japan. JP-56125398-A2 p1
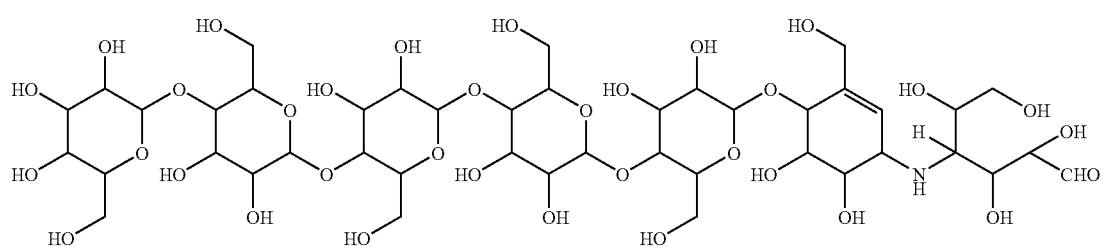
RN-80521-30-2

Taisho Pharmaceutical Co., Ltd., Japan. JP-56125398-A2 p1
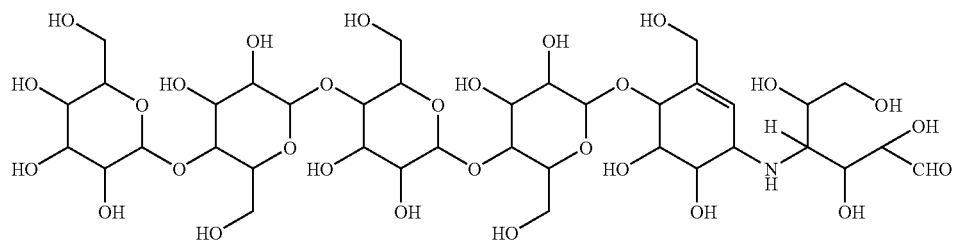
RN-80521-29-9
Taisho Pharmaceutical Co., Ltd., Japan. JP-56125398-A2 p1
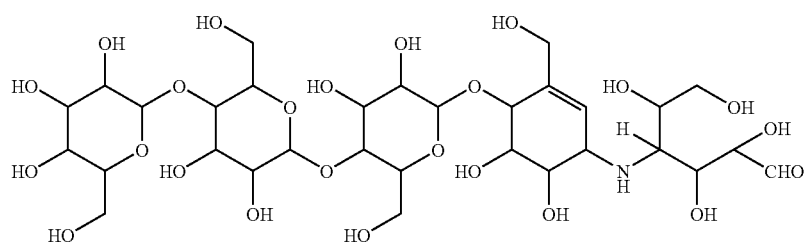
RN-80521-28-8
Taisho Pharmaceutical Co., Ltd., Japan. JP-56125398-A2 p1
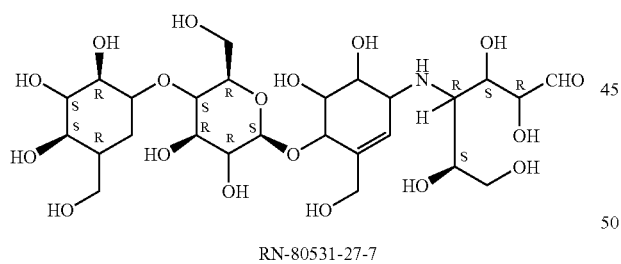
RN-80531-27-7
Taisho Pharmaceutical Co., Ltd., Japan. JP-56125398-A2 p1
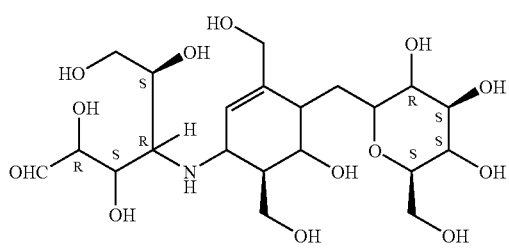
RN-80531-26-6
Taisho Pharmaceutical Co., Ltd., Japan. JP-56125398-A2 p1
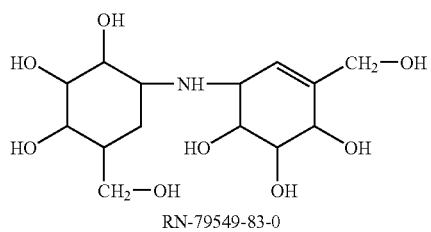
RN-79549-83-0
Ogawa, Seiichiro; Toyakuni, Tatsushi; Suami, Tetsuo. Chemistry Letters (1981), (7), 947–50.
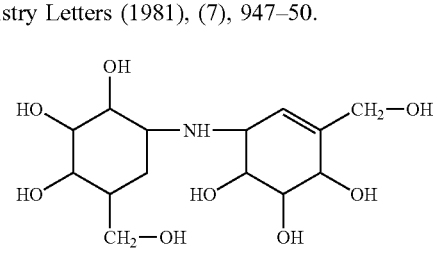
RN-79549-82-9

Ogawa, Seiichiro; Toyokuni, Tatsushi; Suami, Tetsuo. Chemistry Letters (1981), (7), 947–50.

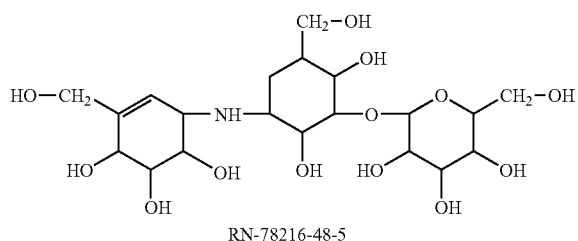

RN-78216-48-5

Takeda Chemical Industries, Ltd., Japan JP-56012399

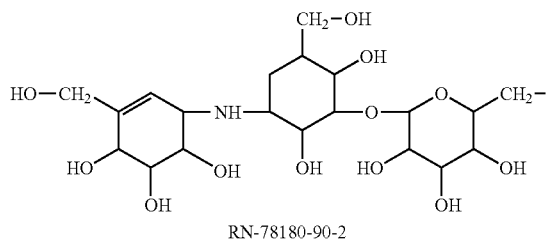

RN-78180-90-2

Asano, Naoki; Kameda, Yukihiko; Matsui, Katsuhiko. Journal of Antibiotics (1991), 44(12), 1406–16 compound 3a p1407

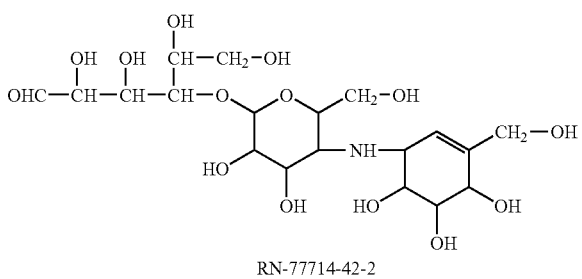

RN-77714-42-2

Mueller, L.; Junge, B.; Frommer, W.; Schmidt, D.; Truscheit, E. Inst. Biochem., Bayer A.-G., Wuppertal, Fed. Rep. Ger. Editor(s): Brodbeck, Urs. Enzyme Inhibitors, Proc. Meet. (1980), 109–22. Publisher: Verlag Chain p117

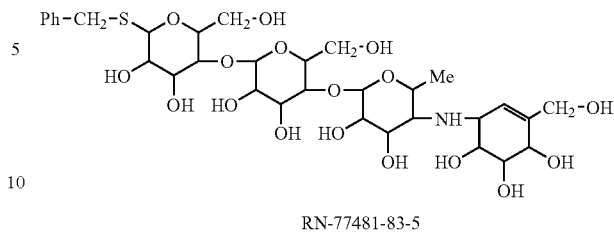

RN-77481-83-5

Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem. Diagram 15 p 135

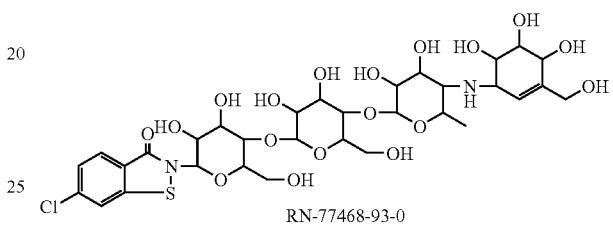

RN-77468-93-0

Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem Diagram 16 p136

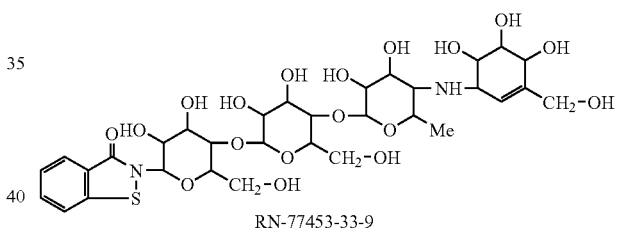

RN-77453-33-9

Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem diagram 16 p136

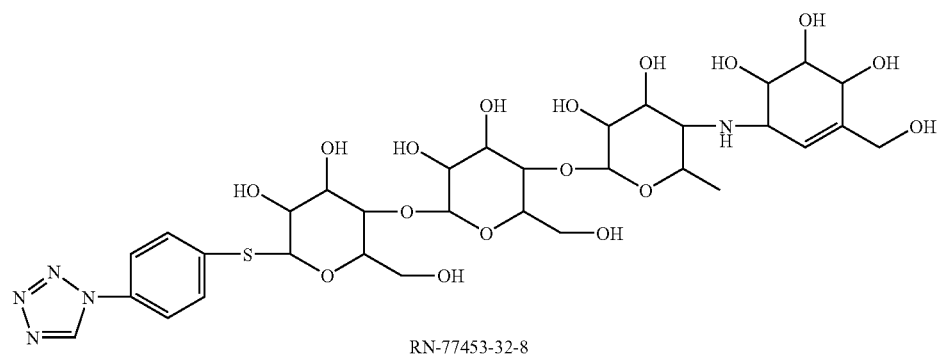

RN-77453-32-8

Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem diagram 15 p135

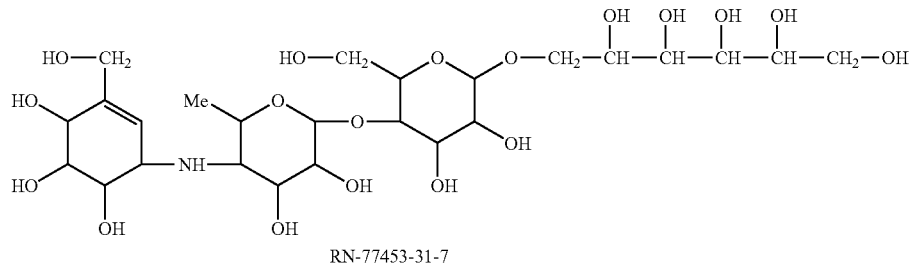

RN-77453-31-7

Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem

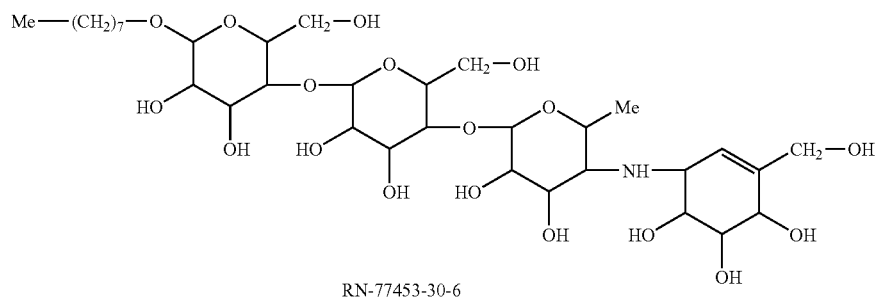

RN-77453-30-6

Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem diagram 13 p134

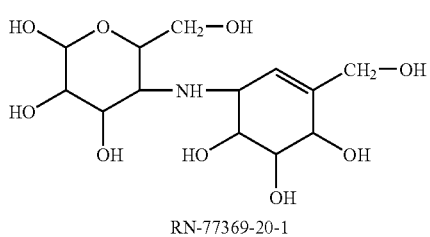

RN-77369-20-1

Mueller, L.; Junge, B.; Frommer, W.; Schmidt, D.; Truscheit, E. Inst. Biochem., Bayer A.-G., Wuppertal, Fed. Rep. Ger. Editor(s): Brodbeck, Urs. Enzyme Inhibitors, Proc. Meet. (1980), 109–22. Publisher: Verlag Chain

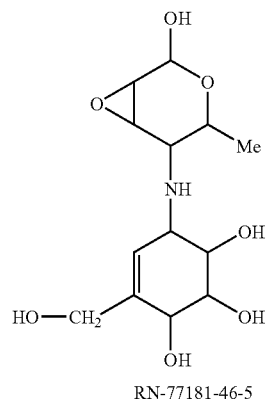

RN-77181-46-5

Ajinomoto Co., Inc., Japan. JP-55157595

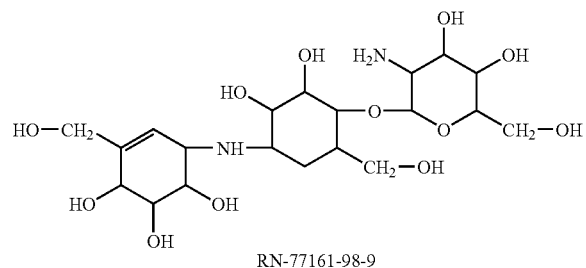

RN-77161-98-9

Takeda Chemical Industries, Ltd., Japan JP-55133393

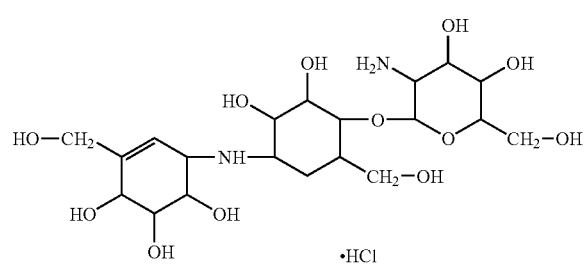

RN-73495-52-0

Hasegawa, Akira; Kobayashi, Toshiyuki; Hibino, Hideyuki; Kiso, Makoto. Dep. Agric. Chem., Gifu Univ., Gifu, Japan. Agricultural and Biological Chemistry (1980), 44(1), 143–7 p144

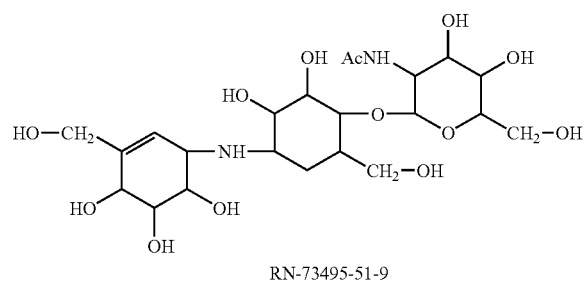

RN-73495-51-9

Hasegawa, Akira; Kobayashi, Toshiyuki; Hibino, Hideyuki; Kiso, Makoto. Dep. Agric. Chem., Gifu Univ., Gifu, Japan. Agricultural and Biological Chemistry (1980), 44(1), 143–7 p144

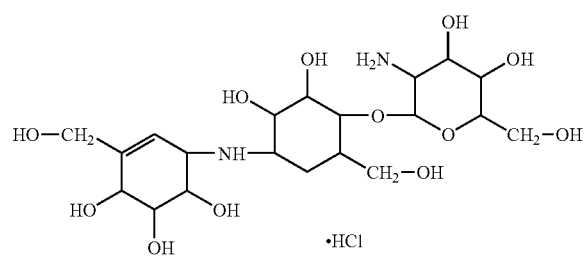

RN-73469-82-6

Hasegawa, Akira; Kobayashi, Toshiyuki; Hibino, Hideyuki; Kiso, Makoto. Dep. Agric. Chem., Gifu Univ., Gifu, Japan. Agricultural and Biological Chemistry (1980), 44(1), 143–7 p144

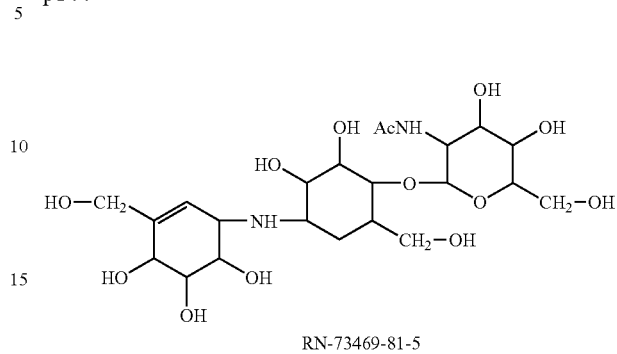

RN-73469-81-5

Hasegawa, Akira; Kobayashi, Toshiyuki; Hibino, Hideyuki; Kiso, Makoto. Dep. Agric. Chem., Gifu Univ., Gifu, Japan. Agricultural and Biological Chemistry (1980), 44(1). 143–7 p144

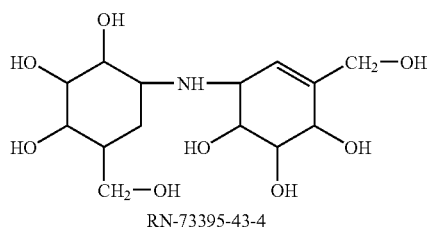

RN-73395-43-4

Kameda Yukihiko. Takeda Chemical Industries, Ltd., Japan JP-55000308

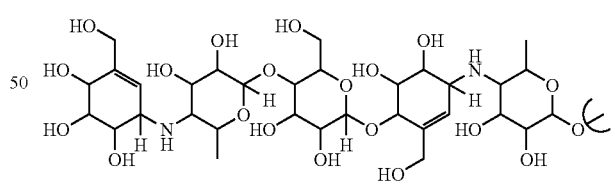

RN-71884-70-3

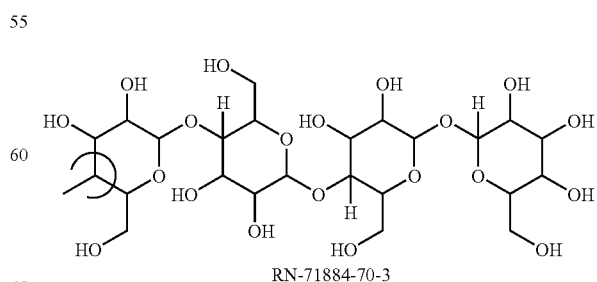

Y. Suhara et. al. U.S. Pat. No. 4,273,765
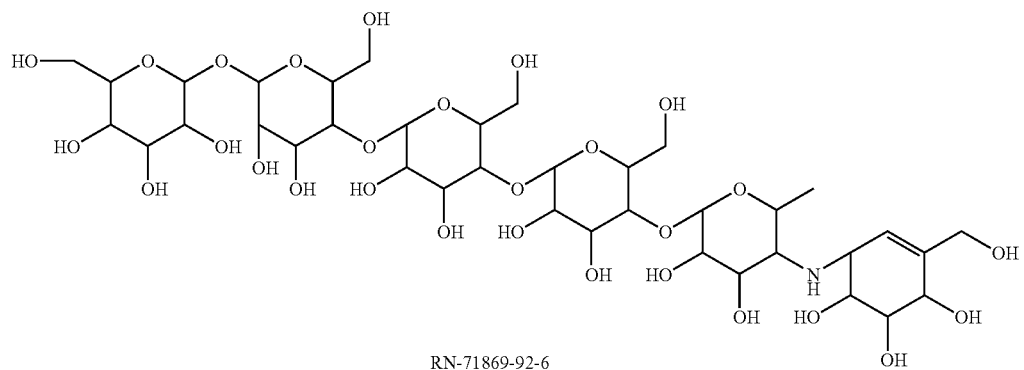
RN-71869-92-6
Y. Suhara et. al. U.S. Pat. No. 4,273,765
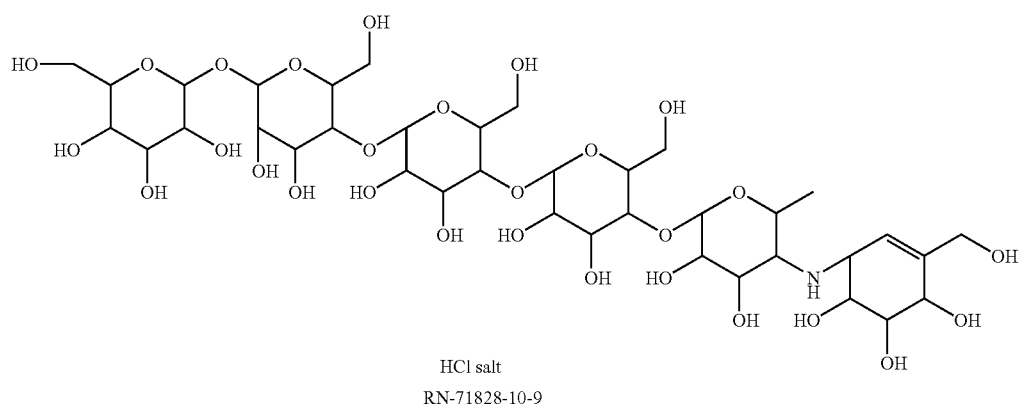
HCl salt
RN-71828-10-9
Y. Suhara et. al. U.S. Pat. No. 4,273,765
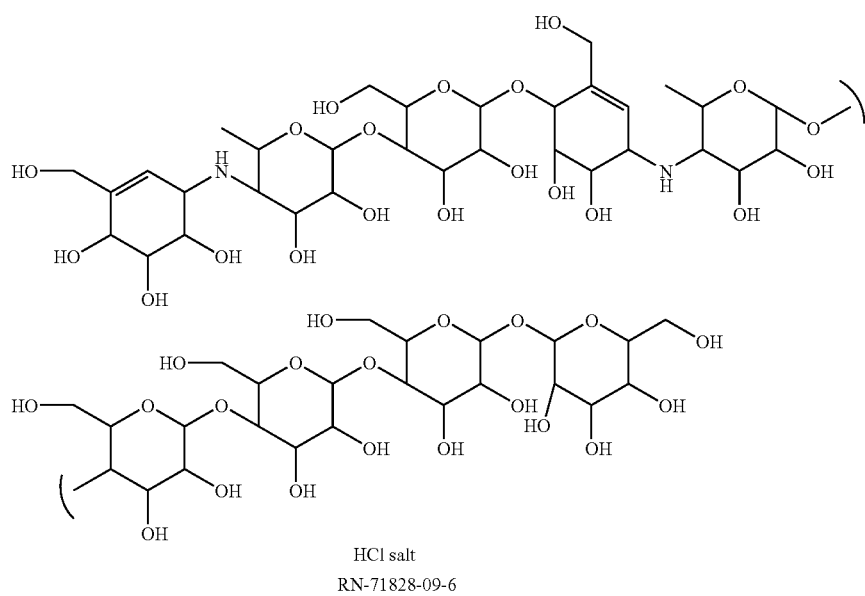
HCl salt
RN-71828-09-6

Y. Suhara et. al. U.S. Pat. No. 4,273,765

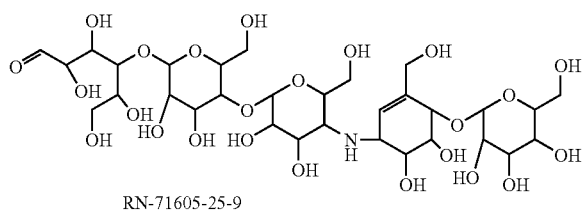

RN-71605-25-9

Otani, Masaru; Saito, Tetsu; Satoi, Shuzo; Mizoguchi, Junzo; Muto, Naoki. Toyo Jozo Co., Ltd., Japan DE-2855409

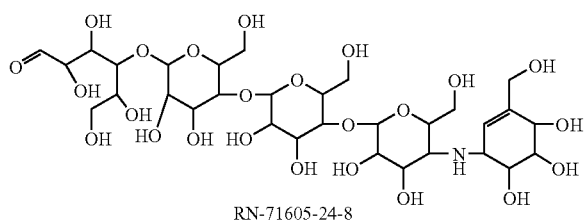

RN-71605-24-8

Otani, Masaru; Saito, Tetsu; Satoi, Shuzo; Mizoguchi, Junzo; Muto, Naoki. Toyo Jozo Co., Ltd., Japan DE-2855409

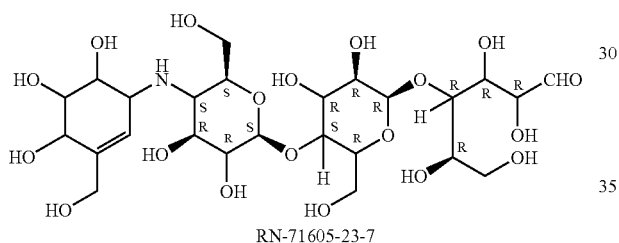

RN-71605-23-7

Otani, Masaru; Saito, Tetsu; Satoi, Shuzo; Mizoguchi, Junzo; Muto, Naoki. Toyo Jozo Co., Ltd., Japan DE-2855409

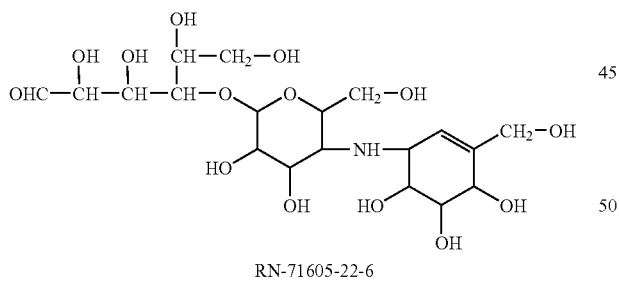

RN-71605-22-6

Otani, Masaru; Saito, Tetsu; Satoi, Shuzo; Mizoguchi, Junzo; Muto, Naoki. Toyo Jozo Co., Ltd., Japan DE-2855409

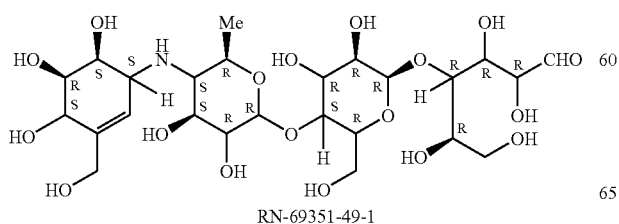

RN-69351-49-1

E. Rauenbusch et. al. U.S. Pat. No. 4,174,439

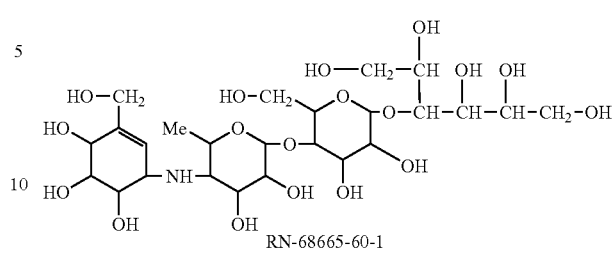

RN-68665-60-1

B. Junge et. al. DE-2658562 p65

Component Number 1

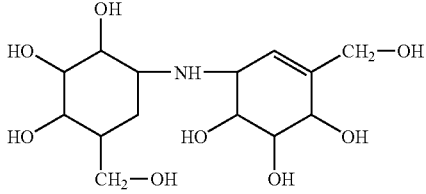

Component Number 2

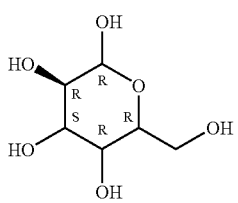

RN-68422-39-9

Kameda, Yukihiko; Asano, Naoki; Hashimoto, Tadashi. Journal of Antibiotics (1978), 31(9), 936–8. p 936

Component Number 1

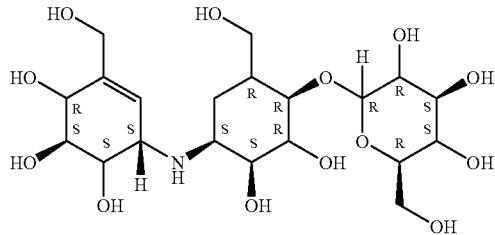

Component Number 2

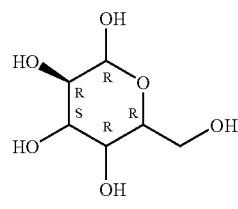

RN-68422-38-8

Kameda, Yukihiko; Asano, Naoki; Hashimoto, Tadashi. Journal of Antibiotics (1978), 31(9), 936–8. p936
Component Number 1
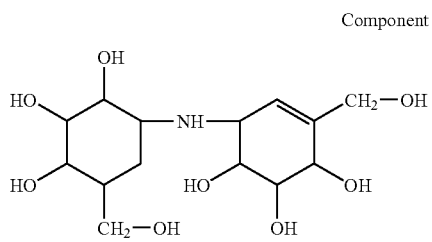
Component Number 2
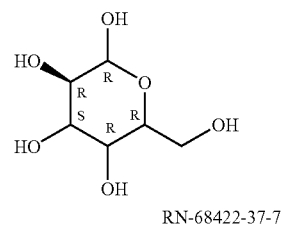
RN-68422-37-7
Kameda, Yukihiko; Asano, Naoki; Hashimoto, Tadashi. Journal of Antibiotics (1978), 31(9), 936–8. p937
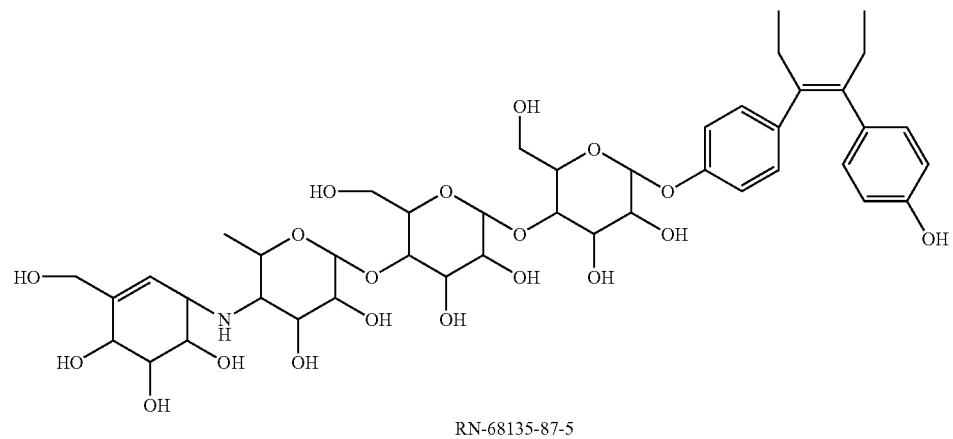
RN-68135-87-5
B. Junge et. al. DE-2658562 p57
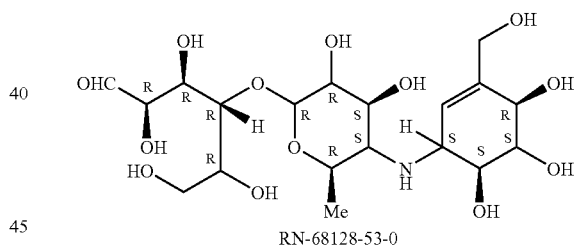
RN-68128-53-0
B. Junge et. al. DE-2658562 p27
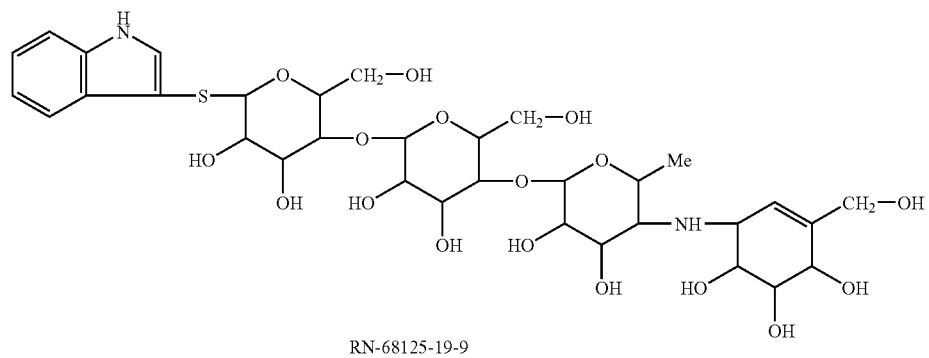
RN-68125-19-9

B. Junge et. al. DE-2658562
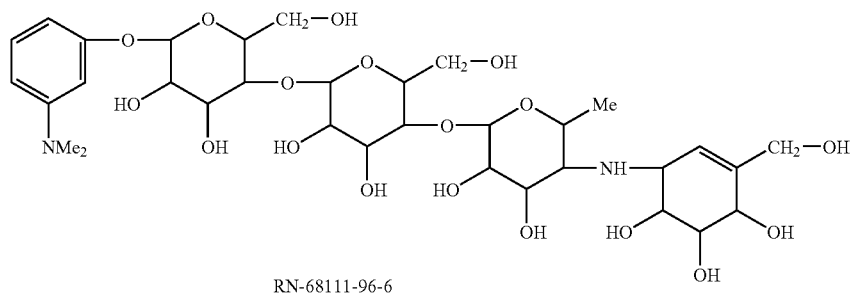
RN-68111-96-6
B. Junge et. al. DE-2658562 p69
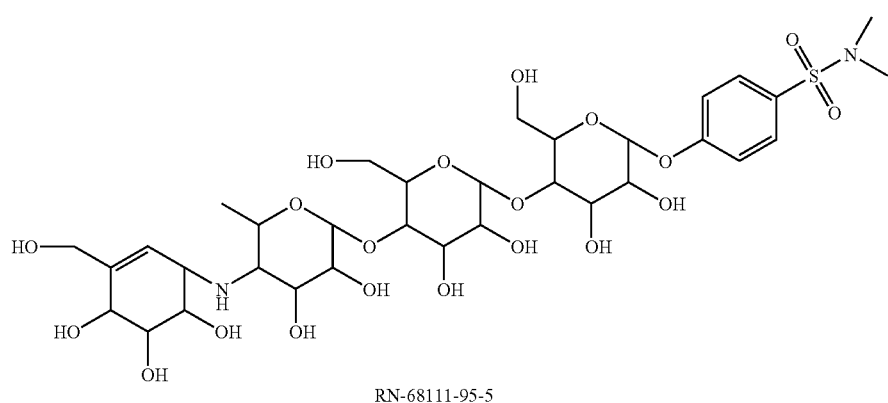
RN-68111-95-5
B. Junge et. al. DE-2658562 p69
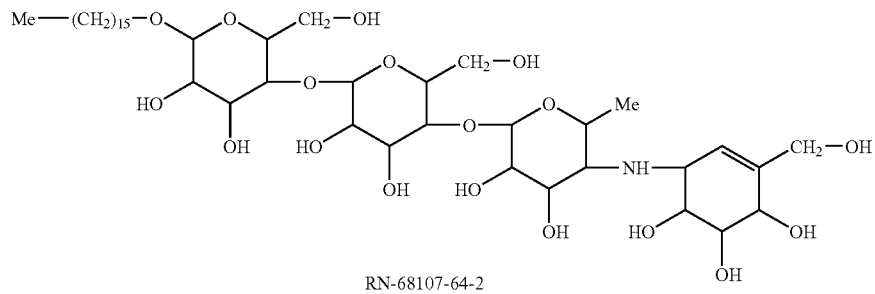
RN-68107-64-2
B. Junge et. al. DE-2658562 p62
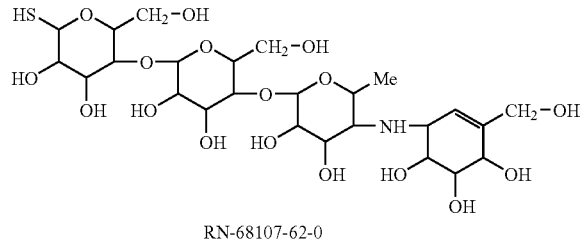
RN-68107-62-0

B. Junge et. al. DE-2658562 p31
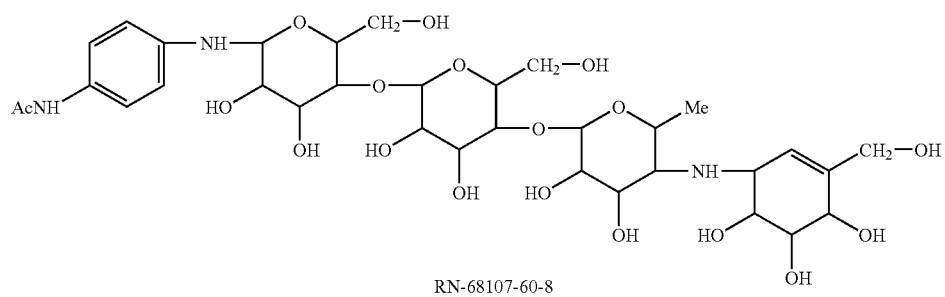
RN-68107-60-8
B. Junge et. al. DE-2658562
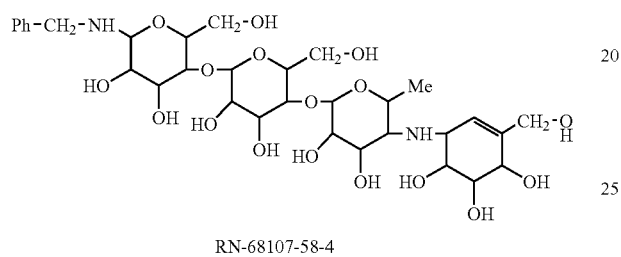
RN-68107-58-4
B. Junge et. al. DE-2658562 p73
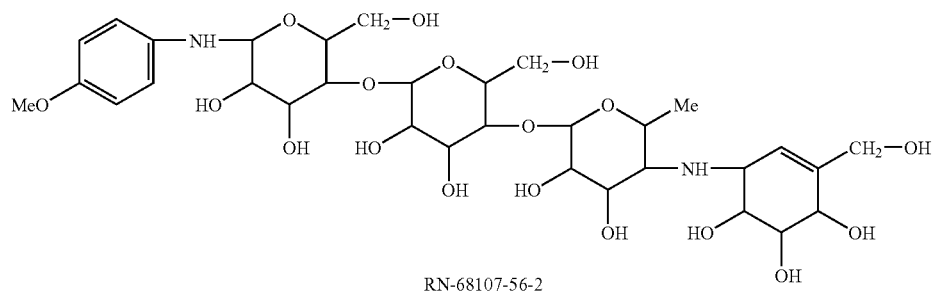
RN-68107-56-2
Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem. Diagram 16 p 136
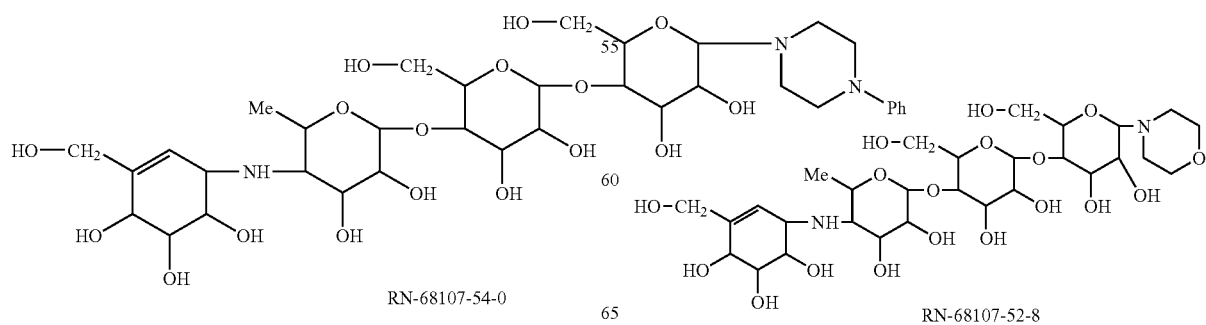
RN-68107-54-0  RN-68107-52-8

Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem. Diagram 16 p 136
B. Junge et. al. DE-2658562 p73

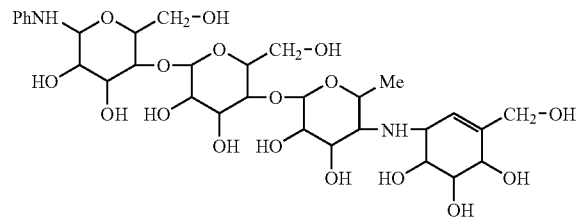

RN-68107-50-6

Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem. Diagram 15 p 135

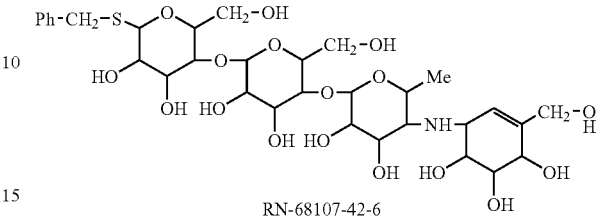

RN-68107-42-6

B. Junge et. al. DE-2658562 p73

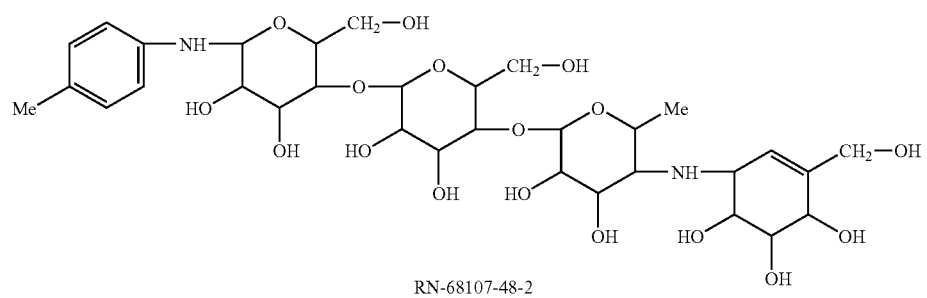

RN-68107-48-2

B. Junge et. al. DE-2658562 p72

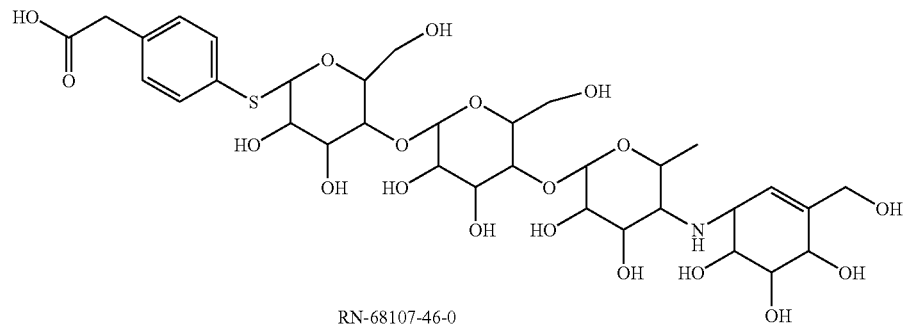

RN-68107-46-0

B. Junge et. al. DE-2658562

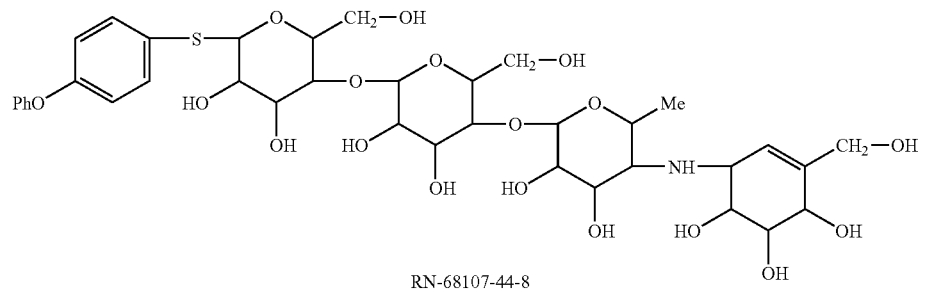

RN-68107-44-8

B. Junge et. al. DE-2658562 p72
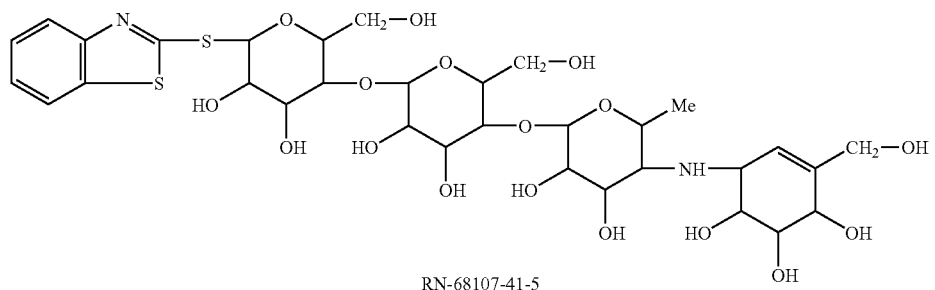
RN-68107-41-5
B. Junge et. al. DE-2658562 p71
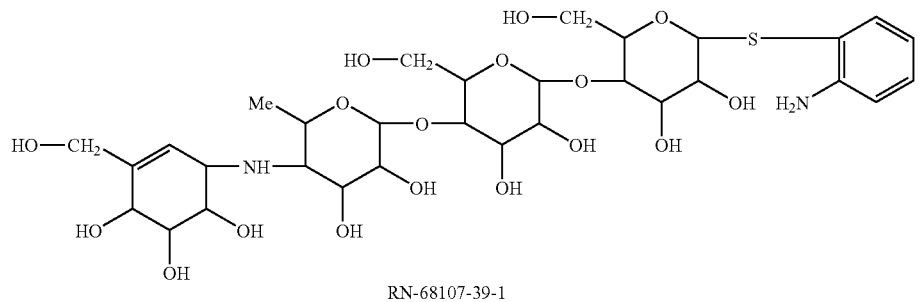
RN-68107-39-1
B. Junge et. al. DE-2658562 p71
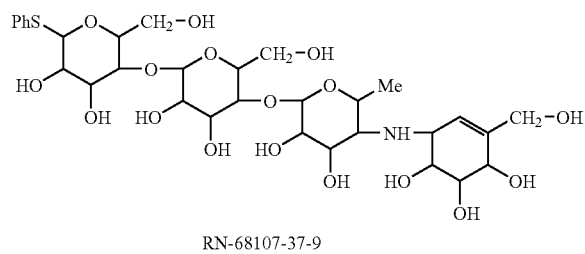
RN-68107-37-9
B. Junge et. al. DE-2658562 p70
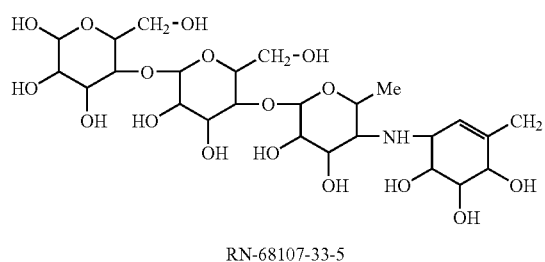
RN-68107-33-5
Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem. P127
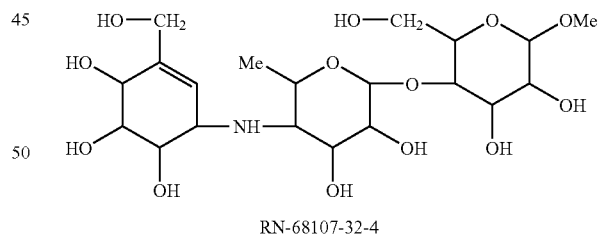
RN-68107-32-4
B. Junge et. al. DE-2658562 p63
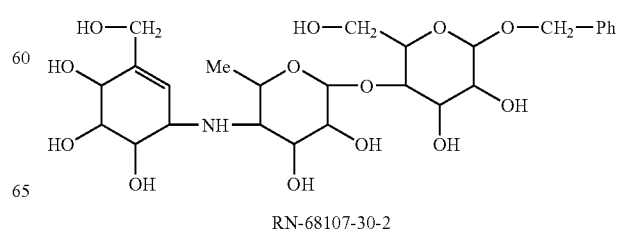
RN-68107-30-2

B. Junge et. al. DE-2658562 p63
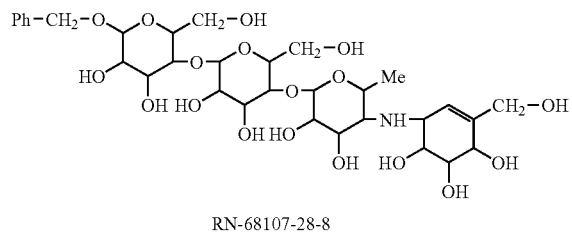
RN-68107-28-8
B. Junge et. al. DE-2658562 p63
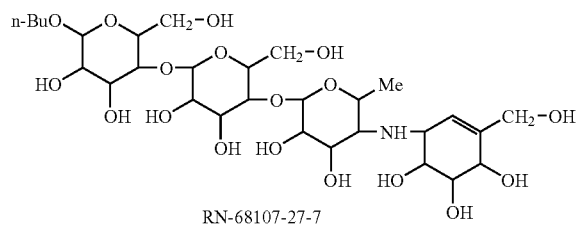
RN-68107-27-7
B. Junge et. al. DE-2658562 p61
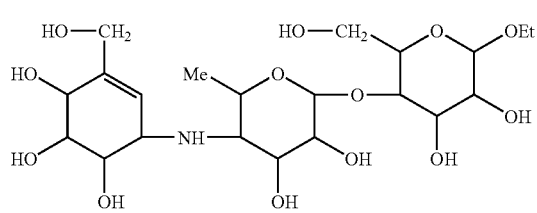
RN-68095-99-8
B. Junge et. al. DE-2658562 p61
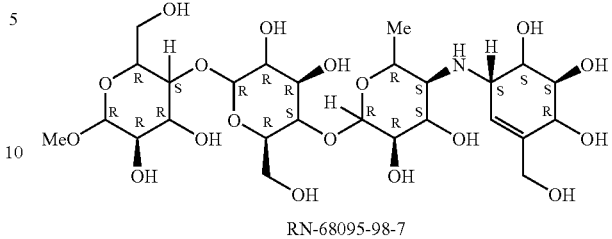
RN-68095-98-7
B. Junge et. al. DE-2658562 p59
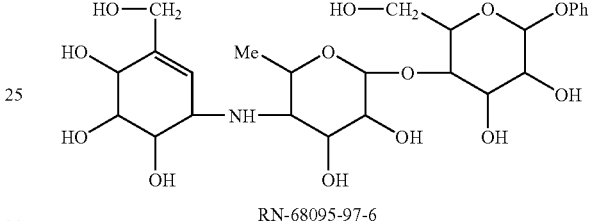
RN-68095-97-6
B. Junge et. al. DE-2658562 p59
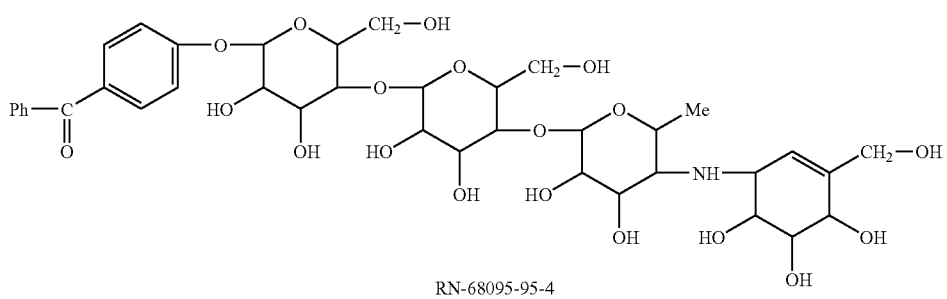
RN-68095-95-4
B. Junge et. al. DE-2658562 p70
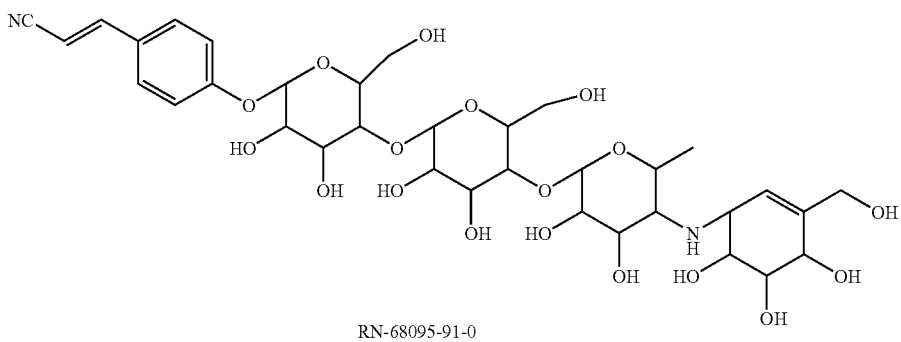
RN-68095-91-0

Junge, B.; Boeshagen, H.; Stoltefuss, J.; Mueller, L. Inst. Biochem., Bayer A.-G., Wuppertal, Fed. Rep. Ger. Editor(s): Brodbeck, Urs. Enzyme Inhibitors, Proc. Meet. (1980), 123–37. Publisher: Verlag Chem. Diagram 14 p 135
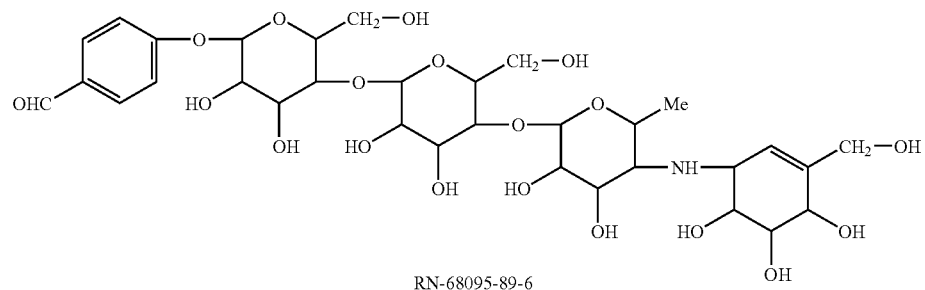
B. Junge et. al. DE-2658562
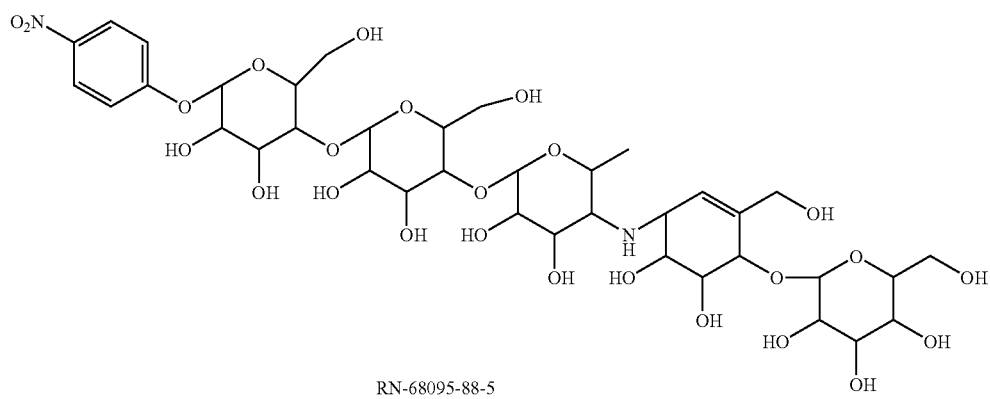
B. Junge et. al. DE-2658562 p53
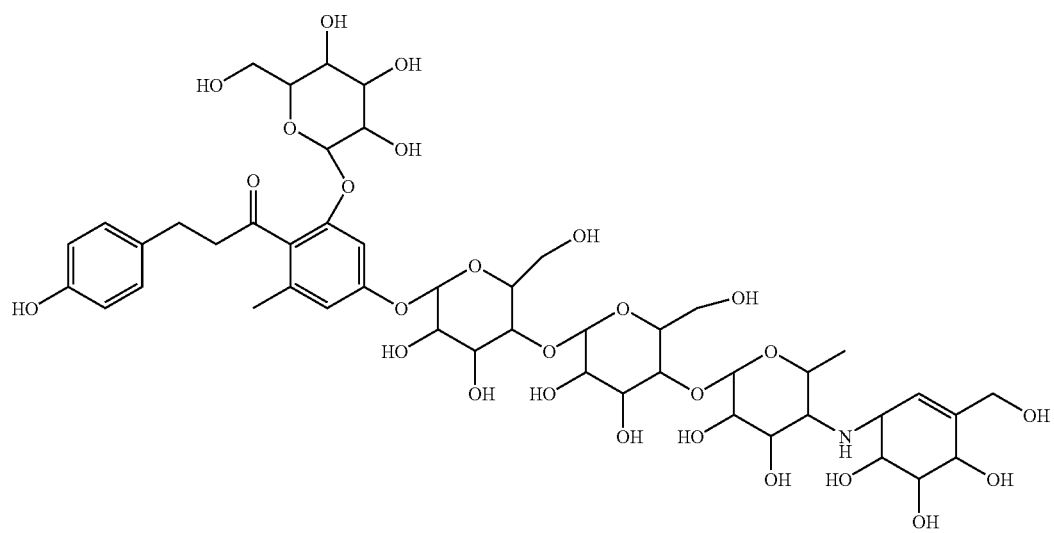

B. Junge et. al. DE-2658562 p57
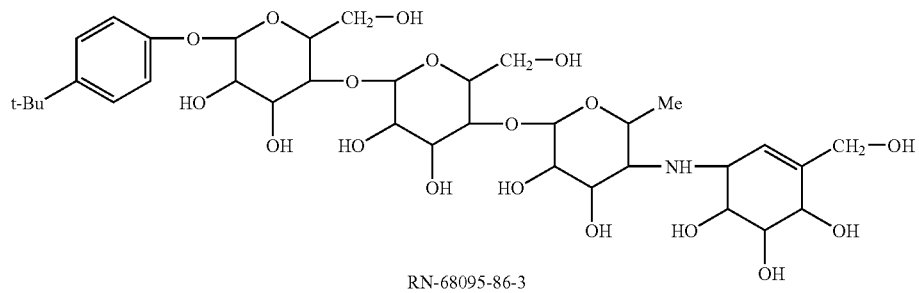
RN-68095-86-3
B. Junge et. al. DE-2658562 p57
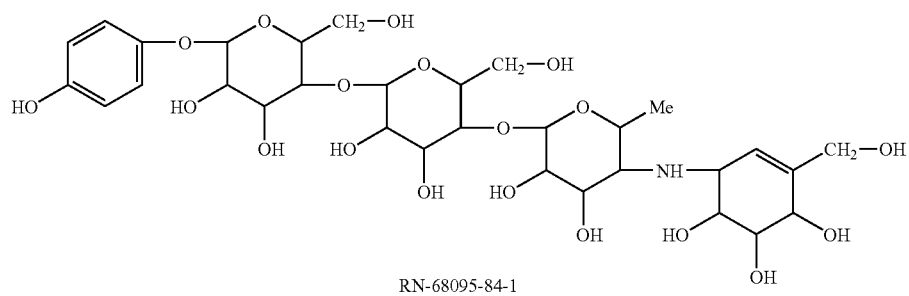
RN-68095-84-1
B. Junge et. al. DE-2658562 p56
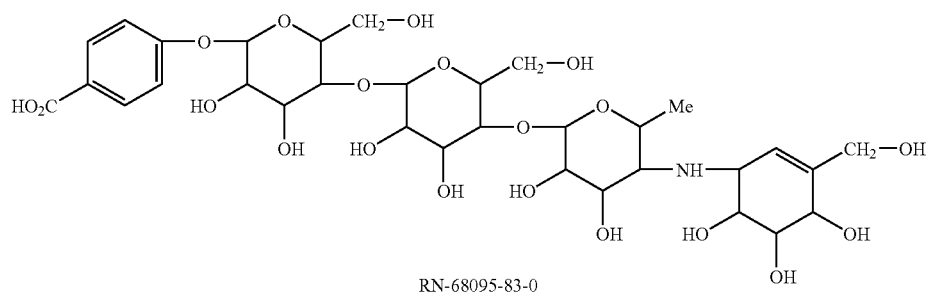
RN-68095-83-0
B. Junge et. al. DE-2658562 p56
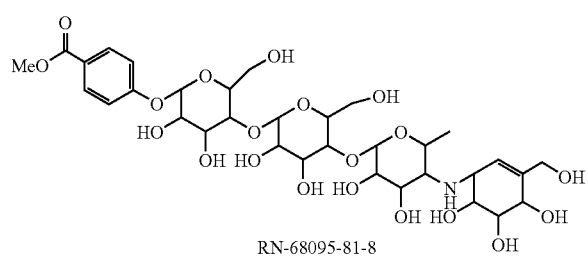
RN-68095-81-8
B. Junge et. al. DE-2658562 p56
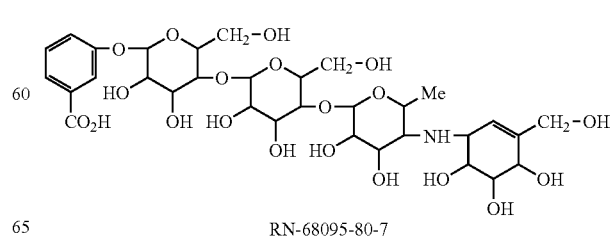
RN-68095-80-7

B. Junge et. al. DE-2658562 p55
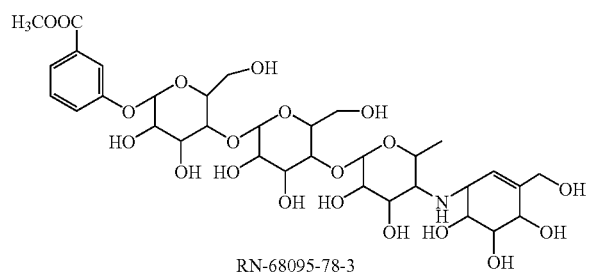
RN-68095-78-3
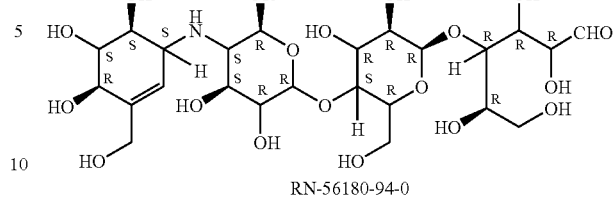
RN-56180-94-0
B. Junge et. al. DE-2658562 p55
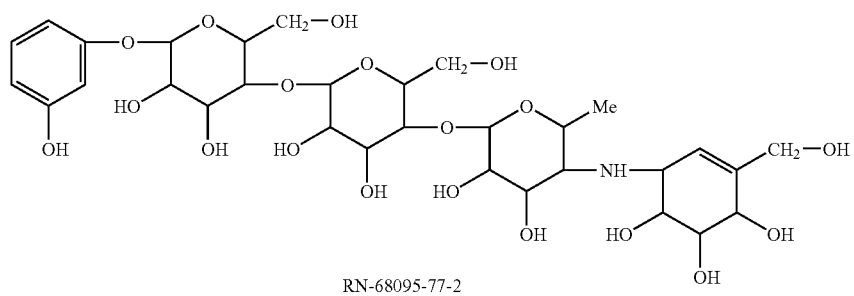
RN-68095-77-2
B. Junge et. al. DE-2658562 p54
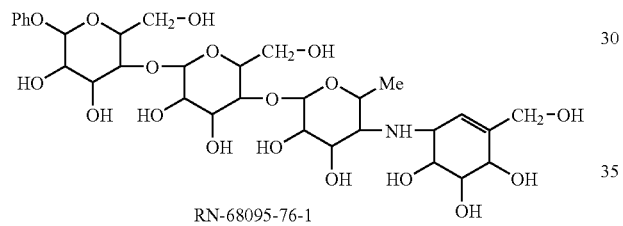
RN-68095-76-1
B. Junge et. al. DE-2658562 p54
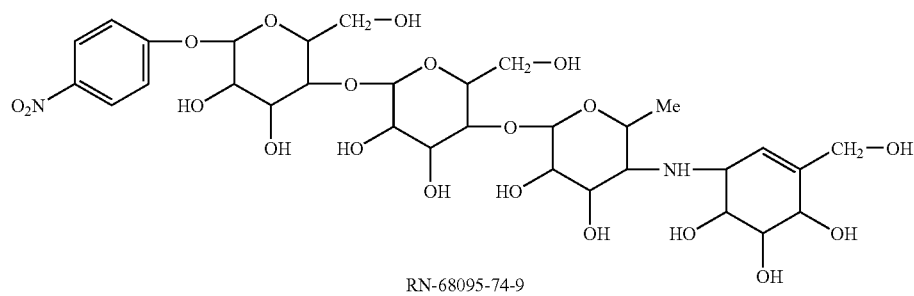
RN-68095-74-9
B. Junge et. al. DE-2658562 p53
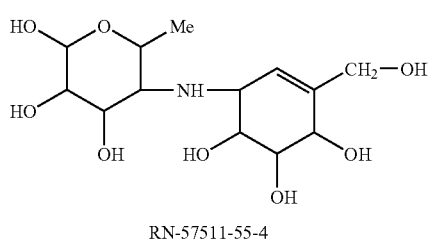
RN-57511-55-4
Frommer, Werner; Junge, Bodo; Keup, Uwe; Mueller, Lutz; Puls, Walter; Schmidt, Delf. U.S. Pat. No. 4,062,950 example 14
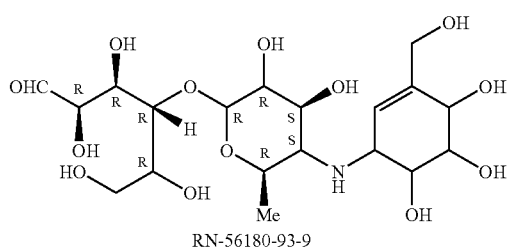
RN-56180-93-9

Frommer, Werner; Junge, Bodo; Keup, Uwe; Mueller, Lutz; Puls, Walter; Schmidt, U.S. Pat. No. 4,062,950 example 15

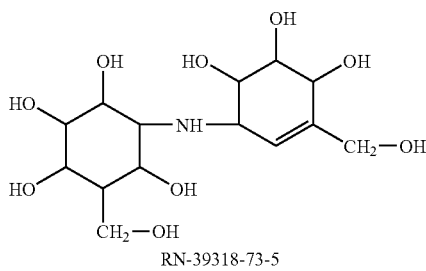
RN-39318-73-5

Asano N; Takeuchi M; Kameda Y; Matsui K; Kono Y
JOURNAL OF ANTIBIOTICS (1990 June), 43(6), 722–6
p723

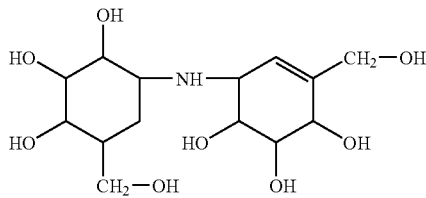
RN-38665-10-0

Asano N; Takeuchi M; Kameda Y; Matsui K; Kono Y
JOURNAL OF ANTIBIOTICS (1990 June), 43(6), 722–6
p723

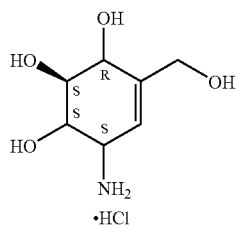
·HCl
RN-38231-88-8

Kameda, Yukihiko; Horii, Satoshi. Journal of the Chemical Society, Chemical Communications (1972), (12), 746–7 p746

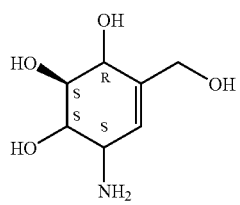
RN-38231-86-6

Chen, Xiaolong; Fan, Yongxian; Zheng, Yuguo; Shen, Yinchu. Chemical Reviews (Washington, D.C., United States) (2003), 103(5), 1955–1977

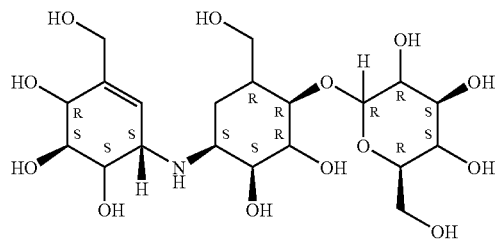
RN-37248-47-8

Horii, Satoshi; Kameda, Yukihiko. Journal of the Chemical Society, Chemical Communications (1972), (12), 747–8.

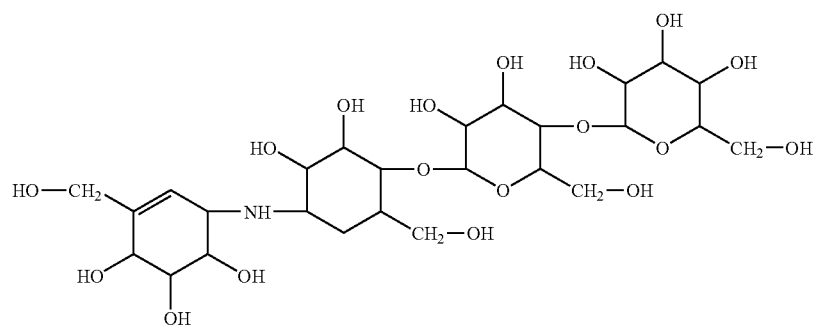
RN-12650-71-4

Horii, Satoshi; Kameda, Yukihiko; Kawahara, Kunio. Journal of Antibiotics (1972), 25(1), 48–53 p51

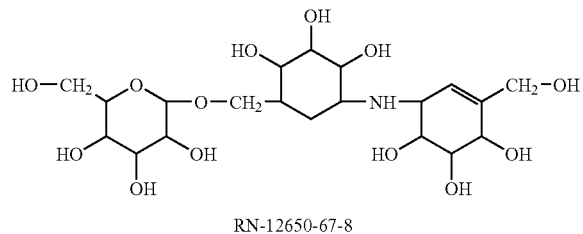

RN-12650-67-8

Kim, Jung Woo; Lee, Kwang Moo; Chun, Hyoung Sik; Kim, Jong Gwan; Chang, Hung Bae; Kim, Sun Ho; Min, Kyeong Bok; Moon WO-9620945-A1 p10

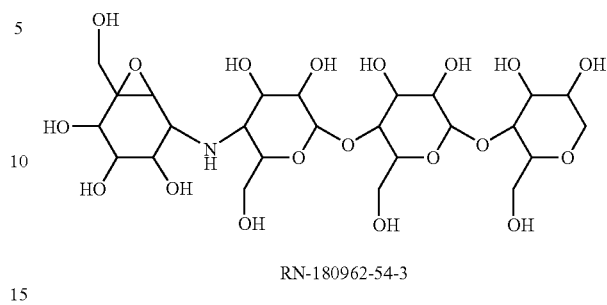

RN-180962-54-3

Horii, Satoshi; Kameda, Yukihiko; Kawahara, Kunjo. Journal of Antibiotics (1972), 25(1), 48–53 p51

Kim, Jung Woo; Lee, Kwang Moo; Chun, Hyoung Sik; Kim, Jong Gwan; Chang, Hung Bae; Kim, Sun Ho; Min, Kyeong Bok; Moon WO-9620945-A1 p10

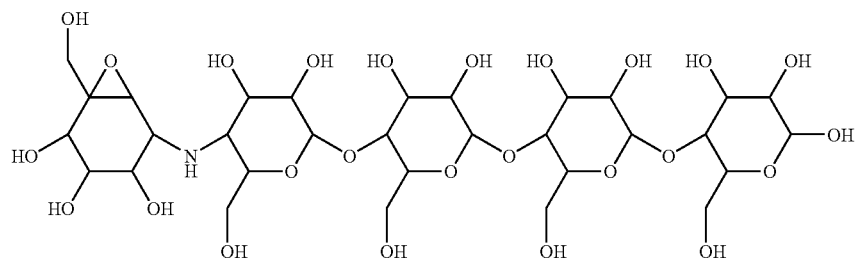

RN-180962-56-5

Kim, Jung Woo; Lee, Kwang Moo; Chun, Hyoung Sik; Kim, Jong Gwan; Chang, Hung Bae; Kim, Sun Ho; Min, Kyeong Bok; Moon WO-9620945-A1 p10

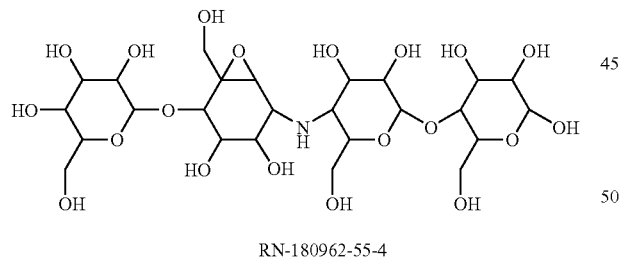

RN-180962-55-4

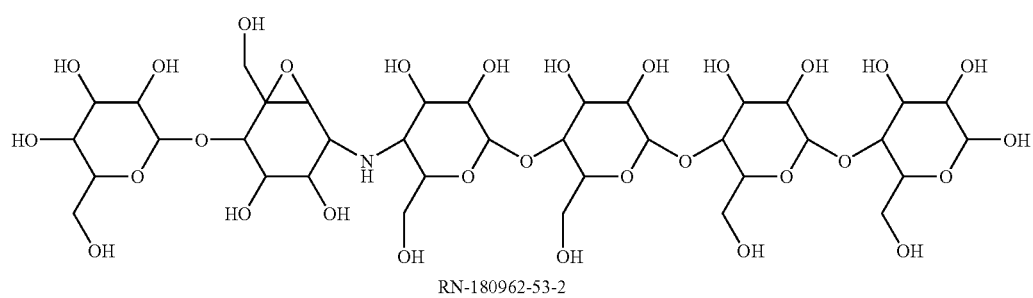

RN-180962-53-2

3 Kim, Jung Woo; Lee, Kwang Moo; Chun, Hyoung Sik; Kim, Jong Gwan; Chang, Hung Bae; Kim, Sun Ho; Min, Kyeong Bok; Moon WO-9620945-A1 p10

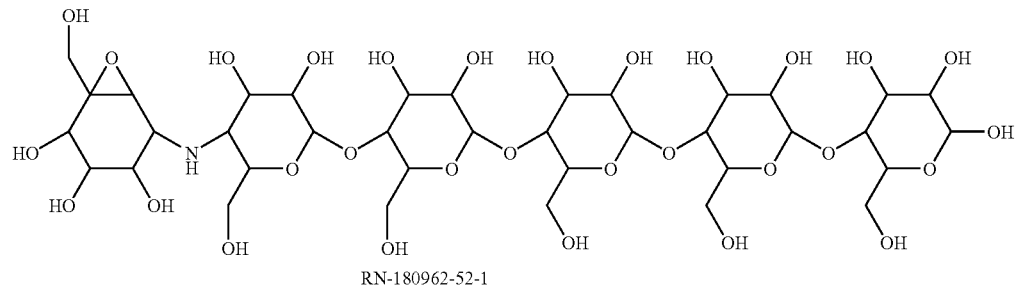
RN-180962-52-1

Kim, Jung Woo; Lee, Kwang Moo; Chun, Hyoung Sik; Kim, Jong Gwan; Chang, Hung Bae; Kim, Sun Ho; Min, Kyeong Bok; Moon WO-9620945-A1 p10

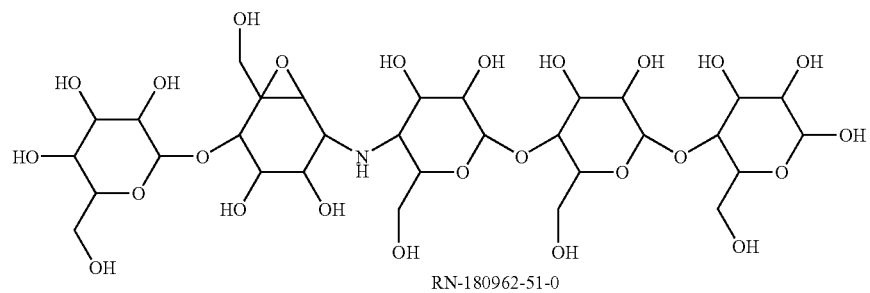
RN-180962-51-0

Kim, Jung Woo; Lee, Kwang Moo; Chun, Hyoung Sik; Kim, Jong Gwan; Chang, Hung Bae; Kim, Sun Ho; Min, Kyeong Bok; Moon WO-9620945-A1 p10

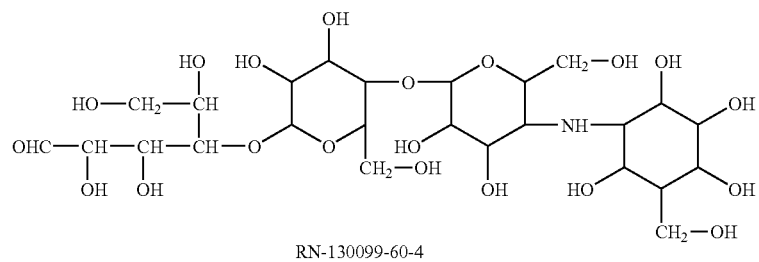
RN-130099-60-4

Hata, Yoji; Kawato, Shoji; Abe, Yasuhisa; Ono, Kazuhisa. JP-02092267-A2

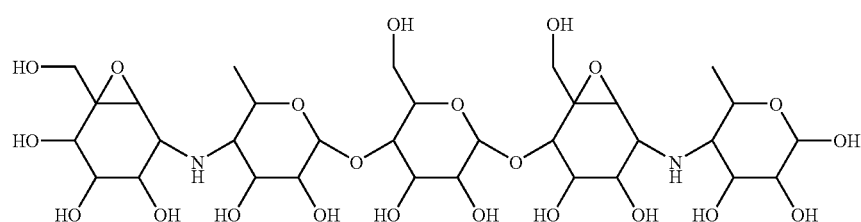
RN-121624-16-6

Vertesy, Laszlo; Betz, Joachim; Fehlhaber, Hans Wolfram; Geisen, Karl. EP-257418-A2

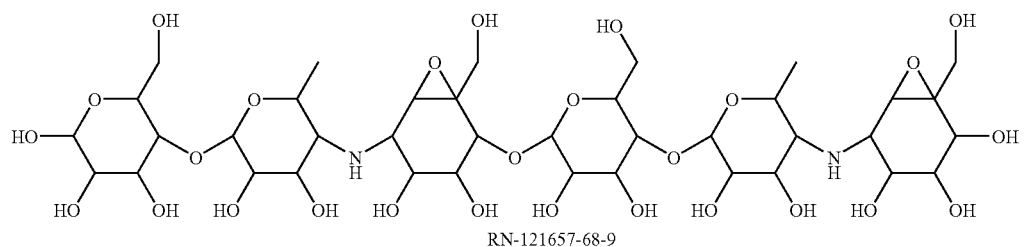

RN-121657-68-9

Vertesy, Laszlo; Betz, Joachim; Fehlhaber, Hans Wolfram; Geisen, Karl. EP-257418-A2

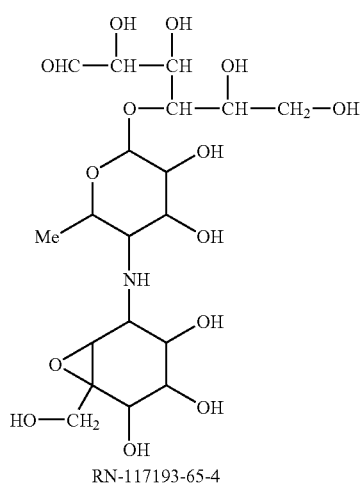

RN-117193-65-4

Ogawa, Seiichiro; Ikeda, Nobuo; Takeda, Haruki; Nakagawa, Yoshio. Carbohydrate Research (1988), 175(2), 294–301 p295

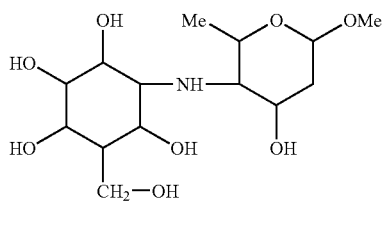

RN-128554-58-5

Shibata, Yasushi; Kosuge, Yasuhiro; Ogawa, Seiichiro. Carbohydrate Research (1990), 199(1), 37–54p38

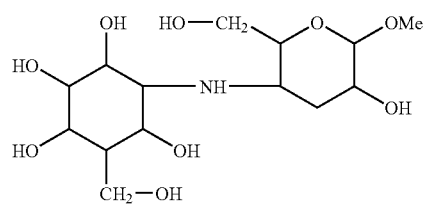

RN-128536-90-3

Shibata, Yasushi; Kosuge, Yasuhiro; Ogawa, Seiichiro. Carbohydrate Research (1990), 199(1), 37–54p38

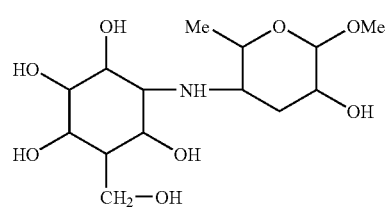

RN-128536-89-0

Shibata, Yasushi; Kosuge, Yasuhiro; Ogawa, Seiichiro. Carbohydrate Research (1990), 199(1), 37–54p38

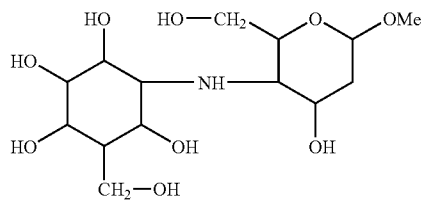

RN-128536-88-9

Shibata, Yasushi; Kosuge, Yasuhiro; Ogawa, Seiichiro. Carbohydrate Research (1990), 199(1), 37–54 p38

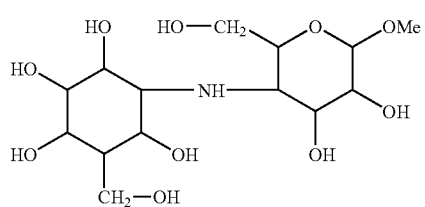

RN-128536-87-8

Shibata, Yasushi; Kosuge, Yasuhiro; Ogawa, Seiichiro. Carbohydrate Research (1990), 199(1), 37–54 p38

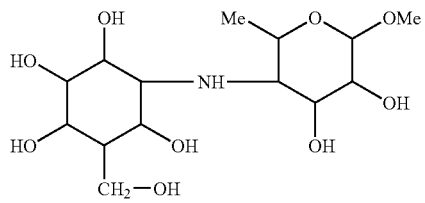
RN-128536-86-7

Fujinomori, Kenichi; Ishikawa, Akira; Nishimoto, Mayumi. JP-10101507-A2

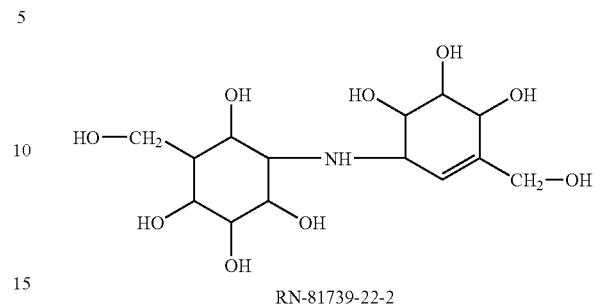
RN-81739-22-2

Ogawa, Seiichiro; Toyokuni, Tatsushi; Iwasawa, Yoshikazu; Abe, Yasuo; Suami, Tetsuo Chemistry Letters (1982), (3), 279–82

Shibata, Yasushi; Kosuge, Yasuhiro; Ogawa, Seiichiro. Carbohydrate Research (1990), 199(1), 37–54 p38

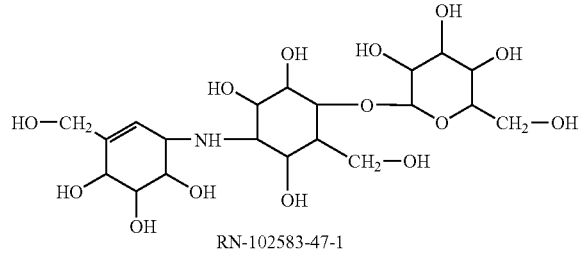
RN-102583-47-1

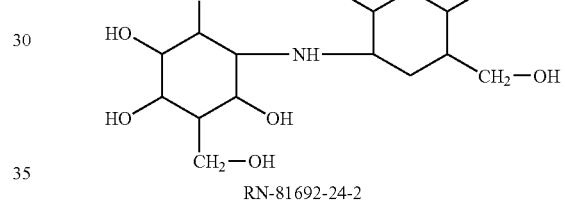
RN-81692-24-2

Ogawa, Seiichiro; Toyokuni, Tatsushi; Iwasawa, Yoshikazu; Abe, Yasuo; Suami, Tetsuo. Chemistry Letters (1982), (3), 279–82

PAGE 1-A

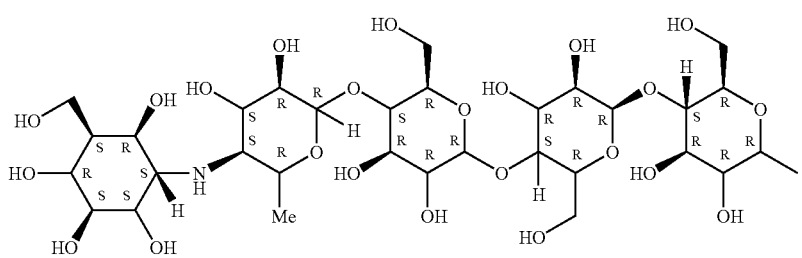

PAGE 1-B

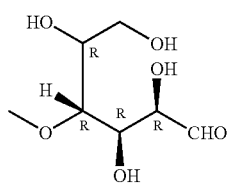
RN-80955-61-9

Itoh J; Omoto S; Shomura T; Ogino H; Iwamatsu K; Inouye S; Hidaka H. J. Antibiotics (1981 November), 34(11), p1429

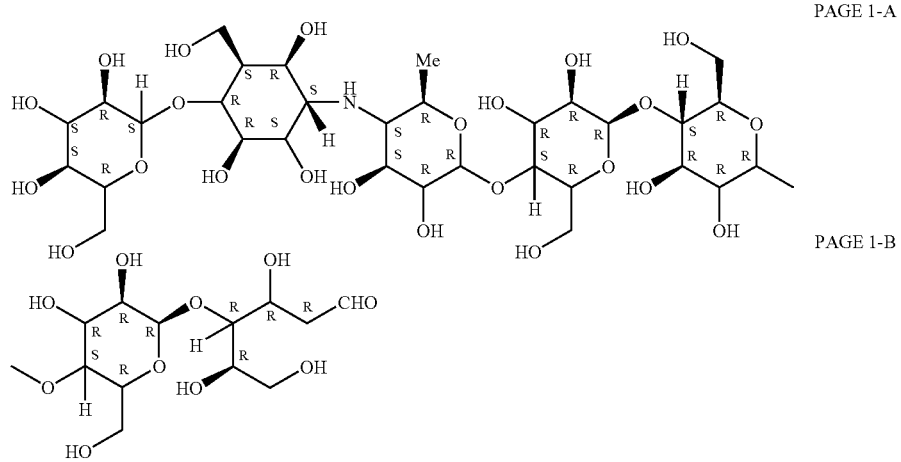

RN-80955-60-8

Itoh J; Omoto S; Shomura T; Ogino H; Iwamatsu K; Inouye S; Hidaka H J. Antibiotics (1981 November), 34(11), p1429

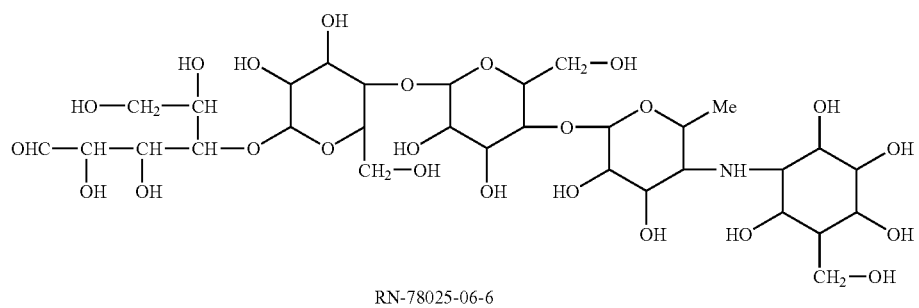

RN-78025-06-6

Itoh J; Omoto S; Shomura T; Ogino H; Iwamatsu K; Inouye S; Hidaka H. J. Antibiotics (1981 November), 34(11), p1429

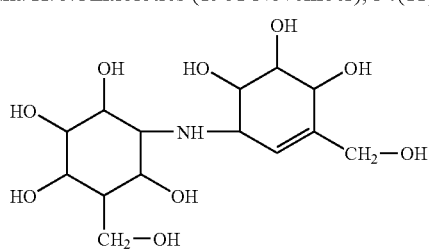

RN-39318-73-5

Horii, Satoshi; Kameda, Yukihiko; Iwasa, Takashi; Yamamoto, Hitoichi. GB-1392505

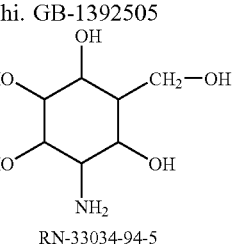

RN-33034-94-5

Kameda, Yukihiko; Asano, Naoki; Yoshikawa, Michiyo; Takeuchi, Masayoshi; Yamaguchi, Takuji; Matsui, Katsuhiko; Horii, Satoshi; Fukase, Hiroshi. Journal of Antibiotics (1984), 37(11), 1301–7p1301.

By "acarbose and the higher homologues thereof" is meant the amylostatins of the formula given below, and mentioned generically and specifically in British Patent No. GB 1,482,543; U.S. Pat. No. 4,175,123; and in *Agric. Biol. Chem.*, 46(7), 1941–1945, 1982, al of which are hereby incorporated by reference in their entirety.

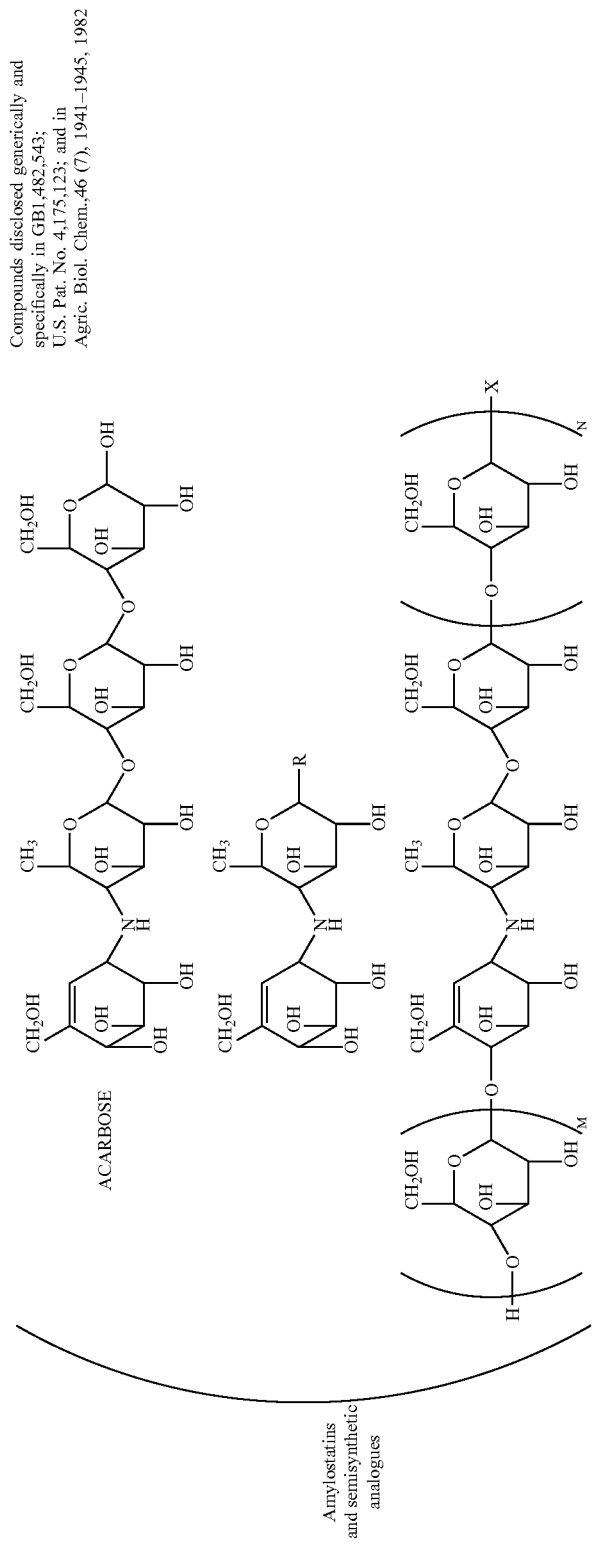

Amylostatins and semisynthetic analogues

Compounds disclosed generically and specifically in GB1,482,543; U.S. Pat. No. 4,175,123; and in Agric. Biol. Chem.,46 (7), 1941–1945, 1982 defined as "acarbose and higher homologues"*
compounds where M = 0 and N = 1, 2 or 3 are disclosed in GB 1,482,543;
compounds where M = 0 to 8, and the sum of M + N is 0 to 7;
X in both cases is OR, SH, SR, $NH_2$, NHR, or $NRR^1$;
where R is alkyl, alkenyl, cycloalkyl, aralkyl, aryl or heterocyclyl and is defined in the quoted patents.

In addition to the amylase and/or α-glucosidase inhibitor compounds mentioned above, certain derivatives of said compounds can be made following the types of chemical transformation disclosed in the tables and references below, depending on the suitability of the substrate, and which transformations are expected to result in further amylase- and/or glucosidase-inhibiting substances.

Preferably the substrate for such transformation is selected from the amylostatin compounds (i.e "acarbose and higher homologues" mentioned above), and trestatin compounds, V1532, the fraction 21 compound from Example 7, the Example 8 compound, and the compounds shown below (or suitably protected derivatives thereof):

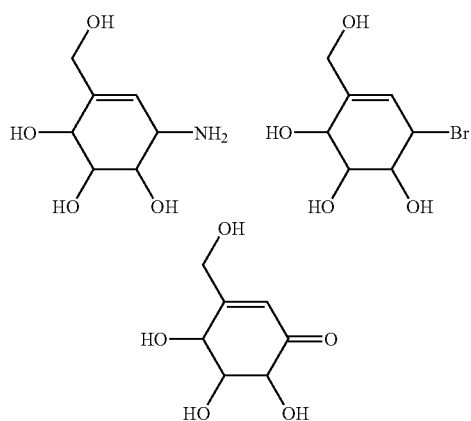

| PROCESS | LITERATURE REF. (e.g.) | EXAMPLES OF REACTING GROUPS. |
|---|---|---|
| Synthetic or biotransformation attachment of a saccharide unit or oligosaccharide via a N, S or O atom | CH-648-326-A J.Chem. Soc. Perkin Trans. 1 (1982) 1, pp 15–18<br><br>Carbohydrate Research (1978) 67, 2, pp 305–328<br>Carbohydrate Research (1997) 305, 3–4, pp 561–568 and see also later biotransformation section | Any monosaccharide or oligosaccharide such as glucose, ribose, xylose, mannose, galactose, sucrose, etc. Any monosaccharide of 2–6 sugar monomer units linked via any O or S for thio-sugars or N for aza-sugars Any cyclitol such as those described in Cyclitols and their derivatives, Hudlicky T, (1993), VCH publishers, Inc., New York Also Glucose-O-benzene-OH (attached via any oxygen) and Glucose-O-benzene-O-glucose, i.e which can be produced by methods exemplified in Agric. Biol. Chem. 53,1433, (1989) Phytochemistry, 40, 1149, (1995) U.S. Pat. No. 42346684 |
| Alkylation of any N or O with epoxide | EP-49981 | Epoxides described in EP-49981. |
| Alkylation of any N or O with alkyl-leaving group, i.e iodide, bromide, mesylate, tosylate etc. | | X–CF$_3$, X–CH$_2$–OPh, X–CH$_2$–Ph, X–CH$_2$–C(O)–NHC$_3$H$_7$, X–CH$_2$–CH$_2$–NMe$_2$<br><br>X–CH$_2$–NHCOPh, X–CH$_2$–NHSO$_2$Me, X–CH$_2$–CH$_2$–OMe, X–CH$_2$–O–C(O)–OMe<br><br>X–(tetrahydropyran), X–pyrimidine–O–glucose<br><br>where X = leaving group |
| Substitution of C-leaving group with alcohol or amine | CH-648-326-A | X–CF$_3$, X–CH$_2$–OPh, X–CH$_2$–Ph, X–CH$_2$–C(O)–NHC$_3$H$_7$, X–CH$_2$–CH$_2$–NMe$_2$ |

| PROCESS | LITERATURE REF. (e.g.) | EXAMPLES OF REACTING GROUPS. |
|---|---|---|
| Reductive alkylation of N | EP-49981 | (structures shown, where X = NH₂ or OH) + Any nitrogen containing saccharide derivative |
| Reductive amination of carbonyl | EP-240175-A | (structures shown) |

| PROCESS | LITERATURE REF. (e.g.) | EXAMPLES OF REACTING GROUPS. |
|---|---|---|
| Addition to carbonyl with organometallic species | Tetrahedron, Vol 51, No.33, 9063–9078, (1995), Bull. Soc. Chim. Fr., 134, 777–784, (1997) | + Any nitrogen containing saccharide derivative |

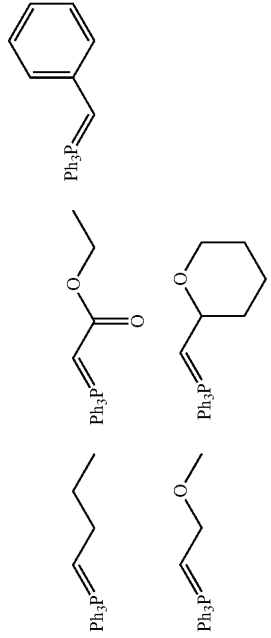

All the substances mentioned herein can be labelled e.g. with isotopes of certain atoms, as is well known in the art. Such isotopically-labelled substances are available by well-known methods in the art.

Preferred inhibitors include acarbose and higher homologues thereof, Trestatin A, Trestatin C, the compound of Fraction 21 of Example 7 below, Example 8 below, as well as the fermentation broth products mentioned below.

A preferred group of inhibitors are substantially pure single compound, or partially-purified fermentation or biotransformation product, inhibitors including acarbose and higher homologues thereof, Trestatin A, Trestatin C, the compound of Fraction 21 of Example 7 below, Example 8 below.

Especially preferred are acarbose and Trestatin C.

Some of the inhibitors may be made by biotransformation/fermentation, such as the methods described herein below.

Biotransformation/fermentation Products

The cultures *Streptomyces conglobatus* ATCC31005, *Streptomyces coelicolor* subsp. *flavus* ATCC19894, *Streptomyces kursannovii* ATCC 11912 and *Streptomyces lienomycini* ATCC43687 were obtained from the American Type Culture Collection (ATCC located at 10801 University Boulevard, Manassas, Va. 20110-2209, U.S.A.). The cultures *Streptomyces* sp. KC672 isolated from a marine sediment in Suruga Bay, Japan and *Streptomyces* sp. CL45763 have been deposited in accordance with the Budapest Treaty at the National Collections of Industrial and Marine Bacteria Ltd. and assigned the accession numbers NCIMB41058 and NCIMB41057 respectively. (NCIMB is located at 23 St. Machar Drive, Aberdeen, U.K. AB24 3RY.). The depositor was Pfizer Central Research, Pfizer Limited, Ramsgate Road, Sandwich, Kent, CT13 9NJ, United Kingdom. Pfizer Ltd. is a wholly-owned subsidiary of Pfizer Inc. 235 East 42nd Street, New York, N.Y., USA.

In addition, mutant strains of *Streptomyces conglobatus* ATCC31005, *Streptomyces coelicolor* subsp. *flavus* ATCC19894, *Streptomyces kursannovii* ATCC 11912, *Streptomyces lienomycini* ATCC43687, *Streptomyces* sp. KC672 and *Streptomyces* sp. CL45763 can be used. Such mutant strains can be obtained spontaneously, or by the application of known techniques, such as exposure to ionising radiation, ultraviolet light, and/or chemical mutagens such as N-methyl-N-nitrosourethane, N-methyl-N'-nitro-N-nitrosoguanadine, ethyl methyl sulphate etc. Genetically transformed and recombinant forms include mutants and genetic variants produced by genetic engineering techniques, including for example recombination, transformation, transduction, protoplast fusion etc.

Fermentation of the cultures of *Streptomyces conglobatus* ATCC31005, *Streptomyces coelicolor* subsp. *flavus* ATCC19894, *Streptomyces kursannovii* ATCC11912, *Streptomyces lienomycini* ATCC43687, *Streptomyces* sp. KC672 and *Streptomyces* sp.CL45763 can be carried out using standard procedures well known in the art for filamentous bacteria of the genus *Streptomyces*. For example growth of the organism may take place on suitable solid medium or aqueous liquid medium under aerobic conditions in the range 24 to 35° C. using suitable sources of carbon, nitrogen and trace elements such as iron, zinc, manganese for 2 to 30 days.

| Use is made of the following fermentation media. | |
|---|---|
| AP5-H Production Medium | |
| Corn starch (Hidex) | 80 g |
| Yeast extract (Oxoid) | 5 g |
| $K_2HPO_4$ | 1 g |
| $MgSO_4.7H_2O$ | 1 g |
| Glutamic acid | 1 g |
| $FeSO_4.7H_2O$ | 0.01 g |
| $ZnSO_4.2H_2O$ | 0.001 g |
| $MnSO_4.2H_2O$ | 0.001 g |
| $CaCO_3$ | 7 g |
| Tap water | 1 l |
| NaOH | To pH 7.0 |
| ½ strength MECO Medium | |
| Glucose | 5 g |
| Acid Hydrolysed Starch (Hidex ™, Japan) | 10 g |
| Casitone ™ (Difco - nitrogen source) | 2.5 g |
| Yeast extract (Oxoid ™) | 2.5 g |
| Wheat embryo (Sigma) | 2.5 g |
| Calcium carbonate | 2.0 g |
| Demineralised water | 1 l |
| NaOH | To pH 7.0 |
| Modified ANG-3 medium | |
| Soluble starch | 20 g |
| Glucose | 100 g |
| Soya Flour (Trusoy ™) | 10 g |
| $NaNO_3$ | 2 g |
| $K_2HPO_4$ | 1 g |
| $MgSO_4.7H_2O$ | 0.5 g |
| KCl | 0.5 g |
| $FeSO_4.7H_2O$ | 0.01 g |
| MOPS buffer (Sigma) | 20 g |
| Demin water | 1 l |
| NaOH | to pH 7 |

All the media described can be supplemented with other starches, partially hydrolysed starches or soluble starches and or sugars such as D-xylose, D-ribose, D-maltose, D-maltotriose, D-sedoheptulose, D-trehalose, D-glucose and or nitrogen sources such as asparagine, aspartate and glutamine.

EXAMPLE 1

Preparation of a Fermentation Broth Demonstrating Rumen Fluid α-amylase Inhibitory Activity from *Streptomyces conglobatus* ATCC31005

*Streptomyces conglobatus* ATCC31005 maintained on a ¼ strength ATCC172 agar slope was inoculated as a loopful of spores into two 300 ml Erlenmeyer flasks each containing 50 mls of ½ strength MECO medium. They were then allowed to incubate for 7 days at 28° C., 200 rpm on an Infors Multitron Shaker with 1" (2.5 cm) throw. At this point the broth was centrifuged at 3500 rpm and the supernatant removed from the mycelium. The α-amylase inhibitory activity was determined for the supernatant which is summarised in the table below.

| Supernatant dilution into assay | 1:1000 | 1:10000 | 1:100000 |
|---|---|---|---|
| % inhibition flask 1 | 91 | 89 | 65 |
| % inhibition flask 2 | 86 | 90 | 58 |

EXAMPLE 2

Preparation of a Fermentation Broth Demonstrating Rumen Fluid α-amylase Inhibitory Activity from *Streptomyces* sp. CL 45763

*Streptomyces* sp. CL45763 maintained on an agar slope of Bacto ISP-3 was inoculated as a loopful of spores into four 300 ml Erlenmeyer flasks each containing 50 mls of AP5-H medium. They were then allowed to incubate for 9 days at 28° C., 200 rpm on an Infors Multitron Shaker with 1" (2.5 cm) throw. At this point the broths were combined, centrifuged at 3500 rpm, and then the supernatant removed from the mycelium. The α-amylase inhibitory activity for the supernatant was then determined which is summarised in the table below.

| Supernatant dilution into assay | 1:1000 | 1:10000 | 1:100000 |
|---|---|---|---|
| % inhibition | 79 | 77 | 53 |

EXAMPLE 3

Preparation of a Fermentation Broth Demonstrating Rumen Fluid α-amylase Inhibitory Activity from *Streptomyces coelicolor* subsp. *flavus* ATCC19894

*Streptomyces coelicolor* subsp. *flavus* ATCC19894 maintained on a ¼ strength ATCC172 agar slope was inoculated as a loopful of spores into ten 300 ml Erlenmeyer flasks each containing 50 mls of AP5-H medium. They were then allowed to incubate for 4 days at 28° C., 200 rpm on an Infors Multitron Shaker with 1" (2.5 cm) throw. At this point the broths were centrifuged at 3500 rpm and the supernatant removed from the mycelium. The α-amylase inhibitory activity was determined for the combined supernatants which is summarised in the table below.

| Supernatant dilution into assay | 1:1000 | 1:10000 |
|---|---|---|
| % inhibition flask 1 | 66 | 35 |

EXAMPLE 4

Preparation of a Fermentation Broth Demonstrating Rumen Fluid α-amylase Inhibitory Activity from *Streptomyces kursannovii* ATCC11912

*Streptomyces kursannovii* ATCC11912 maintained on a ¼ strength ATCC172 agar slope was inoculated as a loopful of spores into two 300 ml Erlenmeyer flasks each containing 50 mls of AP5-H medium. They were then allowed to incubate for 5 days at 28° C., 200 rpm on an Infors Multitron Shaker with 1" (2.5 cm) throw. At this point the broths were centrifuged at 3500 rpm and the supernatant removed from the mycelium. The α-amylase inhibitory activity was determined for each supernatant which is summarised in the table below.

| Supernatant dilution into assay | 1:1000 | 1:10000 | 1:100000 |
|---|---|---|---|
| % inhibition Flask 1 | 85 | 73 | 27 |
| % inhibition Flask 2 | 85 | 70 | 30 |

EXAMPLE 5

Preparation of a Fermentation Broth Demonstrating Rumen Fluid α-amylase Inhibitory Activity from *Streptomyces lienomycini* ATCC43687

*Streptomyces lienomycini* ATCC43687 maintained on a ¼ strength ATCC172 agar slope was inoculated as a loopful of spores into three 300 ml Erlenmeyer flasks each containing 50 mls of modified ANG-3 medium. They were then allowed to incubate for 5 days at 28° C., 200 rpm on an Infors Multitron Shaker with 1" (2.5 cm) throw. At this point the broths were centrifuged at 3500 rpm and the supernatant removed from the mycelium. The α-amylase inhibitory activity was determined for each individual supernatant which is summarised in the table below.

| Supernatant dilution into assay | 1:1000 | 1:10000 | 1:100000 |
|---|---|---|---|
| % inhibition flask 1 | 87 | 70 | 41 |
| % inhibition flask 2 | 85 | 75 | 41 |
| % inhibition flask 3 | 85 | 76 | 47 |

EXAMPLE 6

Preparation of a Fermentation Broth Demonstrating Rumen Fluid α-amylase Inhibitory Activity from *Streptomyces* sp. KC672

*Streptomyces* sp. KC672 maintained on a ¼ strength ATCC172 agar slope was inoculated as a loopful of spores into two 300 ml Erlenmeyer flasks each containing 50 mls of AP5-H medium. They were then allowed to incubate for 7 days at 28° C., 200 rpm on an Infors Multitron Shaker with 1" (2.5 cm) throw. At this point the broths were centrifuged at 3500 rpm and the supernatant removed from the mycelium. The α-amylase inhibitory activity was determined for the supernatants which is summarised in the table below.

| Supernatant dilution into assay | 1:1000 | 1:10000 |
|---|---|---|
| % inhibition flask 1 | 54 | 21 |
| % inhibition flask 1 | 49 | 22 |

EXAMPLE 7

Isolation of a Rumen Fluid α-amylase Inhibitor from *Streptomyces conglobatus* ATCC31005

A loopful of spores of *Streptomyces conglobatus* ATCC31005 maintained on ¼ strength ATCC172 agar was inoculated into two 300 ml Erlenmeyer flasks, each containing 50 ml of AP5-H medium. After 24 hours incubation at 28° C., 200 rpm on an Infors Multitron Shaker with 1"

(2.5 cm) throw, these flasks were used to inoculate two 5 liter minijars (Electrolab™, Gloucester, U.K) each containing 3.5 liters each of AP5-H medium. These broths were incubated at 28° C. with an aeration of 3 l/min and stirring at 300 rpm for 6 days. At harvest the broths were centrifuged at 2500 rpm and the supernatants decanted. They were each stirred twice for 45 minutes with 86 g of charcoal and then filtered through a 500 g bed of Arbocel™. The pH at this stage was pH7. Each carbon cake was extracted twice with 860 mls of aqueous acetone (1:1) maintaining the pH between 2 and 3 by the addition of concentrated hydrochloric acid. The four aqueous acetone extracts were partially evaporated, combined and lyophilised to give 40 g of a brown solid. This solid was then dissolved in 500 mls of deionised water and applied to a column of 750 mls Amberlite IR120 ($H^+$ form) at a flow rate of 2 ml/min. The column was then washed with 1 l. of water and then eluted with 5N ammonia solution collecting 50 ml fractions. Fractions 13 to 28 were lyophilised to give 1.4 g of a dark brown powder. This was then dissolved in 15 mls of water, filtered and the resulting filtrate diluted with 5 mls of acetonitrile. This was injected in 2 ml volumes on to a Cosmosil $NH_2$-MS column (20×250 mm) and eluted at 20 mls/min with acetonitrile water (60:40). Fractions were collected every 30 seconds and analysed by LC-MS using a Finnegan AQA™ instrument. Fractions containing $M+H^+970$ were combined and dried down to give a gum solid, 70 mgs. The solid was then dissolved in two mls of water, filtered and injected in two halves on to an Waters Aqua™ 5 micron 125A column (21×150 mm), using a Waters Delta Prep™ 4000 system with diode array detection. Fractions were collected and two, both fraction 21, were combined containing the $M+H^+$ 970 peak resulting in a white solid, 6.5 mg.

Accurate mass data was collected on a Bruker Apex II FT-ICR-MS 4.7 T instrument where the sample, dissolved in methanol/water/acetic acid (50:50:1) at approx 0.5 mgs/ml, was introduced into an Analytica electrospray source by direct infusion at 4 μl/min.

m/z (ESI, FTMS) $[M+H]^+=970.3601$, $C_{37}H_{64}NO_{28}$ requires 970.3609 m/z (ESI, FTMS) $[M+Na]^+=992.3452$, $C_{37}H_{63}NO_{28}Na$ requires 992.3429

The NMR (proton, carbon-13, TOCSY, HSQC and HMBC) and mass spectra of this fraction 21 compound, also known as "6942/99/1" are consistent with the structure shown below.

The compound shown above has been disclosed in GB patent 1 482 543 and (Ag. Biol. Chem. 46(7) (1982) 1941).

Table: $^1H$ and $^{13}C$ NMR chemical shifts of 6942/99/1 (δ in ppm relative to internal dioxane)

| Position | $δ_H$ | multiplicity | J (Hz) | $δ_C$ |
|---|---|---|---|---|
| A1-$CH_2OH$ | 4.09/4.20 | 2 × d | 14.2 | 64.5 |
| A1 | — | — | — | 141.9 |
| A2 | 5.87 | d, br | 5.3 | 126.6 |
| A3 | 3.51 | t, br | ~5 | 58.9 |
| A4 | 3.63 | m | — | 73.9 |
| A5 | 3.73 | m | — | 75.9 |
| A6 | 4.01 | d, br | 6.9 | 74.2 |
| B1 | 5.28 | m | 3.6 | 102.8 |
| B2 | 3.57 | m | — | 75.6 |
| B3 | 3.58 | m | — | |
| B4 | 2.45 | t | 9.7 | 67.8 |
| B5 | 3.72 | m | — | 72.6 |
| B6-Me | 1.31 | d | 6.4 | 20.2 |
| Rings C-E: 1 | ~5.37 | d | 4.0 | ~102.4 |
| 2 | ~3.60 | dd | 9.5,4.0 | ~74.4 |
| 3 | ~3.93 | t | ~9.5 | ~76.2 |
| 4 | ~3.62 | t | ~9.5 | ~79.9 |
| 5 | ~3.81 | m | — | ~74.2 |
| 6-$CH_2$ | ~3.79/3.83 | m | — | ~63.4 |
| α-F1 | 5.20 | d | 3.9 | 94.9 |
| α-F2 | 3.54 | dd | ~9.5, 3.9 | |
| α-F3 | 3.94 | t | ~9.5 | 76.2 |
| α-F4 | 3.62 | t | ~9.5 | ~79.9 |
| α-F5 | 3.91 | m | — | 72.8 |
| α-F6-$CH_2$ | ~3.8 | m | — | ~63.4 |
| β-F1 | 4.63 | d | 7.9 | 98.8 |
| β-F2 | 3.25 | dd | 7.9, 9.5 | 76.9 |
| β-F3 | 3.74 | t | 9.5 | 79.1 |
| β-F4 | 3.63 | dd | 9.5, 8.3 | ~79.9 |
| β-F5 | 3.56 | m | — | 77.5 |
| β-F6-$CH_2$ | ~3.87 | m | — | ~63.4 |

The "Fraction 21 compound" was found to have an inhibiting effect in the amylase screen mentioned herein.

EXAMPLE 8

Isolation of a Rumen Fluid α-amylase Inhibitor from *Streptomyces conglobatus* ATCC-31005

The AP5-H Production Medium mentioned above was used as fermentation medium.

*Streptomyces conglobatus* ATCC31005 maintained on a ¼ strength ATCC172 agar slope was inoculated as a loopful of spores into two 300 ml Erlenmeyer flasks each containing 50 mls of AP5-H medium. They were then allowed to incubate for 24 hours at 28° C., 200 rpm on an Infors Multitron Shaker with 1" throw. At this point the inoculum

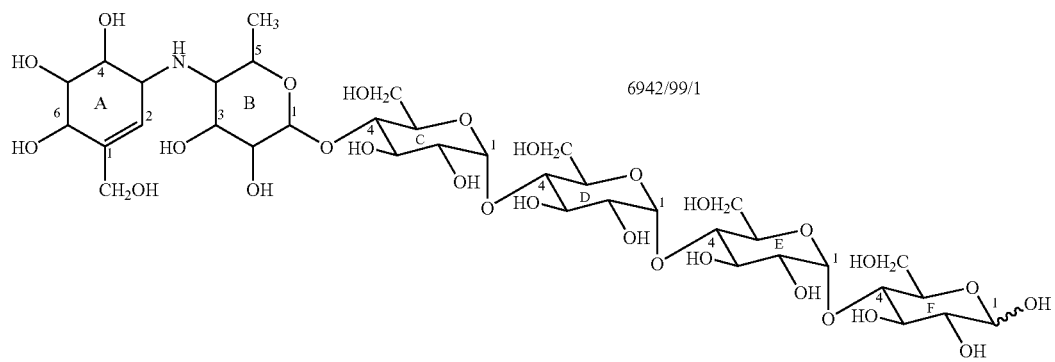

6942/99/1 was transferred into a 3 liter Fernbach flask containing 1 liter of AP5-H medium and incubated for a further 24 hours under the same conditions as described for the Erlenmeyer flasks. This inoculum was then transferred to 20 liters of AP-5H medium which had previously been sterilised in a 30 liter New Brunswick Micros™ stainless steel fermenter. The broth was then agitated at 300 rpm at 28° C. with 20 l/min air for 112 hours and then harvested.

The harvested broth was centrifuged using a Carr Powerfuge™ at 20 000G. To the supernatant, at a natural pH of 7.8, was added 500 g of activated decolourising charcoal (Aldrich 16155-1) and the mixture stirred for 16 hours. Following filtration through a filter aid, such as Arbocel™, the supernatant was treated with a further 500 g charcoal, for 1 hour in the same manner. The combined charcoal cakes were washed with aqueous methanol (10 L 1:1) and then extracted twice with aqueous acetone (10 L 1:1) by stirring for 1 hour followed by filtration through filter aid. Following partial rotary evaporation and freeze drying, 98.7 g of biologically active material were obtained.

This material was dissolved in 1800 ml demineralised water and loaded onto a column of 3.5 L Amberlite IR 120(H)™ at a rate of 5 ml/minute. Following a water wash (2 L) the product was eluted with 1 L aliquots of 5N ammonia solution. Following freeze drying, the most potent fractions (5 to 8) were combined to give 10.8 g of brown solid.

1.1 g of this material was purified by chromatography, in five equal injections, using a Waters Delta Prep 4000™ chromatography system, a 250×21.2 mm CromasilNH$_2$ (ex Phenomenex) and a gradient from 67% acetonitrile 33% water to 50/50 at 20 minutes at a flow rate of 24 ml/minute. 12 ml fractions were collected.

The fractions containing the peak of interest (31 to 35 from each run) were combined to give 138 mg white solid. This material was chromatographed again, this time using a 150×21.2 mm Aqua column (ex Phenomenex) and a gradient from 100% water to 90% water 10% acetonitrile over 15 minutes at a flow rate of 21.2 ml/minute. Fractions were collected at half minute intervals. A total of 43 mg of desired product, I was obtained from fractions 22 and 23.

The observed data are consistent with the following structure, referred to herein as the "Example 8 compound":

| Position | H | Multiplicity | J (Hz) | C |
|---|---|---|---|---|
| A1-CH2OH | 4.09/4.21 | 2 × d | 14.2 | 64.2 |
| A1 | — | — | — | 141.7 |
| A2 | 5.88 | d, br | 5.3 | 126.2 |
| A3 | 3.52 | t, br | ~5 | 58.8 |
| A4 | 3.64 | m | — | ~73.9 |
| A5 | 3.74 | m | — | ~75.9 |
| A6 | 4.01 | d, br | 7.2 | ~73.7 |
| B1 | 5.33 | m | 3.6 | ~102.2 |
| B2 | 3.57 | m | — | 75.5 |
| B3 | 3.58 | m | — | ? |
| B4 | 2.45 | t | 9.7 | 67.7 |
| B5 | 3.72 | m | — | 72.2 |
| B5-Me | 1.31 | d | 6.4 | 20.0 |
| C1 | 5.36 | d | 3.8 | 100.1 |
| C2 | 3.59 | dd | — | 73.8 |
| C3 | 3.89 | t | — | 76.2 |
| C4 | 3.61 | t | — | ~79.3 |
| C5 | 3.88 | m | — | ~74.2 |
| C6-CH2 | 3.82 | m | — | ~63.1 |
| D1-CH2OH | 4.09/4.21 | 2 × d | 14.1 | 64.7 |
| D1 | — | — | — | 139.1 |
| D2 | 5.95 | d, br | 4.1 | 128.9 |
| D3 | 3.52 | t, br | ~5 | 57.7 |
| D4 | 3.82 | m | — | 71.9 |
| D5 | 4.15 | dd | 8.2, 5.3 | 73.3 |
| D6 | 4.21 | d, br | 6.9 | 78.4 |
| E1 | 5.33 | m | 3.6 | ~102.2 |
| E2 | 3.57 | m | — | 75.6 |
| E3 | 3.58 | m | — | ? |
| E4 | 2.45 | t | 9.7 | 66.7 |
| E5 | 3.72 | m | — | 72.2 |
| E5-Me | 1.31 | d | 6.4 | 20.0 |
| Rings F-H:1 | ~5.40 | d | 3.8 | ~102.2 |
| 2 | ~3.59 | dd | 9.5/d.0 | ~75.2 |
| 3 | ~3.93 | t | ~9.5 | ~76.1 |
| 4 | ~3.65 | m | ~9.5 | ~79.1 |
| 5 | ~3.82 | m | — | ~73.8 |
| 6-CH2 | ~3.79/3.83 | m | — | ~63.1 |
| α-I1 | 5.21 | d | 3.8 | 94.9 |
| α-I2 | 3.54 | dd | ~9.5, 3.9 | |
| α-I3 | 3.94 | t | ~9.5 | 76.2 |
| α-I4 | 3.62 | t | ~9.5 | ~79.9 |
| α-I5 | 3.91 | m | — | 72.8 |
| α-I6-CH2 | ~3.8 | m | — | ~63.4 |
| β-I1 | 4.63 | d | 7.9 | 98.7 |
| β-I2 | 3.25 | dd | 7.9, 9.5 | 76.9 |
| β-I3 | 3.74 | t | 9.5 | 79.1 |
| β-I4 | 3.63 | dd | 9.5, 8.3 | ~79.9 |

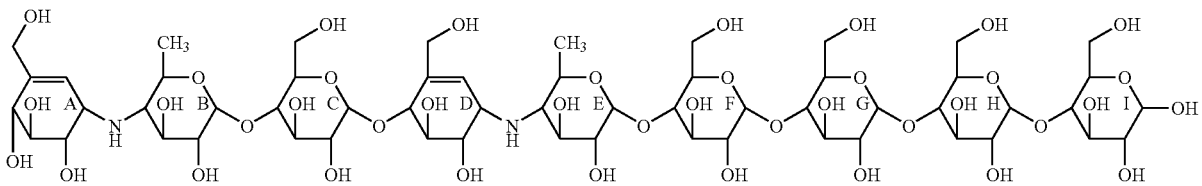

M/z (ESI, FT-MS) [M+H]$^+$=1435.546 corresponding to a molecular formula of $C_{56}H_{95}N_2O_{40}$ (+/−3.028 ppm).

M/z (ESI, FT-MS) [M+Na]$^+$=1457.528 corresponding to a molecular formula of $C_{56}H_{94}N_2O_{40}Na$ (+/−1.914 ppm).

All NMR data given below were recorded on a Varian Innova 600 MHz machine at 10° C. in D$_2$O using a 3 mm probe.

-continued

| Position | H | Multiplicity | J (Hz) | C |
|---|---|---|---|---|
| β-I5 | 3.56 | m | — | 77.5 |
| β-I6-CH2 | ~3.87 | m | — | ~63.4 |

NB where a "?" appears in the table above, there was severe signal overlap meaning that an unambiguous assignment could not be made Modifications to Acarbose and Other Related α-amylase and/or α-glucosidase Inhibitors Biotransformations Microbial Biotransformation Microbial whole organisms capable of glycosylation of acarbose or other related α-amylase and/or α-glucosidase inhibitors could be used to give increased α-amylase and/or α-glucosidase inhibitory activity, which include *Bacillus subtilis* ATCC55060[1], *Saccharopolyspora erythrae* ATCC11635[2] and a blocked mutant of *S.avermitilis* ATCC53567[3]. Other organisms which can glucosidate include *Cunninghamella* sp. NRRL5695[14] and *Beauvaria bassiana* DSM 875 and DSM 1344[15]. Moreover the microbial directed biosynthesis of acarbose by an *Actinoplanes* sp. CBS 793.96[4] fed with rutin could also be used with other related α-amylase and/or α-glucosidase inhibitor producing organisms. These may give analogues of acarbose or related acarbose like homologues which could also demonstrate increased α-amylase and/or α-glucosidase inhibitory activity.

Moreover microorganisms capable of O-acylation[16], oxidation (incl. epoxidation[17] and ketone[18] formation), hydroxymethylation[19] O-methylation[20], etc. can also be used to make new analogues of acarbose and related analogues which could also demonstrate increased α-amylase and/or α-glucosidase inhibitory activity.

Crude, Partially Purified and Purified Enzyme Biotransformations

Enzymatic methods of glycosylation can be used to synthesise or modify oligosaccharides. Specific protection and deprotection of hydroxyl groups is not required and the enzymes only transfer to one or two hydroxyl groups. This often leads to fewer reaction steps and simpler purification procedures.

Transglycosylation of *Bacillus stearothermophilus* maltogenic amylase (BSMA) with acarbose and various acceptors have been used, where the enzyme was an *Escherichia coli* transformant carrying the BSMA gene.[5] Here it was observed that the BSMA cleaved the first glycosidic bond of acarbose to give the pseudotrisaccharide (PTS) and then added on a glucose unit at the α (1→6) position to give isoacarbose, where acarbose itself has an α (1→4) linkage at the terminal glucose. The addition of a number of different carbohydrates to the digest gave transfer products in which the PTS was primarily attached a (1→6) to D-glucose, D-mannose, D-galactose and methyl α-D-glucopyranoside. With D-fructopyranose and D-xylopyranose, PTS was linked at α (1→45) and α (1→4) respectively. α-α Trehalose and maltitol both gave two major products with PTS linked α (1→6) and α (1→4) to the glucopyranose residue. PTS was primarily transferred to C-6 of the nonreducing residue of maltose, cellobiose, lactose and gentiobiose. Sucrose gave PTS linked α (1→4) to the glucose residue. Raffinose gave two major products with PTS linked α (1→6) and α (1→4) to the D-galactopyranose residue. Maltotriose gave two major products with PTS linked α (1→6) and α (1→4) to the nonreducing end glucopyranose residue. Xylitol gave PTS linked α (1→5) as the major product and D-glucitol gave PTS linked α (1→6) as the only product. All these examples may show improved α amylase inhibitory activity.

Other groups of enzymes can be used to produce glycosidated analogues of acarbose or other amylase and/or α-glucosidase inhibitors that have accessible sugar or hydroxyl groups. Enzymatic preparations that may be used include α- and β-galactosidase, α- and β-mannosidase, β-N-acetylglucosaminidase, β-N-acetylgalactoaminidase, and α-L fucosidase.[6] Glycosidation can take place at either end of the valienamine or cyclitol unit of acarbose and experience shows that the glycosyl transfer is preferred to take place at the non reducing terminal monosaccharide unit of substrates.[7] Studies using endo glycosidases may lead to branched structures. The enzyme preparations described can be microbially derived e.g *Aspergillus niger, A. terreus, A. oryzae, Bacillus circulans, B. stearothermophilus, Coccobacillus,* or insect juice e.g snail, or plant derived e.g apples, mushrooms, alfalfa seeds, defatted almond meal etc.[6]

Glycosyltransferases can also be used to glycosylate acarbose and related analogues demonstrating α-amylase inhibitory activity but are much rarer enzymes.[8] Many of these glycosyltransferases have been cloned. They are often referred to as being rather stringent to the distal one to two saccharide moieties and are also very specific to the glycosyl donor. They can be persuaded to work with both unnatural donors and/or acceptors maintaining their advantages of strict regio and stereoselectivity and high yields. Only a few glycosyltransferases are readily available and most experiments have been carried out with galactosyltransferase Gal T.[9]

A special group of glycosyl transferases are cyclodextrin glucanotransferases (CGTase). These enzymes are produced by microorganisms and many are commercially available. They catalyse cyclodextrination of starch but also transfer one or more α-glucosyl units to various acceptors. They can be used for extending glycosides or for α-glucosylation of many compounds. CGTase from *B. stearothermophilus* was used for the transglucosylation of rutin where the glucosyl unit was extended by one or more glucose units.[10] A similar approach could be used for acarbose and related α-amylase and/or α-glucosidase inhibitors containing glucose units.

Another approach is to use glycogen phosphorylase which is the well known enzyme responsible for the formation or degradation of α (1→4) glucans. Phosphorylase requires an activated substrate such as the glucosyl phosphate ester. With this substrate a glucan chain, the primer unit, can be elongated by glucose units with the release of phosphate.[11]

Modification of acarbose and related α amylase and/or α-glucosidase inhibitors containing sugar units can also be made using selective hydrolyses with α amylase itself which can either cleave sugar units or transglycosylate[12,13]

For other modifications of the hydroxyl groups of sugar units acylases, esterases, lipases, hydrolases and dehydratases can also be used.

REFERENCES FOR THIS SECTION

1. Petuch B. R et al. Microbial transformation of immunosuppressive compounds 111. Glucosylation of immunomycin and FK506 by *Bacillus subtilis* ATCC55060. J. Ind. Microbiol. 13, 131–135, (1994)
2. Arison, B. H et al. Microbial glycosidation of avermectins. Eur. Pat. Appl. (1992) EP 520557 A1.
3. Pacey M. S. et al. Preparation of 13-epi-selamectin by biotransformation using a blocked mutant of *Streptomyces avermitilis*. J. Antibiotics, 53 (3), 301–305, (2000)
4. Cruegar, A et al. Novel acarviosin glycoside: synthesis of a new saccharase inhibitor via biotransformation. Ger. Offen. (1999) DE 19821038 A1
5. Park, H. P et al. Transglycosylation reactions of *Bacillus stearothermophilus* maltogenic amylase with acarbose and various acceptors. Carbohydrate Res. 313, (1998), 235–246
6. M. Scigelova et al. Glycosidases—a great synthetic tool. J. of Molecular Catalysis B: Enzymatic 6, (1999), 483–494.

7. Crout D H G, et al. Glycosidases and glycosyltransferases in glycoside and oligosaccharide synthesis. Curr. Opin. Chem. Biol 2(1),(1998), 98–111,
8. Kren, V., et al. Glycosylation employing bio-systems: from enzymes to whole cells. Chem. Soc. Rev. 26, (1997), 463
9. C. H. Wong. et al Enzymes in Synthetic Organic Chemistry. Tetrahedron Org. Chem. Ser. Eds. Baldwin J. E & Magnus P. D., Pergamon (1994), Vol 12.
10. Suzuki et al. Agric. Biol. chem. Enzymatic formation of 4-α-D-glucopyranosyl-rutin 55, (1991), 181
11. Evers B et al. Further syntheses employing phosphorylase. Bioorganic & Medicinal Chemistry 5(5), (1997), 857–863
12. Takada, M et al. Chemo-enzymic synthesis of galactosylmaltooligosaccharidonolactone as a substrate analogue inhibitor for mammalian α-amylase. Japan. J. Biochem. (Tokyo) 123(3), (1998), 508–515
13. Kim, T. K et al. Synthesis of glucosyl-sugar alcohols using glycosyltransferases and structural identification of glucosyl-maltitol. J. Microbiol. Biotechnol. 7(5), (1997), 310–317.
14. Chatterjj, P et al. Glucosidation of betulinic acid by *Cunninghamella* sp. J. Nat. Prod. 62(5), (1999), 761–763.
15. Kittleman, M et al. Microbial hydroxylation and simultaneous formation of the 4"-O-methylglucoside of the tyrosine-kinase inhibitor CGP 62706. Chimia 53(12), (1999), 594–596.
16. Oda S et al. Double coupling of acetyl coenzyme A production and microbial esterfication with alcohol acetyltransferase in an interface bioreactor. J. Ferment. Bioeng. 83, (1997), 423–428
17. Garcia-Granados et al. Biotransformation of ent-6α-acetoxy- and ent-6-ketomanoyl oxides with *Rhizopus nigricans* ATCC10404 and *Curvularia lunata* ATCC12017. Phytochemistry 45, (1997),283–291.
18. Fantin, G et al. Regioselective microbial oxidation of bile acids. Tetrahedron, 54, (1998), 1937–1942
19. Azerad, R. Patent application WO 99/47963 dated 23, Sep. 1999. Novel method for the production of fexofenadine using *Absidia corymbifera* LCP 63–1800 or *Streptomyces platensis* NRRL 2364.
20. Sariaslani, F et al. Novel biotransformations of 7-ethoxycoumarin by *Streptomyces griseus*. NRRL8090. Appl. Environ. Microbiol.46(2), (1983), 468–474.

Certain of the substances mentioned herein can exist in one or more geometric and/or stereoisomeric forms. The present disclosure includes all such individual isomers and salts and prodrugs thereof. Certain compounds mentioned herein could exist in more than one tautomeric form. Similarly certain compounds mentioned herein may have zwitterionic forms. It is to be understood that the disclosure embraces all such tautomers, zwitterions and their derivatives.

The disclosure includes veterinarily acceptable salts of the compounds mentioned herein, including the acid addition and the base salts thereof where appropriate. Suitable acid addition salts are formed from acids which form non-toxic salts and examples are the hydrochloride, hydrobromide, hydroiodide, sulphate, hydrogen sulphate, nitrate, phosphate, hydrogen phosphate, acetate, maleate, fumarate, lactate, tartrate, citrate, gluconate, succinate, benzoate, methanesulphonate, benzenesulphonate and p-toluenesulphonate salts. Suitable base salts are formed from bases which form non-toxic salts and examples are the aluminium, calcium, lithium, magnesium, potassium, sodium, zinc and diethanolamine salts. For a review on suitable salts see Berge et al, J. Pharm. Sci., 66, 1–19 (1977).

It will be appreciated by those skilled in the art that certain protected derivatives of compounds mentioned herein, which may be made prior to a final deprotection stage, may not possess the desired biological activity as such, but may, in certain instances, be transformed after administration into the body, for example by metabolism, to form compounds mentioned herein which are biologically active. Such derivatives are included in the term "prodrug". It will further be appreciated by those skilled in the art that certain moieties known to those skilled in the art as "pro-moieties", for example as described in "Design of Prodrugs" by H Bundgaard (Elsevier) 1985, may be placed on appropriate functionalities when such functionalities are present in compounds mentioned herein, also to form a "prodrug". Further, certain compounds mentioned herein may act as prodrugs of other compounds mentioned herein. All protected derivatives, and prodrugs, of the compounds mentioned herein are included within the scope of the disclosure.

The skilled person will appreciate that certain substances mentioned herein can be made by methods other than those hereinafter described, by adaptation of the methods herein described and/or adaptation of methods known in the art, for example the art described herein, or using standard textbooks such as "Comprehensive Organic Transformation—A Guide to Functional Group Transformations", R C Larock, VCH (1989 or later editions), "Advanced Organic Chemistry—Reactions, Mechanisms and Structure", J. March, Wiley-Interscience (3rd or later editions), "Organic Synthesis—The Disconnection Approach", S Warren (Wiley), (1982 or later editions), "Designing Organic Syntheses", S Warren (Wiley), (1983 or later editions), "Guidebook To Organic Synthesis" R K Mackie and D M Smith (Longman) (1982 or later editions), "Methoden der Organischen Chemie", Houben Weyl, Georg Thieme Verlag, Stuttgart, "The Chemistry of the Hydroxyl Group" Parts 1 & 2, Saul Patal, (1971), Interscience Publishers, "The Chemistry of the Amino Group", Saul Patal, (1968), Interscience Publishers, "Trends in Synthetic Carbohydrate Chemistry", ACS Symposium Series 386, (1989), American Chemical Society, Washington, D.C., "Advances in Carbohydrate Chemistry and Biochemistry", Volumes 1–39, Academic Press, New York "Carbohydrate Chemistry", Volumes 1–11, The Chemical Society, London, "Methods in Carbohydrate Chemistry", Volumes 1–8, Academic Press, New York, "Carbohydrates Synthetic Methods and Applications in Medicinal Chemistry", Ogura, H. et al, (1982), Kodansha, Tokyo. etc.

and the references therein as a guide.

It is to be understood that the synthetic transformation methods mentioned herein are exemplary only and they may be carried out in various different sequences in order that the desired compounds can be efficiently assembled. The skilled chemist will exercise his judgment and skill as to the most efficient sequence of reactions for synthesis of a given target compound. For example, substituents may be added to and/or chemical transformations performed upon, different intermediates to those mentioned hereinafter in conjunction with a particular reaction. This will depend inter alia on factor such as the nature of other functional groups presents in a particular substrate, the availability of key intermediates and the protecting group strategy (if any) to be adopted.

Clearly, the type chemistry involved will influence the choice of reagent that is used in the said synthetic steps, the need, and type, of protecting groups that are employed, and the sequence for accomplishing the synthesis. The procedures may be adapted as appropriate to the reactants, reagents and other reaction parameters in a manner that will be evident to the skilled person by reference to standard textbooks and to the examples provided hereinafter.

It will be apparent to those skilled in the art that sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc (1999), and references therein. Functional groups which may desirable to protect include oxo, hydroxy, amino and carboxylic acid. Suitable protecting groups for oxo include acetals, ketals (e.g. ethylene ketals) and dithianes. Suitable protecting groups for hydroxy include trialkylsilyl and diarylalkylsilyl groups (e.g. tert-butyldimethylsilyl, tert-butyldiphenylsilyl or trimethylsilyl) and tetrahydropyranyl. Suitable protecting groups for amino include tert-butyloxycarbonyl, 9-fluorenylmethoxycarbonyl or benzyloxycarbonyl. Suitable protecting groups for carboxylic acid include $C_{1-6}$ alkyl or benzyl esters.

The amylase and/or α-glucosidase inhibitors may be administered either alone or in combination with one or more agents used in the treatment (including prophylaxis) of disease or in the reduction or suppression of symptoms as appropriate for the treatment of acidosis and related conditions. Examples of such agents (which are provided by way of illustration and should not be construed as limiting) include buffers, antibiotics including ionophores, probiotics, organic acids and bacteriocins, antiparasitics, eg fipronil, lufenuron, imidacloprid, avermectins (eg abamectin, ivermectin, doramectin), milbemycins, organophosphates, pyrethroids; antihistamines, eg chlorpheniramine, trimeprazine, diphenhydramine, doxylamine; antifungals, eg fluconazole, ketoconazole, itraconazole, griseofulvin, amphotericin B; antibacterials, eg enroflaxacin, marbofloxacin, ampicillin, amoxycillin; anti-inflammatories eg prednisolone, betamethasone, dexamethasone, carprofen, ketoprofen; dietary supplements, eg gamma-linoleic acid; and emollients.

The amylase and/or α-glucosidase inhibitors can be administered alone but will generally be administered in admixture with a suitable excipient, diluent or carrier selected with regard to the intended route of administration and standard pharmaceutical/veterinary/farming practice.

Advantageously for treatment of livestock animals such as sheep and cattle, the active agent can be administered orally using suitable standard methods such as mixed with the animal's feedstuff, in the drinking fluid or via a bolus delivered directly to the rumen. For in-feed administration a concentrated feed additive or premix may be provided for mixing with the normal animal feed. Additional physical and chemical stabilising agents may also be included to maintain or enhance the stability of the active agents in the said formulation.

The methods by which the active agent may be administered include oral administration by capsule, bolus, tablet or drench, or, alternatively, they can be administered by injection or as an implant into the rumen. Such formulations may be prepared in a conventional manner in accordance with standard veterinary practice.

For example, the active agent can be administered orally in the form of solutions, powders or suspensions, which may contain flavouring or colouring agents, for immediate-, delayed-, modified-, sustained-, pulsed- or controlled-release applications.

In addition to in-feed or in-drink administration with part of the cattle's normal diet, it is envisaged that the active agent could be separately administered between normal feeding and drinking, e.g. in the form of a palatable "treat" such as in a molasses-based formulation.

For aqueous suspensions and/or elixirs, the active agent may be combined with various sweetening or flavouring agents, colouring matter or dyes, with emulsifying and/or suspending agents and with diluents such as water, ethanol, propylene glycol and glycerin, and combinations thereof. Additional physical and chemical stabilising agents may also be included to maintain or enhance the stability of the active agents in the said formulation.

The active agent may also be delivered via a long-acting bolus formulation directly to the rumen, wherein the formulation device is retained within the ruminoreticular sac for prolonged periods of time to facilitate sustained release. Ruminal retention of the formulation device as described in this instance may be achieved using dense matrices or reservoirs based on aluminium or steel cylinders or pellets formed from a mixture of clay, drug and other ingredients.

The active agent may, in certain cases, also be administered parenterally, for example, intravenously, intraarterially intraperitoneally, intramuscularly or subcutaneously, or administered by infusion techniques. For such parenteral administration the active agent is best used in the form of a sterile aqueous solution which may contain other substances, for example, enough salts or glucose to make the solution isotonic with blood. The aqueous solution should be suitably buffered (preferably to a pH of from 3 to 9), if necessary. The preparation of suitable sterile parenteral formulations is readily accomplished by terminal sterilisation methodology or by aseptic manufacture using standard pharmaceutical techniques well known to those skilled in the art.

Thus unit doses of the active agent may contain from 0.001 mg to 20 g of active agent for administration singly or two or more at a time, as appropriate. For example acarbose has been administered at 15 g per animal per day in 2 separate feeds. A target range for an active compound is up to ca. 3 g/animal/day. The vet/farmer in any event will determine the actual dosage that will be most suitable for any individual animal or group of animals and it may vary with the age, weight, diet and response of the particular animal. The above dosages are exemplary of the average case. There can, of course, be individual instances where higher or lower dosage ranges are merited and such are within the scope of this invention. The skilled person will appreciate that, in the treatment of certain conditions such as acute acidosis the active agent may be given as a single dose as needed or desired.

The active agent will normally be administered orally or by any other suitable route (which can eventually reach the rumen), in the form of preparations comprising the active ingredient, optionally in the form of a non-toxic organic, or inorganic, acid, or base, addition salt, in an acceptable veterinary/pharmaceutical dosage form. Depending upon the disorder and animal to be treated, as well as the route of administration, the compositions may be administered at varying doses (see below).

While it is possible to administer the active agent directly without any formulation, the active agents are preferably employed in the form of a pharmaceutical, or veterinary, formulation comprising a pharmaceutically, or veterinarily, acceptable carrier, diluent or excipient and active agent. The carrier, diluent or excipient may be selected with due regard to the intended route of administration and standard pharmaceutical, and/or veterinary, practice. Compositions comprising the active agent may contain from 0.1 percent by weight to 90.0 percent by weight of the active ingredient.

The formulations will vary with regard to the weight of active compound contained therein, depending on the species of animal to be treated, the severity and type of condition and the body weight of the animal. For parenteral and oral administration, typical dose ranges of the active ingredient are 0.0001 to 1000 mg per kg of body weight of the animal. Preferably the range is 0.001 to 20 mg per kg. For example acarbose was administered at 16 mg/kg. More preferably the range is 0.001 to 5 mg/kg, and most preferably 0.001 to 0.5 mg/kg.

It is to be appreciated that all references herein to treatment include curative, palliative and prophylactic treatment.

The efficacy of agents can be demonstrated using the following Test Methods, in which acarbose is used as an example of a suitable amylase and/or α-glucosidase inhibitor.

TEST METHODS

Rumen Bacterial Amylase Assay—Protocol 1

The assay utilises a Sigma amylase kit (577) to determine whether compounds inhibit the action of rumen fluid supernatant amylases. The enzymatic reactions involved in the assay are as follows:

5 ET-$G_7$PNP→(α-amylase)→2 ET-$G_5$+2 $G_2$PNP+2 ET-$G_4$+2 $G_3$PNP+ET-$G_3$+$G_4$-PNP2 $G_2$PNP+2 $G_3$ PNP→(α-glucosidase)→4 PNP+10 glucose α-Amylase hydrolyses 4,6-ethylidene-$G_7$-PNP (ET-$G_7$PNP) to $G_2$, $G_3$ and $G_4$ PNP fragments. α-Glucosidase (α-1,4-glucan glucohydrolase EC 3.2.1.3) hydrolyses $G_2$PNP and $G_3$PNP to yield p-nitrophenol and glucose. Five moles of substrate (ET-$G_7$PNP) is hydrolysed to yield 4 moles of p-nitrophenol. p-Nitrophenol absorbs light as 405 nm, and following a two minute lag period the rate of increase in absorbance at 405 nm is directly proportional to α-amylase activity in the well.

Rumen fluid was collected from 4-month-old Hereford x Friesian calves (125–135 kg, supplied by Cwmnant Calves Ltd. Cwmnant. Tregaron. Ceredigion) fed on diet GH 313. The rumen fluid was collected from slaughtered calves into pre-warmed vacuum flasks, as soon as possible after euthanasia. It was then filtered through a double layer of absorbent gauze (Absorbent gauze BP, GAUZ 4 from Robert Bailey plc, Stockport) to remove hay and feed particles. The liquid was centrifuged at a relative centrifugal force of 23,300 for 60 minutes, and the supernatant decanted, avoiding contamination from the loose top layer of the pellet by careful pouring. The supernatant was then aliquoted into 50 ml plastic tubes and frozen at −20° C. When required for use in an assay the rumen fluid supernatant was thawed by standing the tubes in cold water. Test compounds or controls were dispensed into the 96-well assay plate at 4 μl/well. 100 μl per well of Sigma amylase reagent 577 (made up to half the volume described in the instructions (i.e. 10 ml for a 577-20 vial)) was then added to each well, followed by 100 μl per well of rumen fluid supernatant. A T=0 reading at 405 nm was taken at this stage using an Anthos plate reader. The plate was then incubated at room temperature or 37° C. until an optical density window of approximately 1.000 U was seen (typically one hour at 37° C. or three hours at room temperature). A second reading was taken at 405 nm, and the first reading subtracted from it. Active compounds cause a reduction in the optical density readings when compared to the control without the agent being tested.

Results - IC50s in rumen fluid amylase screen (using Sigma kit 577)

| Compound | Average IC50 (μM) | Number of assays |
|---|---|---|
| Acarbose | 2.03 | n = 34 |
| Trestatin A | 0.17 | n = 8 |
| Trestatin B | 2.89 | n = 6 |
| Trestatin C | 0.09 | n = 6 |
| V-1532 | 0.57 | n = 2 |
| Example 7 | 2.06 | n = 8 |
| Example 8 | 0.44 | n = 10 |

Dose Response of Acarbose in the Rumen Bacterial Amylase Assay [Acarbose Concentration in Molar Units]

Rumen Fluid Glucosidase Assay Protocol

This assay is used to determine IC50 values for inhibitors of bacterial glucosidase activity from bovine rumen fluid cell suspension (RFCS) using a colorimetric assay.

The assay measures conversion of maltose into glucose. Rumen fluid cells are incubated with maltose in the presence of inhibitors, and the amount of glucose produced is assessed using a red colourimetric endpoint. The higher the level of inhibition the lower the glucose produced and the less red colour produced. The plates are read at 450 nm.

Main reaction:

Maltose+glucosidase→glucose

Glucose assay

Glucose+ATP→G-6-P and ADP (Hexokinase and $Mg^{2+}$)

G-6-P and NADP→6-phosphogluconate (6-PG) and NADPH

NADPH+phenazine methosulfate (PMS)→NADP+ PMSH

PMSH+INT (iodonitrotetrazolium chloride)→PMS+ INTH

INTH is deep red coloured.

Rumen fluid was collected from a fistulated five year old dry Guernsey donor cow fed twice daily on 1.4 kg GH313 and 2.3 kg hay. The rumen fluid was collected into pre-warmed vacuum flasks. It was then filtered through a double layer of absorbent gauze (Absorbent gauze BP, GAUZ 4 from Robert Bailey plc, Stockport) to remove hay and feed particles. The liquid was centrifuged at a relative centrifugal force of 650 for 15 minutes to remove food particles and protozoa. The supernatant was decanted into fresh tubes and centrifuged at a relative centrifugal force of 23,300 for 60 minutes. The supernatant and the loose top layer of the pellet were discarded. The pellet was resuspended in PBS at 1:8 of original volume i.e. 50 ml of PBS for the pellet from 400 ml of rumen fluid, and frozen at −20° C. When required for use the cells were thawed by standing the tube in cold water, and then diluted to 4.5 μl of cells/well (45 μl/ml).

Test compounds or controls were dispensed into the 96-well assay plate at 2 μl/well, followed by 50 μl per well of 10 mM maltose and 50 μ/well of rumen fluid cell suspension. The plate was incubated at 37° C. for 1 hour. Sigma glucose detection kit 115A was reconstituted by addition of 17 ml of Millipore water and 4 ml of colour reagent to each vial. 100 μl of this solution was added per well and the plate returned to the 37° C. incubator for 45 minutes. The plate was then read at 450 nm. Active compounds cause a reduction in the optical density readings when compared to the no-inhibitor control wells.

| Results - IC50s in rumen fluid glucosidase screen | | |
|---|---|---|
| Compound | Average IC50 (μM) | Number of assays |
| Acarbose | 1.08 | n = 7 |
| Trestatin A | 33.6 | n = 3 |
| Trestatin B | 4.10 | n = 2 |
| Trestatin C | 148.5 | n = 2 |
| V-1532 | 65.5 | n = 2 |
| Example 7 | 6.38 | n = 1 |
| Example 8 | 13.1 | n = 2 |

Rumen Bacterial Amylase Assay Protocol 2

The assay utilises digestion of amylose covalently linked to Remazol Brilliant Blue R to determine whether compounds inhibit the action of rumen fluid supernatant amylases. When the insoluble substrate is incubated with amylase blue dye is released into the well. This can be measured spectrophotometrically to determine how much amylase activity is present, and whether test compounds are inhibitors of amylase.

Rumen fluid was collected from a fistulated five year old dry Guernsey donor cow fed twice daily on 1.4 kg GH313 and 2.3 kg hay. The rumen fluid was collected into prewarmed vacuum flasks. It was then filtered through a double layer of absorbent gauze (Absorbent gauze BP, GAUZ 4 from Robert Bailey plc, Stockport) to remove hay and feed particles. The liquid was centrifuged at a relative centrifugal force of 23,300 for 60 minutes, and the supernatant decanted, avoiding contamination from the loose top layer of the pellet by careful pouring. The supernatant was then aliquoted into 50 ml plastic tubes and frozen at −20° C. When required for use in an assay the rumen fluid supernatant was thawed by standing the tubes in cold water. 100 μl per well of a 2% suspension of amylose azure (Sigma A3508) was added to each well from a beaker that was stirred throughout to ensure an even distribution of substrate. Test compounds or controls were dispensed into the 96-well assay plate at 4 μl/well, followed by 100 μl per well of rumen fluid supernatant. The plate was then incubated at 37° C. for 2.25 hours. 100 μl of liquid was removed gently from each well using a 12-channel pipette, transferred to a fresh 96-well plate and read at 620 nm. Active compounds cause a reduction in the optical density readings when compared to the no-inhibitor control wells.

| Results - IC50s in rumen fluid amylase screen (amylose azure) | | |
|---|---|---|
| Compound | Average IC50 (μM) | Number of assays |
| Acarbose | 2.39 | n = 4 |
| Trestatin A | 0.79 | n = 2 |
| V-1532 | 2.07 | n = 2 |
| Example 7 | 0.56 | n = 2 |
| Example 8 | 9.45 | n = 2 |

Protocol for Determination of Minimum Inhibitory Concentrations (MICs) in Aerobes MICs were determined by a standard agar dilution technique according to the National Committee for Clinical Laboratory Standards (NCCLS, M7 Edition A2). An outline of the method employed is detailed below.

The MICs were determined using the standard test medium, Mueller Hinton (MH) agar (Unipath).

Preparation of agar plates: 19 ml of test medium was added to appropriate doubling dilutions of test compound (1 ml) and mixed thoroughly. The mixture was poured into a petri dish (90 mm) and the agar allowed to solidify.

Preparation of inoculum: Four to five colonies of the test organism were inoculated from a MH agar plate culture into 10 ml MH broth (Unipath). The broth was incubated at 37° C. until visibly turbid. The density of the culture was adjusted to a turbidity equivalent to that of a 0.5 McFarland standard by the addition of saline (0.85% v/v).

Inoculation of agar plates: The plates were dried for approximately 1 hour in a 37° C. incubator. Plates were inoculated with a Multipoint Inoculator (Denley). The pins on this device deliver 0.001 ml inoculum to the plate (equivalent to $10^4$–$10^5$ organisms).

Incubation of plates: Plates were inverted and incubated at 37° C. for 18 hours.

Determination of endpoints: MICs were recorded as the lowest concentration of test compound that completely inhibited growth, disregarding a single colony or a faint haze caused by the inoculum.

References for this Section

National Committee for Clinical Laboratory Standards

Methods for dilution antimicrobial susceptibility tests for bacteria that grow aerobically—second edition.

Approved standard reference methods for the determination of MIC of aerobic bacteria by broth macrodilution, broth microdilution and agar dilution. Chair holder J. Allan Waitz, PhD DNAX Research Institute, NCCLS Document M7-A2

Villanova, Pa.: NCCLS, 1990

| RESULTS USING ACARBOSE IN THIS TEST: | | |
|---|---|---|
| No. | Bacterial species | MIC (μg/ml) |
| 1 | E. coli ATCC 10418 | >128 |
| 2 | E448 | >128 |
| 3 | E454 | >128 |
| 4 | E459 | >128 |
| 5 | E450 | >128 |
| 6 | E476 | >128 |
| 7 | E461 | >128 |
| 8 | E516 | >128 |
| 9 | E517 | >128 |
| 10 | E520 | >128 |
| 11 | Salm. enteritidis B1234 | >128 |
| 12 | B1227 | >128 |
| 13 | B1240 | >128 |
| 14 | B1218 | >128 |
| 15 | B1231 | >128 |
| 16 | B1233 | >128 |
| 17 | B1232 | >128 |
| 18 | B1235 | >128 |
| 19 | E. faecium 1.1.7 | >128 |
| 20 | 1.2.4 | >128 |
| 21 | 1.1.6 | >128 |
| 22 | 28.7.7 | >128 |
| 23 | 1.2.6 | >128 |
| 24 | 28.6.7 | >128 |
| 25 | 5.4 | >128 |
| 26 | 4.5 | >128 |
| 27 | 3.1 | >128 |
| 28 | 10.1 | >128 |
| 29 | E. faecalis 1.3.10 | >128 |
| 30 | 1.4.12 | >128 |
| 31 | 1.1.16 | >128 |
| 32 | 1.6.6 | >128 |

-continued

| RESULTS USING ACARBOSE IN THIS TEST: | | |
|---|---|---|
| No. | Bacterial species | MIC (μg/ml) |
| 33 | 1.3.13 | >128 |
| 34 | 1.10.4 | >128 |
| 35 | 28.5.7 | >128 |
| 36 | 1.9.5 | >128 |
| 37 | 1.1.4 | >128 |
| 38 | 28.6.9 | >128 |
| 39 | S. aureus 3.3 | >128 |
| 40 | 3.4 | >128 |
| 41 | 3.5 | >128 |
| 42 | 5.1 | >128 |
| 43 | 6.1 | >128 |
| 44 | 8.2 | >128 |
| 45 | 8.3 | >128 |
| 46 | 9.3 | >128 |
| 47 | 10.3 | >128 |

-continued

| RESULTS USING ACARBOSE IN THIS TEST: | | |
|---|---|---|
| No. | Bacterial species | MIC (μg/ml) |
| 48 | 10.4 | >128 |
| 49 | NCTC 6571 | >128 |

DIETS USED IN THE FOLLOWING TESTS

[All diets were provided by Grain Harvesters Ltd, The Old Colliery, Wingham, Canterbury, Kent CT3 1LS, England.]

| Material | Inclusion | Analysis | |
|---|---|---|---|
| GH313: | | | |
| BARLEY (fine) | 24.000 | VOLUME | 100.000 |
| WHEAT | 10.000 | PROTEIN | 14.005 |
| WHEAT MIDDLINGS | 11.900 | OIL | 3.794 |
| SUNFLOWER MEAL (EXT) | 5.100 | FIBRE | 8.501 |
| RAPESEED MEAL (EXT) | 10.000 | STARCH | 27.309 |
| PEAS | 7.500 | STARCH + SUGAR | 32.783 |
| WHOLE LINSEED | 1.200 | | |
| GRAIN SCREENINGS | 7.500 | | |
| UNMOLASSED SUGAR BEET | 13.900 | | |
| LIMESTONE GRANULES | 1.300 | | |
| SALT | 0.800 | | |
| GHS CATTLE SUPP. | 0.250 | | |
| ADDAROME Cattle Supplement | 0.020 | | |
| MOLASSES | 5.000 | | |
| VEGETABLE FAT (MIXER) | 1.500 | | |
| | 99.970 | | |
| GH633 | | | |
| BARLEY (fine) | 22.100 | VOLUME | 100.000 |
| WHEAT MIDDLINGS | 17.500 | PROTEIN | 15.122 |
| MAIZE GLUTEN | 8.800 | OIL | 4.700 |
| FISHMEAL (PROVIMI 66) | 2.500 | FIBRE | 9.601 |
| SUNFLOWER MEAL (EXT) | 4.500 | STARCH | 17.175 |
| RAPESEED MEAL (EXT 00) | 5.000 | SUGAR | 8.770 |
| LUCERNE PELLETS | 10.000 | | |
| MOLASSED SUGARBEET | 20.000 | | |
| LIMESTONE FLOUR | 0.400 | | |
| SALT | 0.650 | | |
| INT LAMB SUPPLEMENT (10 kg) | 1.000 | | |
| SPRAY VEGETABLE FAT | 1.600 | | |
| MOLASSES | 5.000 | | |
| MIXER VEGETABLE FAT | 1.000 | | |
| | 100.050 | | |
| GH651: | | | |
| BARLEY (fine) | 15.000 | VOLUME | 100.000 |
| WHEAT | 50.000 | PROTEIN | 13.984 |
| WHEAT MIDDLINGS | 11.000 | OIL | 3.206 |
| RAPESEED MEAL (EXT) | 14.400 | FIBRE | 4.539 |
| LIMESTONE GRANULES | 1.900 | STARCH | 39.523 |
| DICALCIUM PHOSPHATE | 0.030 | STARCH + SUGAR | 44.838 |
| SALT | 0.820 | | |
| GHS CATTLE SUPPLEMENT | 0.250 | | |
| COLBORN No. 3 | 0.100 | | |
| MOLASSES | 5.000 | | |
| VEG FAT (MIXER) | 1.500 | | |

-continued

| Material | Inclusion | Analysis | |
|---|---|---|---|
| GH654: | 100.000 | | |
| WHEAT MIDDLINGS | 22.000 | VOLUME | 100.000 |
| MAIZE GLUTEN | 16.600 | PROTEIN | 12.867 |
| SUNFLOWER MEAL (EXT) | 7.000 | OIL | 4.688 |
| RAPESEED MEAL (EXT) | 4.200 | FIBRE | 13.991 |
| OATFEED | 10.000 | STARCH | 10.109 |
| N. I. Straw | 10.000 | SUGAR | 5.352 |
| UNMOLASSED SUGAR BEET | 20.000 | | |
| LIMESTONE GRANULES | 1.200 | | |
| SALT | 0.680 | | |
| CALCINED MAGNESITE | 0.540 | | |
| AMMONIUM CHLORIDE | 0.050 | | |
| COLBORN Cattle Supplement | 0.250 | | |
| ADDAROME Cattle Supplement | 0.040 | | |
| MOLASSES | 5.000 | | |
| VEG. FAT (MIXER) | 2.500 | | |
| | 100.060 | | |

Evaluation of Agents Using the Rumen Simulation Technique (RUSITEC) to Model Chronic Acidosis.

The in vitro rumen simulation technique (RUSITEC), first described by Czerkawski and Breckenridge (1977) was used to evaluate the effect of the bacterial α-amylase and/or α-glucosidase inhibitor acarbose on daily pH profiles and VFA production using a commercial cattle concentrate ration (GH313—see later). Feeding 30 g/d of this ration with 2.5 g/d chopped barley straw had previously been found to give total volatile fatty acid (VFA) concentrations of more than 150 mM i.e. concentrations associated with chronic acidosis in vivo (Nagaraja, Galyean & Cole, 1998, supra)

Equipment: The apparatus consisted of two RUSITEC units each containing four-fermentation vessels. Each vessel had a volume of 1 liter, and was heated to 39° C. in a water bath. The feed was placed in a nylon bag (14×9 cm, 50 µm), and was gently agitated using a piston mechanism (8 strokes/min). Buffer (McDougall, 1948) was continuously infused at a rate of approximately 750 ml/day by an eight channel peristaltic pump (Watson Marlow). The effluent was collected in 1 liter glass bottles containing 20 ml of oxalic acid solution (12 g/100 ml in deionised water). This was added to inhibit further microbial activity Feed: Each vessel was fed daily with a bag containing 30 g of the commercial pelleted ration GH313 (89% dry matter) and 2.5 g barley straw (90% dry matter) chopped into 1–2 cm lengths. 7 g of corn starch (Sigma Cat. No. S4126) was added to the liquid phase of all fermenter vessels at feeding on the last four days of the experiment to simulate acute acidosis.

Rumen fluid donor: Rumen fluid was collected from a five year old dry Guernsey cow. The animal was fed twice daily with 1.4 kg GH313 and 2.3 kg hay. Rumen contents were collected via a rumen fistula (Bar Diamond Inc. P.O. Box. 60. Bar Diamond Lane. Parma. Id. 83660-0060. U.S.A)

Vessel inoculation: Rumen contents were taken from the fistulated donor animal at 08:00 h (before the morning feed). The material was carried to the laboratory in pre-warmed insulated flasks, and then strained through four layers of cotton gauze into another pre-warmed insulated flask. 70 g of the solid residue were weighed into each of eight nylon bags. One bag containing rumen solids, and one bag containing fresh feed was placed in the feed chamber for each vessel. The liquid contents of each vessel were 100 ml deionised water, 200 ml of buffer artificial and 500 ml of rumen fluid. After assembling and sealing the vessels, they were placed in the water baths and the piston rod attached to the drive bar. The effluent tubes were placed in the collection flasks. The head space in each vessel was flushed with $CO_2$ for 2 min., then the piston drive motor and buffer infusion pump were started.

Daily maintenance and sampling procedure: These procedures were carried out at the same time each day. Eight feed bags were prepared, and a 1 l dispenser bottle containing infusion buffer warmed to 39° C.

1. Drive motors were switched off and the infusion pump stopped. Infusion lines clamped and disconnected from the pump.
2. The fermentation vessels were removed from the water bath and serviced in turn.
3. For each vessel, the feed chamber was extracted and feed bags exchanged. On Day 2 the new bag replaced the one containing rumen solids, whilst on subsequent days the new bag replaced the one that has been incubated for 48 hours. Chamber then replaced in fermentation vessel.
4. The removed bag was placed in a small plastic bag and 25 ml buffer added from the dispenser. The bag was washed by squeezing in the buffer for 20 seconds, then the liquid was poured into the vessel. This washing procedure was repeated twice with fresh buffer.
5. After reassembling the vessel, it was replaced in the water bath and attached to the drive bar. The buffer line was reconnected and the pH electrode relocated. The effluent collection bottle was exchanged and the vessel headspace purged with $CO_2$ whilst the next vessel was being serviced.
6. This process was repeated for all vessels, then the drive motors and infusion pump were restarted when gassing was complete. For the last vessel gassing was for a similar duration as for the other vessels.

Treatment with acarbose: Acarbose was obtained as Glucobay™ tablets (Bayer, AAH Pharmaceuticals) Each tablet contains 100 mg acarbose. Duplicate vessels were treated with 0, 1, 10 and 100 mg/d of acarbose by adding 1 tablet to each of two feed bags to give 100 mg/vessel/d. The lower doses were prepared by dissolving/suspending a tablet in 10 ml buffer (giving a 10 mg/ml solution of acarbose). One ml of this solution was then added to 9 ml of buffer, giving a 1 mg/ml solution. One ml of each solution was then added to the contents of two feed bags, to give 10 and 1 mg/vessel/d. Finally, the acarbose was dried on to the feed by leaving the bags at room temperature overnight.

Analyses: Dry matter losses from the nylon bags after 48 hours incubation were measured by drying the washed bag contents in an oven for 23 h at 65° C. Effluent samples (10 ml) were taken daily and stored at −20° C. for subsequent VFA and lactate analysis. pH was automatically recorded at 17 min. intervals using equipment supplied by Philip Harris Education. A combination electrode was fitted in each vessel via a gas-tight port in the lid. Each electrode was connected to a SensorMeter, and four SensorMeters were connected to one DL plus 128 datalogger. The recorded pH values were downloaded to a PC running Datadisk 32 software (Philip Harris Education) and then transferred to a spreadsheet for further analysis. The electrodes were removed from the vessels (when the feed bags were being changed), rinsed and placed in pH7.0 standard buffer. The reading were 7.0+/−0.1 units throughout the experiment. The electrodes were recalibrated to pH 7.0 before being replaced in the vessels. VFAs were measured by adding 0.1 ml of a solution containing a mixture of 25 g/100 ml metaphosphoric acid and 1.2 g/100 ml crotonic acid to 1 ml of effluent. This mixture was centrifuged for 10 min. at 12000 g and an aliquot of the supernatant transferred to an autosampler vial. VFAs were resolved and quantified on a Hewlett Packard 6890 series gas chromatograph fitted with an autosampler and flame ionisation detector. The acids were resolved on a SGE Ltd 25 meter BP21 column (0.33 mm O.D., 0.22 mm I.D. 0.25 um film thickness). Nitrogen was used as the carrier gas with a flow rate of 1.9 ml/min. The oven temperature was 165° C., and injection ports and detectors were held at 250° C. Concentrations were calculated by using crotonic acid as an internal standard, and the system was calibrated using a standard solution containing acetic, propionic, butyric, iso-valeric and n-valeric acids. L-lactic acid was measured using Sigma kit 826, and D-lactate was measured using the same procedure, except L-LDH was replaced with D-LDH (Sigma Catalogue No. L2011) and L-lactate was replaced with D-lactate (Sigma Catalogue No. L0625). Assays was carried out on a 96-well microtitre plate and the absorbances measured using an Anthos microtitre plate reader fitted with a 340 nm filter. The system was calibrated by preparing solutions of D- and L-lactate from 0 to 100 mM.

Schedule:
Day
0 Inoculate.
3 Start collecting effluent
5 Start daily pH measurement.
10 Begin dosing with acarbose (0, 1, 10 or 100 mg/vessel/d) to pairs of vessels.
Continue to end of experiment.
18 Add extra starch to all vessels.
22 End experiment.

REFERENCES FOR THIS SECTION

Czerkawski, J. W. and Breckenridge, G. 1977. Design and development of a long-term rumen simulation technique (RUSITEC). *British Journal of Nutrition*, 38, 371–384.

McDougall, E. I. 1948. Studies on ruminant saliva. 1. The composition and output of sheep's saliva. *Biochemical Journal*, 43, 99–109.

Rusitec Results: Acarbose
Comparing the treatment period with the preceding control period indicated a dose-related change in VFA production of −16%, −10% +3% and −3% in response to additions of 100, 10, 1 and 0 mg/vessel/d of acarbose. There was a general shift of fermentation products from acetate and propionate to butyrate with all treatments between the control and treatment periods, resulting in increases in butyrate production of 134%, 76%, 27% and 24% respectively for the above doses. There was no L-lactate accumulation in this study, confirming that the model represented chronic rather than acute acidosis.

RUSITEC Result Using Example 8 and Acarbose
Experimental Outline:
Daily maintenance procedures as previously described for Acarbose.
Rumen fluid donor cow—Fed GH313 pellets plus barley straw.
Daily Feed—30 g GH313 pellets plus 2.5 g chopped barley straw.
Treatment Preparation
Acarbose: 1 tablet added to each bag to give 100 mg/vessel/d

EXAMPLE 8

Eight×57 mg pre-weighed samples stored in fridge in 380 2.1. On the day before the feed bags were to be placed in RUSITEC, a 57 mg sample was dissolved in 2.28 ml buffer (25 mg/ml). 0.21 ml of this solution was added to 1.9 ml buffer to give a 2.5 mg/ml solution. 1 ml of each solution was added to a prepared feed bag to give 25 and 2.5 mg/vessel/d. and dried overnight at room temperature.

Schedule:
Day
0 Inoculate.
4 Start collecting effluent
5 Start daily pH measurement
9 Review data, allocate vessels to treatments.
10 Begin treatments.
18 End experiment.

Results and Conclusions: In this experiment 0.02 mM Example 8 gave an increase in mean daily pH of 0.3 units compared to 0.7 units for 0.2 mM acarbose. Treatments of 100 mg acarbose, 25 or 2.5 mg Example 8 per vessel per day, or none (control) caused changes in total VFA production of −15%, −8%, −1% and −11% when compared with the preceding control period. There was a trend for redistribution of fermentation products, with butyrate production increasing in the treatment period compared with the control. The proportional increases were 113%, 20%, 18% and 1% respectively. There was no L-lactate accumulation in this study, confirming that the model represented chronic rather than acute acidosis.

In Vitro Rumen Propionic Acid Screen
Reagents
Rumen Fluid: An eight year old dry Guernsey cow, fitted with a rumen fistula (Bar Diamond Inc. P.O. Box. 60. Bar Diamond Lane. Parma. Id. 83660-0060. U.S.A) was fed twice daily with 1.4 kg GH633 and 2.3 kg hay. This animal was used as a source of rumen contents, which were taken at 08:00 h (before the morning feed). The material was carried to the laboratory in a pre-warmed insulated flask, and then strained through four layers of cotton gauze into another pre-warmed bottle, which was stored in an incubator at 40° C. until the fluid was dispensed into the assay tubes.

| Buffer: Dissolve the following in deionised water. | | |
|---|---|---|
| | g/l | g/500 ml |
| Na$_2$HPO$_4$.2H$_2$O | 9.88 | 4.94 |
| KH$_2$PO$_4$ | 3.40 | 1.70 |
| NaH$_2$PO$_4$.H$_2$O | 1.11 | 0.55 |
| Adjust to pH 7.0 with 1 M NaOH. | | |

Deoxygenate by bubbling with an oxygen-free gas mixture (10% CO$_2$, 5% H$_2$ in nitrogen) for at least 5 min.

Substrate Mixture:

68 g corn starch. Ex Sigma Cat. S-4126.

17 g α-cellulose. Ex Sigma Cat. C-6429.

15 g Type 1 soya flour. Ex Sigma Cat. S-9633.

Mix well.

Immediately before use, suspend in buffer at 200 mg/ml.

Metaphosphoric/crotonic Acids Solution:

The following were dissolved in deionised water.

25% (w/v) metaphosphoric acid. Ex. BDH Cat. 291904A plus 1.2% (w/v) crotonic acid. Ex Sigma Cat. C-4630

VFA Standard Mixture:

The following were dissolved in 100 ml of deionised water.

| | mwt | nominal weight (mg) | concentration mM |
|---|---|---|---|
| Sodium acetate. Ex Sigma Cat. S-7670 | 136.1 | 680 | 50 |
| Sodium propionate. Ex Sigma Cat. P-1880 | 96.1 | 192 | 20 |
| Sodium butyrate. Ex Sigma Cat. B-5887 | 110.1 | 110 | 10 |
| n-Valeric acid. Ex Aldrich Cat. 24,037-0 | 102.1 | 102 | 10 |
| iso-valeric acid. Ex Sigma Cat. I-7128 | 102.1 | 102 | 10 |

1 ml of metaphosphoric/crotonic acids solution added to 10 ml of VFA mixture then aliquoted into automatic liquid sampler vials.

Procedure:

The assay was conducted in 16 ml Sorvall centrifuge tubes

A tablet containing 100 mg of acarbose was placed in 10 ml of buffer and shaken until the tablet was completely disrupted, giving a 10 mg/ml solution of acarbose. This solution was serially diluted to 2, 0.4, 0.08 and 0.016 mg/ml with buffer.

One ml of these solutions was added to triplicate assay tubes (giving final assay mixture concentrations of 1000, 200, 40, 8 and 1.6 ug/ml). Control tubes were prepared by replacing the acarbose solution with buffer. One ml of substrate suspension was added to all the assay tubes, followed by 3 ml of warmed degassed buffer and then by 5 ml of strained rumen liquor. Suba-Seal stoppers (No. 29) were fitted, and the head pressure in the tubes reduced by passing a hypodermic needle attached to a vacuum line through the stopper until the tube contents frothed. The tubes were then placed in a 40° C. incubator for 6 hours and shaken hourly.

Pre-incubation VFA concentration were determined by preparing three tubes as for incubation but 1 ml metaphosphoric/crotonic acids solution was added immediately following the rumen liquor. These tubes were stored at 4° C. and processed with the post-incubation tubes.

The incubation was terminated after 6 h by removing the stoppers and adding 1 ml of metaphosphoric/crotonic acids solution. The tubes were then centrifuged for 8 minutes at 18,000 g at 4° C., and an aliquot of the supernatant stored in an automatic liquid sampler vial until required for VFA analysis by gas chromatography. (as described in RUSITEC protocol)

Result Calculation:

Production of total VFA and propionate during the incubation was determined as follows. Firstly, first the pre-incubation concentrations of total VFA and propionic acid were calculated as the mean of the analyses of the pre-incubation samples. Then for each incubated sample, post-minus pre-incubation concentration gave production during incubation. The molar proportion of propionic acid in total VFA.produced during the incubation was also calculated.

The total VFA and % propionic acid values were meaned for the replicate tubes, and the mean control total VFA and % propionic acid values normalised as 100%, then the change caused by the test treatments expressed relative to this value.

| acarbose *Dose μg/ml | Total VFA | % Propionate |
|---|---|---|
| 1000 | 50 | 88 |
| 200 | 58 | 81 |
| 40 | 63 | 74 |
| 8 | 72 | 74 |
| 1.6 | 92 | 94 |
| 0.32 | 96 | 97 |
| 0 | 100 | 100 |

In vivo Testing in Fistulated Cattle

Objective: To determine the effect of the agent for testing, in this case acarbose, on chronic rumen acidosis induced in fistulated cattle. A rumen pH profile representative of chronic acidosis was induced by stepwise increase in the level of concentrate feeding of a specified diet and a reduction in the roughage offered. This was followed by treatment of each animal with acarbose, administered via a permanent rumen fistula, to assess its ability to normalise rumen pH.

Experimental Animals: Six fistulated Hereford x Friesian steers, weighing 170–230 kgs (supplied by Cwmnant Calves Ltd. Cwmnant, Tregaron, Ceredigion)

Treatment: Glucobay® 100. Acarbose 100 mgs per tablet.

Management: The cattle were fed GH651 cattle high cereal beef pellets (variable amount) with barley straw (variable amount) divided over two equal feeds, given at around 08.00 hr and 14.30 hr each day. Precise feeding times were recorded. Water was available ad-lib. Cattle were individually housed in pens (9 square meters per pen) in a building environmentally controlled to 16° C.

Design:

| Group | Treatment | Form[n] | Route | Acarbose (g/trt) | Volume (ml) | No. of Animals |
|---|---|---|---|---|---|---|
| 1 | Acarbose | Aq. Sol. | Through fistula | 4.0 | 100 | 6 |

While chronic acidosis was being induced, manual pH measurements were taken approximately 5 and 8 hours post-morning feed. Rumen fluid samples were taken for VFA and lactate analysis. Once a suitable pH profile was generated (see procedure section), each steer was fitted with a harness to carry an automated pH sampling and recording device (Philip Harris Plus 128 Data logger.+p.H. First Sense Recorder). Rumen pH values were automatically recorded every 17 minutes for a maximum of 21 days. Rumen fluid samples (10 ml) were taken twice daily for measurement of VFA levels, molar ratios and lactate levels. These were collected (by manually removing a sample of rumen content with a small stainless steel ladle, filtering and transferring to a 10 ml polypropylene vial) just before acarbose was added to the rumen at both dosing times. The pH probes were removed for cleaning and recalibration immediately pre-morning feed.

Results: The daily pH curves were used to calculate the period that rumen pH was below pH5.5, and therefore indicative of chronic acidosis.

Rumen fluid samples were taken at 13:00 and 16:00 i.e. before and after the afternoon feed. There was little difference in total VFA concentrations at the 13:00 samples, but the VFA concentration in the 14:00 samples fell during the treatment period. This was consistent with the pH profiles. At all sampling times the percentage of propionate was lower during the treatment period. There was no accumulation of lactic acid in the rumen fluid samples, indicating that the animals did not experience acute acidosis during the experiment.

EFFICACY OF ACARBOSE IN LACTATING DAIRY CATTLE

The study measured the effect of acarbose on rumen pH, milk yield and milk composition in lactating cows in which chronic acidosis had been induced by offering a highly fermentable diet. The study included measurement of rate of adaptation to the introduction and removal of acarbose.

Experimental animals were six lactating multiparous Holstein/Friesian cows between 5 and 11 years of age and 500–750 kg, with permanent rumen cannulas. The animals started the experiment in early lactation, but not before peak lactation, to allow greater experimental sensitivity. The principal measurements in this study were pH in the ventral sac of the rumen, milk yield and milk composition.

Management practices complied with the UK Home Office code of practice for the Housing and Care of Animals Used in Scientific Procedures (1989).

Design: Animals enrolled into the study received test article for 21 consecutive days from the start time points described below.

| Treatment Group | Supplement fed from Day 0 | Supplement fed from Day 21 | Supplement fed from Day 42 | Number of Animals |
|---|---|---|---|---|
| T01 | A | B | A | 3 |
| T02 | B | A | B | 3 |

A = Control supplement ration
B = Acarbose containing supplement ration

Procedure:

Masking/Bias-Reducing Methods: Six lactating multiparous Holstein/Friesian cows were enrolled on to the study on Day—1. Animals were paired based on their calving date (cows with similar dates paired together). Within each pair, one animal received T01 and the other T02. The treatment was assigned at random. Where possible, the randomisation was constrained so that the average feed intakes per treatment group were similar.

Methods: At approximately two weeks prior to Day 0, eight animals began a preliminary feeding period designed to identify a feeding regimen that induced acidotic pH levels in the rumen. Each cow was held in a tie stall from this point until completion of the study. Control total mixed ration (TMR) was fed and where necessary the amount and composition adjusted to establish a minimum rumen pH of 5.0–5.5. The mean intake over the last 5 days of the preliminary period was calculated and this mean amount was offered to each animal throughout the trial. Unconsumed food was removed and weighed on a daily basis and prior to the morning feed.

The TMR was supplemented with 0.5 kg/day ground wheat with either no additive (Control) or containing the test article (acarbose at 15 g per day), and offered separately in equal halves over the morning and afternoon feeds. An automatic watering system was also used to offer water ad-libitum.

| TMR composition: | |
|---|---|
| Ingredient | % in total ration DM |
| Grass silage | 10.0 |
| Maize silage | 30.0 |
| Cracked wheat | 16.7 |
| Ground barley | 9.2 |
| Rapeseed meal | 4.1 |
| Soyabean meal | 6.1 |
| Molassed SBP | 9.2 |
| Wheatfeed | 8.2 |
| Regumaize | 4.0 |
| Fishmeal | 1.0 |
| Minerals | 1.5 |
| Total | 100.0 |

From the start of the study, all animals were milked twice daily through a pipeline system at approximately 06.30 h and 16.00 h. Milk yield weight was manually recorded and then transcribed to an electronic daily milk file.

On Day—1, each animal was physically examined by a veterinary surgeon to assess physical and clinical normality. Animals met all of the inclusion criteria and none of the exclusion criteria.

On Day 0, the test article feeding regimen described in DESIGN began. Three animals followed the design Control/Treatment/Control (A/B/A) on three consecutive experimental periods whilst a second group of three animals followed the opposite treatment sequence (B/A/B). Experimental feeding periods lasted 3 weeks, consisting of 2 weeks for adaptation and a final week for detailed measurements.

Animals were fed twice daily at unequal intervals at approximately 08.00 h and 15.00 h (i.e. 7 and 17-h intervals) to allow rumen sampling for pH measurement to be concentrated during the period of minimum pH (estimated to be 2–4 h after the second feed). Each animal was offered 0.5 kg/day ground wheat supplement to the TMR divided equally over the two feeds and containing either no additive (Supplement A) or the test article (Supplement B).

Each animal completed the study after the final pH measurement of the third experimental period on Day 62.

Measurements: Automated pH measuring equipment (Philip Harris Plus 128 Data logger+pH First Sense Recorder) was used to record rumen pH values every 17 minutes. A 10 mL–15 mL sample of rumen fluid taken at 07.30 hrs and two samples taken at approximately minimum pH (at approximately 18.00 hrs and 20.00 hrs) were frozen immediately at −20° C. for further analysis. Fresh weight of TMR offered and refused was recorded daily for each animal. During non-measurement weeks (i.e. prelim period and adaptation weeks 1 and 2 in each experimental period), dry matter (DM) of main forage components (grass and maize silages) were determined approximately weekly (or more frequently if it appears necessary from visual assessment of the silage). For measurement weeks (i.e. week 3 in each experimental period), the DM of the TMR were measured daily for the last 5 days while a bulk of each of the individual TMR components (grass silage, maize silage, concentrate mix, ground wheat) were prepared from the same 5 days for subsequent diet analysis (i.e. one sample of each main feed per period). Only one sample of Regumaize was taken during the study as it is a single bulk liquid. Refusals were sampled for DM determination during the last 5 days of each experimental period. Single 20 ml milk samples for fat, protein and lactose were taken at am and pm milkings on 3 alternate days in each adaptation week. During measurement week milk samples were taken on the last 5 consecutive days. Each milk sample was analysed separately. Additionally a further 20 ml milk sample was taken on each occasion that milk was sampled during the measurement weeks and immediately frozen at approximately −20° C. for possible subsequent analysis. Daily milk yield data was generated by totalling the morning and afternoon milkings on a given date. Live weight was measured in each experimental period for each animal.

Results: Rumen pH was calculated as time below pH5.5 (i.e. in a state of chronic acidosis) for the treatment and control periods. The average time below pH 5.5 was 4.3 hours for control periods and 3.4 hours for treatment periods. Milk fat increased dramatically in treated animals, from an average of 1033 grams per day to 1281 grams per day. The proportion of fat in the milk was also increased, from 32.8 g/L to 46.1 g/L.

Acute Acidosis Model: Assessment of Acarbose
Experimental Design:

| | Treatment | | |
|---|---|---|---|
| No. | Description | Route | No. Animals |
| 1 | Control: ~200 mL water BID for 7 days pre-challenge, 12.5 g/kg BW of challenge mixture* | Cannula | 5 (3 dry cows and 2 heifers) |
| 2 | Acarbose: 1.07 mg acarbose/kg BW dissolved in ~200 mL water BID for 7 days pre-challenge, 12.5 g/kg BW of challenge mixture containing .02 g/kg BW acarbose | Cannula | 5 (2 dry cows and 3 heifers) |

*48.4% cornstarch, 48.4% ground corn, 2.1% sodium caseinate, 1.1% urea (food grade) suspended in approximately 5 gallons lukewarm water Procedures: Ten Holstein dried off cows and heifers (initial weight 740±27 (SE) kg, range=606–870 kg) were group-housed during the pre-treatment period and individually housed during the experimental period. Animals were moved to a head-gate during sample collection, treatment and first challenge. Subsequently, they were sampled and dosed in their individual pens. Animals were offered approximately 5 kg alfalfa hay, 16 kg silage, 6 kg concentrate and 0.5 kg straw daily in a total mixed ration offered in two feedings (60:40 concentrate:roughage diet). They were bedded on straw only during the pre-treatment period. Water was provided ad libitum. Animals were adapted to the lactating ration for at least 10 days before treatments were administered. From a group of 6 dry cows and 5 non-lactating heifers, ten were selected based on previous exposure to challenge and general health. Animals were paired by body weight and were randomly assigned to control and acarbose treatment groups within pair, ensuring similar distribution of heifers and cows. On days 0–6 of treatment, animals received 1.07 mg acarbose/kg dissolved in ~200 mL water through the rumen cannula just before AM (07:30) and PM (16:00) feedings. Treatment 1 animals received an equivalent amount of water only. On days 7 and 8, each animal was administered a challenge through the cannula. When pH reached ~4.5 and there was evidence of L-lactate production, acute acidosis was considered to be induced. When an animal experienced acute acidosis by these criteria, rumen contents were removed and the rumen inoculated with rumen contents from a donor animal. Animals were weighed on days—1 and 5 for calculation of acarbose dosing and challenge amounts. To measure rumen fluid pH animals were fitted with a harness to hold an automatic pH data recording system. The rumen pH was recorded every 10 min during the days of challenge until an animal experienced acute acidosis. Rumen fluid samples were taken (~50 mL) from the rumen cannula through a filtered sampling tube. Sampling times were just before each challenge, and 3, 6, 8, 10 and 12 hrs after each challenge. The pH was measured immediately. Samples for VFA and lactate analysis were prepared by adding 10 ml of rumen fluid to 1 ml of a solution containing a mixture of 25 g/100 ml metaphosphoric acid and 1.2 g/100 ml crotonic acid straight after collection. In some cases the sample was filtered through gauze before pH measurement and acid treatment. This mixture was centrifuged for 10 min at 12000 g. One aliquot of the supernatant was removed for immediate lactate analysis, one frozen for subsequent lactate analysis using Sigma kit 826. A third aliquot was transferred to an autosampler vial for subsequent VFA analysis. An initial determination of L-lactate was made during the study to establish acidotic status using Sigma kit 735. Subsequently D and L-lactate were re-measured for statistical analysis as described below. VFA's were measured on a Hewlett Packard 6890 series gas chromatograph fitted with an autosampler and flame ionisation detector. The acids were resolved on a SGE Ltd. 25 meter BP21 column (0.33 mm O.D., 0.22 mm I.D. 0.25 um film thickness). Nitrogen was used as the carrier gas with a flow rate of 1.9 ml/min. The oven temperature was 165° C., and injection ports and detectors were held at 250° C. Concentrations were calculated by using crotonic acid as an internal standard, and the system was calibrated using a standard solution containing acetic, propionic, butyric, iso-valeric and n-valeric acids.

Results:

pH: For the challenge pH data are presented as a calculation of the time that rumen pH was below a range of cut-offs. The first challenge did not induce acute acidosis, but after the second challenge, four of the control cattle had rumen pH values below 4.5. The short duration below pH 4.5 was due to their removal from the study at that point. Rumen pH remained above 5.0 in all the treated cattle, indicating that acarbose prevented acute acidosis following carbohydrate challenge. The treatment effect of reducing the number of cows that became acidotic was shown to be significant (P<0.5) by a simple contingency table analysis.

Lactates: There was no lactate detected after the first challenge, but levels increased to >50 mM for four of five controls within 10 hrs of the challenge on the second and remained at zero in all the acarbose-treated animals. The fifth control, which had pH of ~5.0, had a maximum level of lactate of 6 mM. Mean D-, L- and total lactates from the second challenge are summarized in the table. All lactates were higher in the control than treatment group and there was a trend for treatment by time interaction (the differences became greater over time).

| Group Mean D-Lactate, L-lactate and Total Lactates in Samples from Day 2 Challenges (mM) | | | | | | |
|---|---|---|---|---|---|---|
| | D-Lactate | | L-Lactate | | Total-Lactate | |
| Hours Post Second Challenge | Control | Acarbose | Control | Acarbose | Control | Acarbose |
| 0 | 11.48 | 0.67 | 3.82 | 0.35 | 15.30 | 1.02 |
| 3 | 42.93 | 3.63 | 15.33 | 1.28 | 58.26 | 4.91 |
| 5 | 58.19 | 10.91 | 17.80 | 3.08 | 76.08 | 13.99 |
| 7 | 74.69 | 18.00 | 18.98 | 4.93 | 93.92 | 22.93 |
| P Values | | | | | | |
| Treatment | | .04 | | .03 | | .04 |
| Time | | <.01 | | <.01 | | <.01 |
| Treatment *Time | | .13 | | .14 | | .12 |

DISCUSSION/CONCLUSIONS

Twice a day acarbose treatment reduced pH responses to a high carbohydrate load and blocked L-lactate production in response to the load. The pH responses to the first challenge were similar for the two groups; it was the second challenge that allowed distinction. This is similar to the observations of Cowe, et al. (J. Anim. Sci. 77:2259, 1999) in which acute acidosis is induced after multiple challenges.

What is claimed is:

1. A formulation, which comprises:

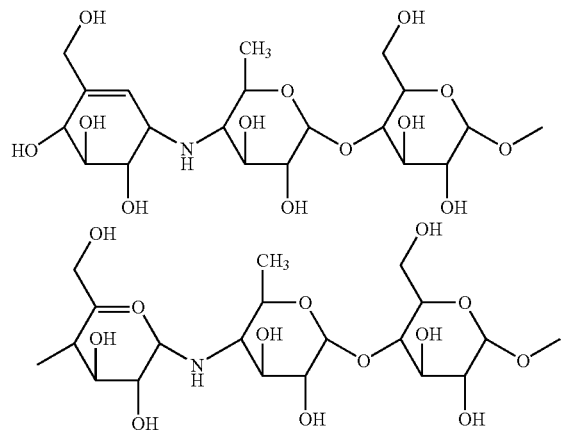

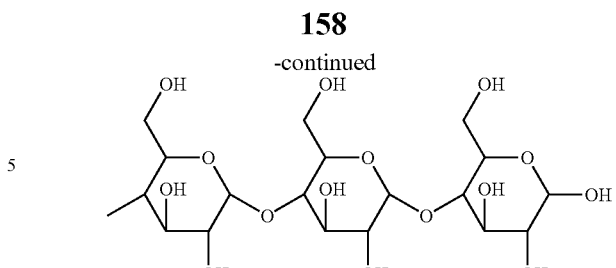

in admixture with a suitable excipient, diluent or carrier, and an optional stabilizer, selected with regard to the intended route of administration and standard pharmaceutical/veterinary/farming practice.

2. A compound of the formula:

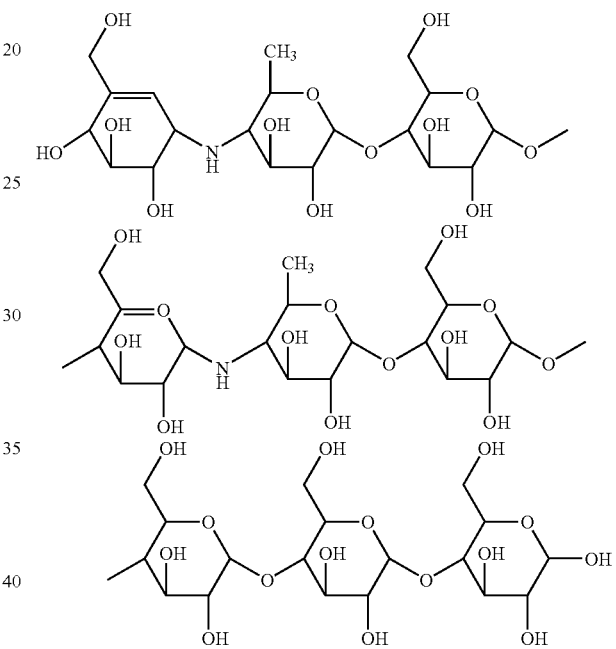

or veterinarily acceptable salt, solvate, hydrate or prodrug thereof.

* * * * *